US012745975B2

(12) United States Patent
Adler et al.

(10) Patent No.: US 12,745,975 B2
(45) Date of Patent: Sep. 29, 2026

(54) IN VIVO FLUID FLOW SENSOR

(71) Applicant: CANARY MEDICAL SWITZERLAND AG, Baar (CH)

(72) Inventors: Mark A. Adler, Carlsbad, CA (US); Steven Cazarez, San Diego, CA (US); Jeffrey M. Gross, Carlsbad, CA (US)

(73) Assignee: Canary Medical Switzerland AG, Baar (CH)

( * ) Notice: Subject to any disclaimer, the term of this patent is extended or adjusted under 35 U.S.C. 154(b) by 0 days.

(21) Appl. No.: 18/848,861

(22) PCT Filed: Mar. 22, 2023

(86) PCT No.: PCT/US2023/015948
§ 371 (c)(1),
(2) Date: Sep. 19, 2024

(87) PCT Pub. No.: WO2023/183417
PCT Pub. Date: Sep. 28, 2023

(65) Prior Publication Data

US 2026/0114838 A1 Apr. 30, 2026

Related U.S. Application Data

(60) Provisional application No. 63/322,623, filed on Mar. 22, 2022.

(51) Int. Cl.
*A61B 5/00* (2006.01)
*A61B 8/00* (2006.01)
(Continued)

(52) U.S. Cl.
CPC .............. *A61B 8/06* (2013.01); *A61B 8/0883* (2013.01); *A61B 8/4227* (2013.01);
(Continued)

(58) Field of Classification Search
CPC ....... A61B 8/06; A61B 8/0883; A61B 8/4227; A61B 8/4281; A61B 8/4477;
(Continued)

(56) References Cited

U.S. PATENT DOCUMENTS 5,305,745 A 4/1994 Zacouto
2001/0027384 A1 10/2001 Schulze et al.
(Continued)

OTHER PUBLICATIONS

International Search Report and Written Opinion for International Application No. PCT/US2023/015948, dated Aug. 10, 2023, 23 pages.
(Continued)

*Primary Examiner* — Joel F Brutus

(57) ABSTRACT

Disclosed are devices, systems, and methods for in vivo monitoring of the flow of a biological fluid in an anatomic structure, such as blood flow through a heart valve (e.g., mitral valve, tricuspid valve, and/or aortic valve) or heart chamber. The disclosed devices, systems, and methods can continuously measure and evaluate blood flow forward and backward at an inlet of a heart valve for determination of
(Continued)

heart function or dysfunction and/or in compilation with other monitored data that can be used to measure or predict secondary factors.

20 Claims, 23 Drawing Sheets

(51) Int. Cl.
*A61B 8/06* (2006.01)
*A61B 8/08* (2006.01)

(52) U.S. Cl.
CPC .......... *A61B 8/4281* (2013.01); *A61B 8/4472* (2013.01); *A61B 8/4477* (2013.01); *A61B 8/4494* (2013.01); *A61B 8/5207* (2013.01); *A61B 8/5223* (2013.01); *A61B 8/565* (2013.01); *A61B 2560/0214* (2013.01); *A61B 2560/0462* (2013.01); *A61B 2562/0204* (2013.01); *A61B 2562/028* (2013.01); *A61B 2562/14* (2013.01); *A61B 2562/227* (2013.01)

(58) Field of Classification Search
CPC ... A61B 8/4494; A61B 8/5207; A61B 8/5223; A61B 8/565; A61B 2562/14; A61B 2562/227; A61B 2562/028; A61B 2562/0204
See application file for complete search history.

(56) References Cited

U.S. PATENT DOCUMENTS

| | | | | |
|---|---|---|---|---|
| 2004/0138568 | A1 | 7/2004 | Lo et al. | |
| 2004/0236253 | A1 * | 11/2004 | Vortman | G10K 11/346<br>601/2 |
| 2007/0163353 | A1 * | 7/2007 | Lec | A61B 5/6876<br>73/700 |
| 2010/0331644 | A1 | 12/2010 | Neale et al. | |
| 2012/0095352 | A1 | 4/2012 | Tran | |
| 2017/0224279 | A1 | 8/2017 | Cahan et al. | |
| 2018/0303419 | A1 * | 10/2018 | Muñoz | A61B 8/4477 |
| 2019/0328354 | A1 | 10/2019 | Xu et al. | |
| 2019/0350520 | A1 | 11/2019 | Bailey et al. | |
| 2020/0253583 | A1 | 8/2020 | Brisken et al. | |
| 2021/0001116 | A1 * | 1/2021 | Waldhauser | A61B 5/6858 |
| 2021/0169443 | A1 * | 6/2021 | Shurtliff | A61B 5/6824 |
| 2021/0401579 | A1 | 12/2021 | Grossi et al. | |
| 2022/0031181 | A1 * | 2/2022 | Tavakoli | G16H 40/67 |

OTHER PUBLICATIONS

Wang F., et al., "Flexible Doppler Ultrasound Device for the Monitoring of Blood Flow Velocity", Science Advances, Oct. 27, 2021, Retrieved on Apr. 29, 2023, vol. 7, No. 44, 11 Pages.
Supplementary European Search Report in European Patent Application No. 23775618.4, dated Feb. 9, 2026, 10 Pages.

* cited by examiner

IN VIVO FLUID FLOW SENSOR

CROSS-REFERENCE TO RELATED APPLICATIONS

Any and all applications for which a foreign or domestic priority claim is identified in the Application Data Sheet as filed with the present application are hereby incorporated by reference.

TECHNICAL FIELD

This present disclosure relates to sensors deployable in the body of a patient user for monitoring fluid flow and biological function in vivo.

BACKGROUND

According to the World Health Organization (WHO), cardiovascular diseases are among the leading causes of death globally, resulting in an estimated 17.9 million lives lost each year. In the United States, heart disease is the leading cause of death, with coronary artery disease (CAD) being the most pernicious class by causing decreased blood flow to the heart that often leads to a heart attack. CAD and other heart valve diseases, like mitral valve prolapse (MVP) and mitral valve regurgitation (MVR), are silent killers because persons typically do not know the existence of their underlying heart problems and therefore are not diagnosed until the person experiences signs or symptoms of a heart attack, heart failure, or an arrhythmia-which may be too late to survive or recover with a reasonable quality of life. Even now, a person must typically have a secondary medical condition, such as diabetes or obesity, or be identified with one or more significant risk factors, such as high blood pressure, high cholesterol, high alcohol use, or smoking, for the physician to initiate a round of testing and remote monitoring of the person's heart. This is because there is not an accessible, uncomplicated, and affordable device or technique to observe and track a person's heart function.

Presently, examination of heart function to potentially diagnose heart disease is limited to the clinical environment. Typically, a patient would undergo a variety of different tests, including analyte testing from blood samples; imaging such as a chest X-ray, CT-scan, or magnetic resonance imaging (MRI) of the heart; and physiological signal monitoring, such as an electrocardiogram (ECG or EKG), which are electrical signal recordings of the heart that can indicate heart rate and detect irregular heartbeats when monitored remotely (e.g., by a Holter monitor), or an echocardiogram, which is a noninvasive acoustic (sound) signal monitoring technique used to create images of the heart and blood in motion. Moreover, patients are only prescribed such tests after experiencing an acute or emergency medical treatment, such as cardiac arrest, stroke, severe dizziness or unconsciousness, or extreme chest pain.

To date, there have been some advancements in remote monitoring to begin turning the tide against heart disease. For instance, wearable heart rate monitors are becoming a ubiquitous option for tracking heart rate during exercise or daily activity, monitoring stress and movement levels, tracking sleep habits at night, and in some versions of these wearable devices, testing certain vital signs outside of the clinic, such as ECG to determine singular heart rhythm events, such as a healthy sinus rhythm or risky atrial fibrillation. While these devices are well suited to promote healthier active lifestyles that may contribute to preventing the onset of heart disease or mitigating minor-to-moderate heart disease in the long run, they are ill equipped to identify symptoms or hallmarks of the vast array of heart diseases and incapable of determining any underlying biological or physiological factors at the root of heart disease.

The challenge for clinicians is to catch heart disease early or manage and monitor diagnosed heart disease post-treatment. Yet, monitoring heart function relies on patient participation and compliance; and existing systems and methods are too time intensive, costly, and under-resourced to be effective.

There is a need for a new paradigm of sensors deployable in the body of a patient user and capable of monitoring the dynamic flow of biological fluids in vivo, such as blood flow across a valve of the heart, to characterize overall heart function.

BRIEF SUMMARY

In brief, disclosed are devices, systems, and methods for in vivo monitoring of the flow of a biological fluid in an anatomic structure, such as blood flow across a heart valve or blood flow through a heart chamber.

In some embodiments, a sensor device for in vivo monitoring of fluid flow in an anatomic structure includes a linkage assembly comprising a first arm configured to attach to a first portion of the anatomic structure and a second arm configured to attach to a second portion of the anatomic structure opposite to the first portion; a connection apparatus coupled to each of the first arm and the second arm; an ultrasound sensor assembly comprising a plurality of acoustic transducer elements coupled to the linkage assembly, the plurality of acoustic transducer elements including a first acoustic transducer element that is configured to transmit an acoustic signal to propagate through the anatomic structure and a second acoustic transducer element and a third acoustic transducer element that are configured to receive acoustic signals that have propagated through the anatomic structure and are indicative of a fluid flow parameter of a biological fluid in the anatomic structure; and an electronics unit housed in the connection apparatus and in electrical communication with the plurality of acoustic transducer elements of the ultrasound sensor assembly, the electronics unit configured to process electrical signals associated with the received acoustic signals as data and wirelessly transmit the data to an external processor.

In some embodiments, a sensor device for in vivo monitoring of blood flow in a heart or blood vessel leading into or out of the heart in a body of a patient, includes, a linkage assembly comprising a first arm configured to attach to a first portion of the heart or the blood vessel and a second arm configured to attach to a second portion of the heart or the blood vessel; a connection apparatus coupled to each of the first arm and the second arm; an ultrasound sensor assembly comprising a plurality of acoustic transducer elements coupled to the linkage assembly, the plurality of acoustic transducer elements including a first acoustic transducer element that is configured to transmit an acoustic signal to propagate through the heart or the blood vessel and a second acoustic transducer element and a third acoustic transducer element that are configured to receive acoustic signals that have propagated through the heart or the blood vessel and are indicative of a fluid flow parameter of the blood that flows in the heart or blood vessel; and an electronics unit housed in the connection apparatus and in electrical communication with the plurality of acoustic transducer elements of the ultrasound sensor assembly, the electronics unit configured to process electrical signals associated with the received acoustic signals as data and wirelessly transmit the data to an external processor, wherein the linkage assembly includes a clip band operable to provide a compression force by each of the first arm and the second arm of the clip band to facilitate securement of the sensor device to the first portion and the second portion of the heart or the blood vessel and to absorb forces applied onto the first arm and the second arm of the clip band by heartbeats or changes in size of the heart or the blood vessel.

In some embodiments, a system for in vivo monitoring of fluid flow in an anatomic structure includes an in vivo sensor device operable to be deployed in a body of a patient user and attached to the anatomic structure, and a data processing system in data communication with the in vivo sensor device. The in vivo sensor device includes a linkage assembly comprising a first arm configured to attach to a first portion of the anatomic structure and a second arm configured to attach to a second portion of the anatomic structure opposite to the first portion; a connection apparatus coupled to each of the first arm and the second arm; an ultrasound sensor assembly comprising a plurality of acoustic transducer elements coupled to the linkage assembly, the plurality of acoustic transducer elements including a first acoustic transducer element that is configured to transmit an acoustic signal to propagate through the anatomic structure and a second acoustic transducer element and a third acoustic transducer element that are configured to receive acoustic signals that have propagated through the anatomic structure and are indicative of a fluid flow parameter of a biological fluid in the anatomic structure; and an electronics unit housed in the connection apparatus and in electrical communication with the plurality of acoustic transducer elements of the ultrasound sensor assembly, the electronics unit configured to process electrical signals associated with the received acoustic signals as data and wirelessly transmit the data to an external processor. The data processing system includes a processor and a memory and is configured to receive the data from the in vivo sensor device and process the received data to determine the fluid flow parameter associated with the biological fluid in the anatomic structure.

In some embodiments, a sensor device for in vivo monitoring of a cardiac function includes a linkage assembly comprising a first arm configured to attach to a first external portion of a heart, and an optional second arm that may be configured to attach to a second external portion of the heart; a housing coupled to the linkage assembly; a sensor assembly coupled to the first arm and configured to detect a functional parameter of the heart; and an electronics unit disposed in the housing and in electrical communication with the sensor assembly, the electronics unit configured to process electrical signals associated with the detected functional parameter as data and wirelessly transmit the data to an external processor.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

Many aspects of the present disclosure can be better understood with reference to the following drawings. The features in the drawings are not necessarily to scale, fully shown, or depicted in the same manner as would be physically constructed. Instead, emphasis is placed on clearly illustrating the principles of the present disclosure. The drawings should not be taken to limit the disclosure to the specific embodiments depicted but are for explanation and understanding only.

DETAILED DESCRIPTION

Figure 1A:
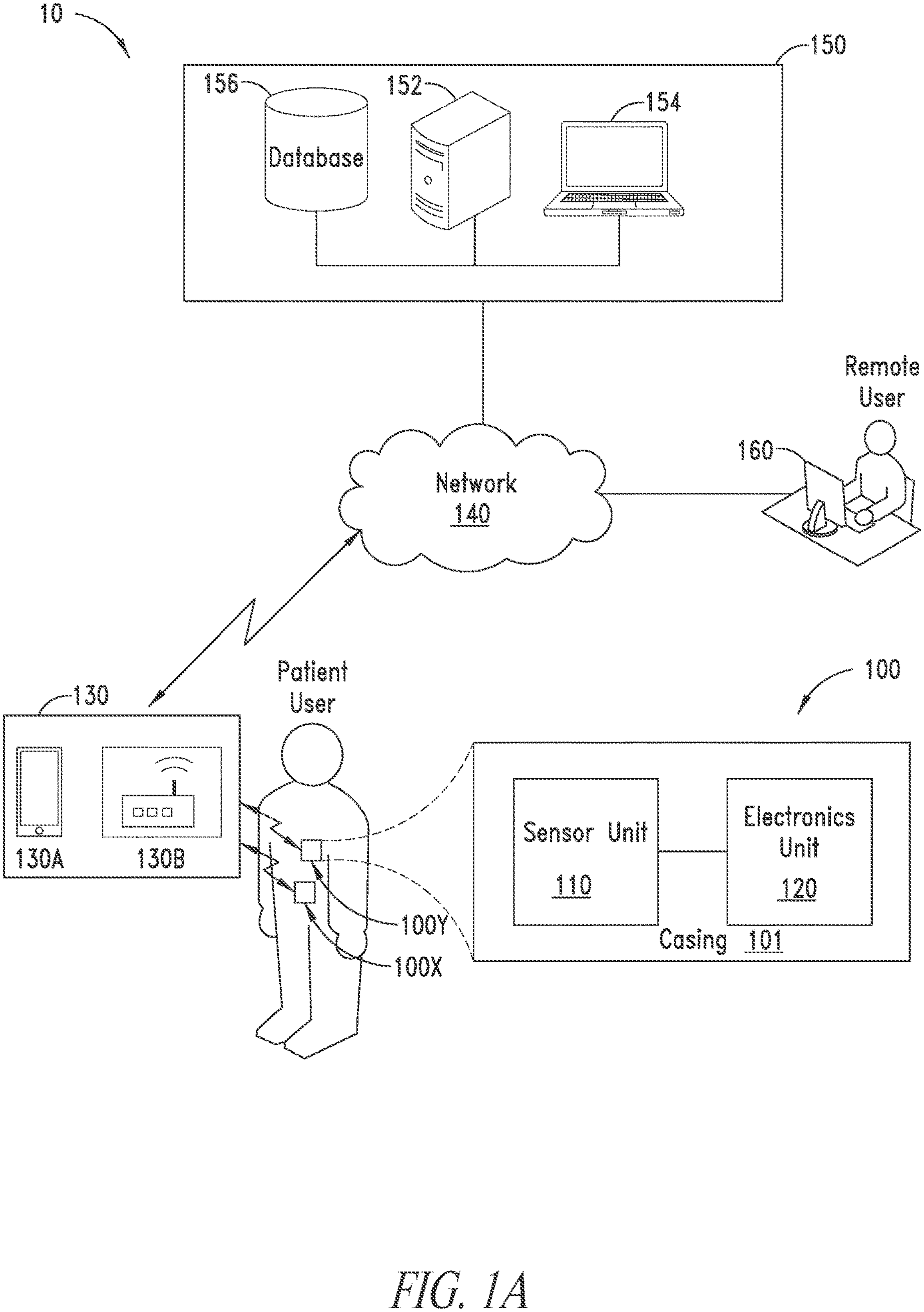
FIG. 1A shows a diagram illustrating an example embodiment of a system for in vivo monitoring of flow for a biological fluid, in accordance with the present technology.

Disclosed are devices, systems, and methods for in vivo monitoring of the flow of a biological fluid in an anatomic structure, such as blood flow through a heart valve (e.g., mitral valve, tricuspid valve, and/or aortic valve) or blood flow through a heart chamber, e.g., an atrium or ventricle, or a major blood vessel into or out of the heart, e.g., the aorta, vena cava, or pulmonary veins or arteries. The disclosed devices, systems, and methods can continuously measure and evaluate blood flow forward and backward at a region of the heart (e.g., an inlet or outlet of a heart valve) for determination of heart function or dysfunction (e.g., such as mitral valve regurgitation (MVR)) and/or in compilation with other monitored data that can be used to measure or predict secondary factors (e.g., such as heart rate (HR), cardiac output (CO), or hallmarks of congestive heart failure (CHF)).

Implementations of the disclosed technology are envisioned to shift the present paradigm from disparate acute or emergency medical treatments to remote and continuous monitoring and management for long-term diagnostic and predictive care. For example, acute management of a treatment site in the heart is presently left undetectable after treatment (e.g., implantation of stent, implant (such as a mitral annuloplasty, a mitral valve, a percutaneous mitral valve), pacemaker, etc.), unless a severe functional issue is "felt" by the patient that causes the patient to revisit the health provider, which in many cases is in an emergency situation. An in vivo fluid flow sensor device of the disclosed in vivo fluid flow sensor platform can be implanted directly on the periphery of the heart (and in a manner agnostic to any existing biomedical device implanted in the heart) to detect blood flow in the heart indicative of potential disparities, including, for example, cardiac output, stroke volume, total peripheral resistance, and/or development of restenosis.

For example, in some implementations, the disclosed in vivo fluid flow sensor device can measure fluid flow through the atrium chamber to the ventricle chamber of the heart, e.g., determine blood flow at the mitral valve for the left heart side or the tricuspid valve on the right side, and thereby determine fluid flow for a valve capacity known as "valve flow capacity" with measurement of the "Q", i.e., flow rate (volume of blood/time) or the amount of pressure difference between the ends of the flow path divided by the resistance), which can be used for characterizing regurgitation of natural fluid blood flow, potential leaking by the valve, and back disruption flow. The disclosed in vivo fluid flow sensor devices, when placed proximate a heart valve, are able to detect where the valve dysfunction (e.g., leaking) is occurring, e.g., once placed in position and properly calibrated. Implementations of the disclosed in vivo fluid flow sensor platform (i.e., devices, systems, and/or techniques) can also be able to detect the diameter of the heart chamber or predictive area and/or predictive volume, as well as changes to a baseline measurement over time, which can indicate potential detrimental effects of heart function/performance with respect to that baseline and/or degradation of post treatment (e.g., that could lead to heart disease, such as Congestive Heart Failure (CHF), which is a chronic condition where the heart cannot pump blood as well as it should often due to weak or stiff tissue of the heart). For example, blood flow and regurgitation detection across the heart valve(s) can be used for correlation to heart function/performance and the effect of heart failure, as defined by CHF.

Also, for example, the data obtained by embodiments of the disclosed fluid flow sensor technology can be used in compilation with information to enable or optimize management of pharmaceutical prescription medication (e.g., dosage) for optimum patient care. For example, the data obtained by embodiments of the disclosed fluid flow sensor technology can be used for assessing valvular function and function degradation, as well as can be used in valvular treatment or vascular treatment (e.g., in compilation with EKG data). As an illustrative example, the disclosed in vivo fluid flow sensor platform can position an in vivo fluid flow sensor device on a vena cava and apply ultrasound signals to obtain information (e.g., dimensions of the vessel (thickness) and velocity of blood flow through the vena cava) that can be used to determine pulmonary wedge pressure, and thereby monitor the efficacy of certain medication doses in treating a patient with various forms of heart disease. Moreover, for patients with heart disease taking a cocktail of medications for managing their heart condition (e.g., diuretics for fluid volume, ace inhibitors for peripheral resistance, and beta blockers for contractility), blood pressure and flow through the vena cava can indicate whether the patient is properly complying with the medication regimen or the regimen is not optimal or effective, such as due to the body developing resistance to the drugs over time.

The disclosed in vivo fluid flow sensor platform offers the capability of obtaining acoustic signal measurements of fluid flow directly through an anatomic structure (and without other anatomic structures in the acoustic signal pathway) and providing the obtained acoustic signal measurements to a remote device (e.g., such as a remote in vivo device in communication with the in vivo fluid flow sensor device and/or a remote device external to the body in communication with the in vivo fluid flow sensor device and/or the remote in vivo device), while also able to perform such functions with low power requirements and in a relatively small physical footprint (i.e., device volume) for long durations of time (e.g., years to over a decade).

While disclosed embodiments of an in vivo sensor are described herein primarily based on monitoring of the blood flow across a heart structure (such as a heart valve) within a patient's body to facilitate understanding of the underlying concepts of the present technology, it is understood that the disclosed embodiments in accordance with the present technology can also include monitoring the dynamic flow of other biological fluids and other systems, including but not limited to fluid flow in the gastrointestinal system, renal system, or other.

In some embodiments, for example, a sensor device for in vivo monitoring of fluid flow in an anatomic structure while coupled to the anatomic structure, such as an atrium, ventricle, valve therebetween, or major blood vessel of the heart, includes a linkage assembly comprising a first arm configured to attach to a first portion of the anatomic structure and a second arm configured to attach to a second portion of the anatomic structure opposite to the first portion; a connection apparatus coupled to each of the first arm and the second arm; an ultrasound sensor assembly comprising a plurality of acoustic transducer elements coupled to the linkage assembly, the plurality of acoustic transducer elements including a first acoustic transducer element that is configured to transmit an acoustic signal to propagate through the anatomic structure and a second acoustic transducer element and a third acoustic transducer element that are configured to receive acoustic signals that have propagated through the anatomic structure and are indicative of a fluid flow parameter of a biological fluid in the anatomic structure; and an electronics unit housed in the connection apparatus and in electrical communication with the plurality of acoustic transducer elements of the ultrasound sensor assembly, the electronics unit configured to process electrical signals associated with the received acoustic signals as data and wirelessly transmit the data to an external processor.

In some embodiments, for example, a sensor device for in vivo monitoring of fluid flow in an anatomic structure while coupled to the anatomic structure, such as monitoring blood flow in an atrium, ventricle, valve therebetween, or major blood vessel of the heart, includes a first ultrasound assembly comprising a first set of one or more acoustic transducer elements; a second ultrasound assembly comprising a second set of one or more acoustic transducer elements; a first linkage coupled to the first ultrasound assembly; a second linkage coupled to the second ultrasound assembly; an electronics unit in electrical communication with the first ultrasound assembly and the second ultrasound assembly, the electronics unit configured to process the electrical signals associated with the returned acoustic signals as data and wirelessly transmit the data to an external processor; and a spring connection apparatus that couples to each of the first and second linkages and is operable to position the first ultrasound assembly at a first location on the anatomic structure and position the second ultrasound assembly at a second location on the anatomic structure to form a plane across the first and second locations of the anatomic structure to transmit and receive acoustic signals from the first set of one or more acoustic transducer elements and the second set of one or more acoustic transducer elements indicative of a fluid flow parameter of a biological fluid in the anatomic structure.

These and other embodiments are discussed in greater detail by the examples below.

EXAMPLE EMBODIMENTS

FIG. 1A shows a diagram illustrating an example embodiment of a system 10 for in vivo monitoring of fluid flow in a patient user, in accordance with the present technology. The system 10 includes one or more in vivo fluid flow sensor devices 100 that can be implanted within the patient user and a data processing system 150 in communication with the one or more in vivo fluid flow sensor devices 100. In some embodiments, the system 10 includes a receiver device 130 operable to receive a wireless transmission carrying data indicative of detected signals acquired from the one or more in vivo fluid flow sensor devices 100 and to transmit and/or store the data to the data processing system 150. In some embodiments, the one or more in vivo fluid flow sensor devices 100 and/or the receiver device 130 is/are in communication with the data processing system 150 via a network 140 of computers in communication with each other and accessible through the Internet (e.g., referred to as the cloud), where the data from the one or more in vivo fluid flow sensor devices 100 and/or the receiver device 130 can be transferred to the data processing system 150. Similarly, information from the data processing system 150 can be transferred to the receiver device 130 and/or the one or more in vivo fluid flow sensor devices 100.

In an example embodiment, the in vivo fluid flow sensor device 100 includes a sensor unit 110 and an electronics unit 120, which one or both of the sensor unit 110 and the electronics unit 120 are housed in and/or coupled via a housing or casing 101. In some examples, the housing or casing 101 is configured to shield components of the electronics unit 120 from fluids or substances of the body when the in vivo fluid flow sensor device 100 is deployed inside the patient user.

In the example of the system 10 illustrated in FIG. 1A, the one or more in vivo fluid flow sensor devices 100 includes a first in vivo fluid flow sensor device 100Y deployed in a first portion of the patient user's body, e.g., the chest, head, torso, an appendage, or other area; and the one or more in vivo fluid flow sensor devices 100 includes a second in vivo fluid flow sensor device 100X deployed in a second portion of the patient user's body. One or both of the first and/or second in vivo fluid flow sensor device 100Y and/or 100X, respectively, may be directly coupled to an organ or tissue within the patient's body at the first portion and/or second portion, respectively. In some implementations, for example, the first in vivo fluid flow sensor device 100Y may be coupled to an implant device deployed at or near the first portion in the patient user's body, such as an implant for the heart, lung, cranium, neck, intestines and digestive track, limb or extremity, etc. Similarly, for example, the second in vivo fluid flow sensor device 100X may be coupled to a second implant device deployed at or near the second portion in the patient user's body.

In some example embodiments, such as those discussed later in connection with FIG. 1B, the sensor unit 110 includes at least one of a first ultrasound sensor assembly and a second ultrasound sensor assembly each including one or more acoustic transducer elements, which are configured to be positioned across and in contact with an anatomic structure, such as the heart, and electrically connected to the electronics unit 120 (e.g., housed in the casing 101), such that one or both of the first and second ultrasound sensor assemblies transmit and receive acoustic signals across a region of interest of the anatomic structure and the electronics unit 120 processes and/or relays the data associated with the monitored acoustic signals to the receiver device 130. The one or more acoustic transducer elements of the first and second ultrasound sensor assemblies of the sensor unit 110 are electrically coupled to the electronics unit 120, e.g., via electrical interconnections such as wires, to provide electrical signals to stimulate transmission of the acoustic transmit signals across the region of interest and to receive electrical signals transduced from received acoustic signals propagating across the region of interest of the anatomic structure. Further details of the sensor unit 110 and the electronics unit 120 for some embodiments of the in vivo fluid flow sensor device 100 are discussed in FIG. 1B and other figures.

Referring to FIG. 1A, in some implementations, the one or more in vivo fluid flow sensor devices 100 wirelessly communicate the acquired data obtained directly to the receiver device 130. For example, the one or more in vivo fluid flow sensor devices 100 can transfer the data to the receiver device 130 using a low power wireless communication protocol, e.g., such as Bluetooth Low Energy (BLE), Near Field Communication (NFC), low frequency radio frequency (RF) signal in a range of 3 kHz to 1.3 MHz, or other. Example embodiments of the receiver device 130 include a computing device 130A or a dedicated base station 130B. For example, the computing device 130A can include, but is not limited to, a smartphone, tablet, a home device (e.g., Alexa, Nest, Echo, Google Home, Smart TVs, etc.), a wearable computing device (e.g., smartwatch, smart-glasses or headgear, etc.), a laptop or desktop computer, or other. The dedicated base station 130B can include data storage and/or data communication units that facilitate the communication of data from the one or more in vivo fluid flow sensor devices 100 to the data processing system 150 through a Wi-Fi access or cellular link to the network 140. In some implementations, for example, the receiver device 130 can be embodied on multiple receiver devices, such both the computing device 130A (e.g., smartphone, tablet, etc.) and the dedicated base station 130B, as illustrated in the example of FIG. 1A. In some implementations, for example, the receiver device 130 can (i) process, at least partially, the received data for display on a display screen of the receiver device 130 and/or for transfer of the received data to an external computer or computing system, such as the data processing system 150. In some embodiments, for example, the system 10 optionally includes a software application ("app") that is resident on the receiver device 130 to control various data processing, storage, and communication functionalities for management of the received data.

In the example of the system 10 illustrated in FIG. 1A, the data processing system 150 can include one or more server computer devices 152, one or more client computer devices 154, and/or one or more databases 156, in data communication with each other. In implementations, for example, the computer device(s) 152, 154 and the database(s) 156 are in communication with each other and/or in communication with the other devices of the system 10 via the network 140. In some implementations, for example, the data processing system 150 can remotely monitor data associated with the patient user obtained by the one or more in vivo fluid flow sensor devices 100 and/or remotely operate aspects of the system 10, e.g., such as modify sensing parameters or protocols of the one or more in vivo fluid flow sensor devices 100, data display or processing features of the app on the receiver device 130, or other.

In some embodiments, for example, the system 10 optionally includes a remote computing device 160 operated by a remote user to remotely monitor data associated with the patient user obtained by the one or more in vivo fluid flow sensor devices 100 that is transferred to the data processing system 150. For example, the remote computer 160 can include a personal computer such as a desktop or laptop computer, a mobile computing device such as a smartphone, tablet, smartwatch, etc., or other computing device. In some implementations, for example, the remote computing device 160 is configured to only receive data that is curated (e.g., selected, pre-processed, and/or formatted) by the data processing system 150. In some implementations, for example, the remote computing device 160 is configured to remotely operate one or more aspects (e.g., functionalities) of the system 10. For example, the remote computing device 160 can implement a remote user software application (remote user app) that is configured to provide the remote user with such display, storage, and/or management features. The remote user, for example, can include a health care provider (HCP), such as a physician, nurse, family member of the patient user, or other caregiver, or a medical insurance payer, or other type of stakeholder entity or individual with respect to the patient user's health.

Figure 1B:
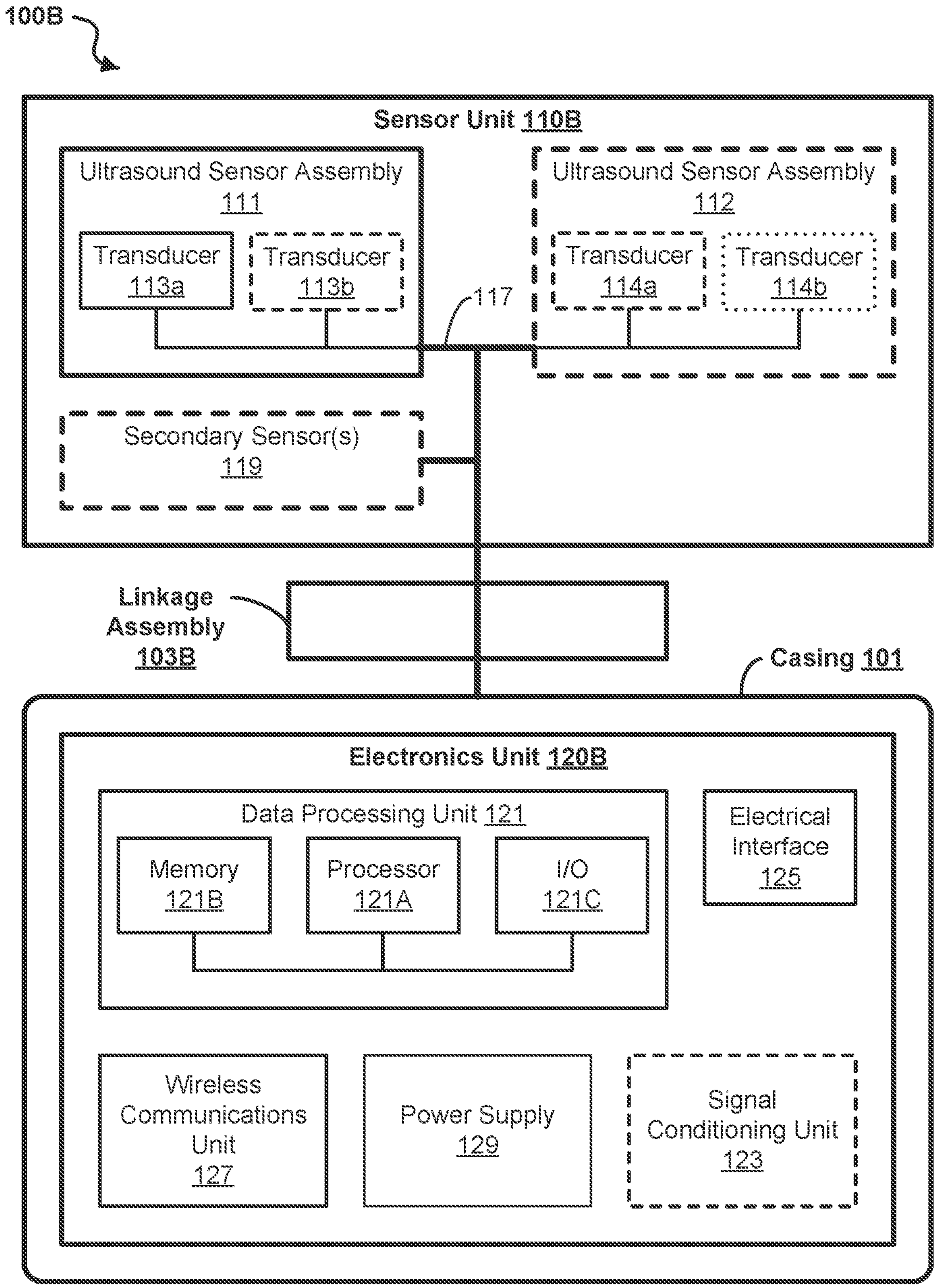
FIG. 1B shows a block diagram illustrating an example embodiment of an in vivo fluid flow sensor device of FIG. 1A, in accordance with the present technology.

FIG. 1B shows a block diagram illustrating an example embodiment of the in vivo fluid flow sensor 100 shown in FIG. 1A, which is shown in FIG. 1B as in vivo fluid flow sensor 100B. In the example of FIG. 1B, the in vivo fluid flow sensor 100B includes an example embodiment of a sensor unit 110 (shown as sensor unit 110B) and an example embodiment of electronics unit 120 (shown as electronics unit 120B). The sensor unit 110B of the in vivo fluid flow sensor 100B includes at least one ultrasound assembly in electrical communication with the electronics unit 120 via electrical interconnection(s) 117, which is depicted in FIG. 1B as having a first ultrasound sensor assembly 111 and an optional second ultrasound sensor assembly 112, each in electrical communication with the electronics unit 120 via the electrical interconnection(s) 117. The first ultrasound sensor assembly 111 includes one or more acoustic transducer element(s) 113 (also referred to herein as "transducer 113" or "one or more transducers 113"); and the optional second ultrasound sensor assembly 112 includes one or more acoustic transducer element(s) 114 (also referred to herein as "transducer 114" or "one or more transducers 114"). The one or more transducers 113 of the first ultrasound sensor assembly 111 includes a transducer element 113*a* and may optionally include an additional transducer element or elements, represented in FIG. 1B as transducer element(s) 113*b*. Similarly, the one or more transducers 114 of the optional second ultrasound sensor assembly 112 includes a transducer element 114*a* and may optionally include an additional transducer element or elements, represented in FIG. 1B as transducer element(s) 114*b*. For example, embodiments with multiple acoustic transducer elements can be configured as an array of transducers of the respective ultrasound sensor assembly. The electrical interconnection(s) 117 are configured to couple each of the one or more acoustic transducer element(s) 113 of the first ultrasound sensor assembly 111 and the one or more acoustic transducer element(s) 114 of the optional second ultrasound sensor assembly 112 to an electrical interface of the electronics unit 120B. In various implementations of example embodiments of the in vivo fluid flow sensor 100B, the first ultrasound sensor assembly 111 and the optional second ultrasound sensor assembly 112 may transmit and receive acoustic signals at one or more frequencies within a frequency range of 2 MHz to 20 MHz. In various embodiments, for example, the first ultrasound sensor assembly 111 and the optional second ultrasound sensor assembly 112 each may include a frame, casing or housing structure (not shown) to structurally support the one or more acoustic transducer element(s) 113 and the one or more acoustic transducer element(s) 114, respectively, and position them in a fixed location with respect to each other.

In some embodiments, for example, the transducer element or elements of the one or more acoustic transducer element(s) 113 and the one or more acoustic transducer element(s) 114 include a piezoelectric transducer operable to transmit acoustic signals based on an electrical input signal and receive acoustic signals to produce an electrical output signal. For example, the piezoelectric transducer can include a solid piezoelectric ultrasound transducer or a piezoelectric micromachined ultrasonic transducer (PMUT), e.g., a MEMS-based piezoelectric ultrasonic transducers for acoustic imaging of the environment. In some embodiments, for example, the transducer element or elements of the one or more acoustic transducer element(s) 113 and the one or more acoustic transducer element(s) 114 include a ferroelectric hafnium oxide transducer.

The in vivo fluid flow sensor device 100B includes a linkage assembly 103B that couples the first ultrasound sensor assembly 111 to the electronics unit 120B (and, in embodiments including the second ultrasound sensor assembly 112, couples the second ultrasound sensor assembly 112 to the electronics unit 120B). In some embodiments, the linkage assembly 103B can include a pair of linkages that are configured to (1) secure (e.g., attach and anchor) the in vivo fluid flow sensor device 100B to the target in vivo organ or tissue and (2) carry the respective electrical interconnection(s) 117 (connected to the transducer(s) 113 and/or the transducer(s) 114) from the first ultrasound sensor assembly 111 and/or the optional second ultrasound sensor assembly 112 to the electronics unit 120B. In some embodiments, for example, the pair of linkages of the linkage assembly 103B include a spring connection apparatus, discussed later in connection with FIG. 2A. Whereas, in some embodiments, for example, the pair of linkages of the linkage assembly 103B include a flexible band, with or without a spring, as discussed later in this patent document.

In some embodiments of the in vivo fluid flow sensor device 100B, for example, the sensor unit 110B may optionally include one or more secondary sensor(s) 119. For instance, in some implementations, the secondary sensor(s) 119 may include an analyte sensor to measure a parameter (e.g., concentration) of an analyte in the region proximate the anatomic structure where the in vivo fluid flow sensor device 100B is deployed. In some examples, the optional secondary analyte sensor can include, but is not limited to, a glucose sensor. Additionally or alternatively to a secondary analyte sensor, the secondary sensor(s) 119 may include a pH sensor to measure the pH level in the region proximate the anatomic structure. Additionally or alternatively to a secondary analyte sensor and/or secondary pH sensor, the secondary sensor(s) 119 may include a temperature sensor to measure the temperature in the region proximate the anatomic structure. In such cases, for example, the optional one or more secondary sensor(s) 119 comprising the analyte sensor, the pH sensor, and/or the temperature sensor can be used to obtain data indicative of clinically-relevant conditions about the anatomic structure and/or conditions of the in vivo environment where the in vivo fluid flow sensor device 100B is deployed, such as a potential infection or inflammatory response to the implantation of the in vivo fluid flow sensor device 100B. In some embodiments, for example, the optional one or more secondary sensor(s) 119 can be attached to the casing 101 of the in vivo fluid flow sensor device 100B, e.g., via weld, chemical adhesion, clip, clamp, or other attachment means; and in some embodiments, for example, the optional one or more secondary sensor(s) 119 can be attached to one or both of the first ultrasound sensor assembly 111 and/or the (optional) second ultrasound sensor assembly 112, e.g., via attachment to the frame or casing structure.

In some embodiments, for example, the optional one or more secondary sensor(s) 119 of the in vivo fluid flow sensor device 100B can include an inertial measurement unit (IMU) that is configured to monitor motion of the in vivo fluid flow sensor device 100B in multiple degrees of freedom. In some embodiments, for example, the optional one or more secondary sensor(s) 119 of the in vivo fluid flow sensor device 100B can include an accelerometer in communication with the data processing unit 121 of the electronics unit 120B. In some embodiments, for example, the optional one or more secondary sensor(s) 119 of the in vivo fluid flow sensor device 100B can include a rate sensor in communication with the data processing unit 121 of the electronics unit 120B. In some embodiments, for example, the optional one or more secondary sensor(s) 119 of the in vivo fluid flow sensor device 100B can include a magnetometer in communication with the data processing unit 121 of the electronics unit 120B. In such implementations, for example, the in vivo fluid flow sensor device 100B is operable to measure heart rate in compilation with fluid flow through the heart (e.g., across the mitral valve or tricuspid valve) when the in vivo fluid flow sensor device 100B is deployed on the exterior of the heart, e.g., in the pericardium.

Also shown in the example of FIG. 1B, the electronics unit 120B of the in vivo fluid flow sensor device 100B includes a data processing unit 121, an optional signal conditioning unit 123, a power supply 129, a wireless communications unit 127, and an electrical interface 125, which can include electrically conductive contact sites (e.g., pads, pins, or other contact configuration) that electrically interfaces with the electrical interconnections 117 of the sensor unit 110B. The electronics unit 120B is configured to receive and at least partially process electrical signals acquired from the one or more acoustic transducer(s) 113 of the first ultrasound sensor assembly 111 and the one or more acoustic transducer(s) 114 of the second ultrasound sensor assembly 112 of the sensor unit 110B. For example, in some embodiments, the electrical signals are received at the corresponding contact sites of the electrical interface 125 and provided to the data processing unit 121 (or, optionally, first to the signal conditioning unit 123 to improve the quality of the acquired electrical signals from the sensor unit 110B prior to providing to the data processing unit 121). In such implementations, the output of the data processing unit 121 can include raw or processed data associated with the detected data from the sensor unit 110B, to be wirelessly transmitted to an external device by the wireless communications unit 127. In example embodiments of the electronics unit 120B, the power supply 129 can include a battery (e.g., primary or rechargeable), fuel cell or other power source to supply power to the components of the electronics unit 120B and/or the sensor unit 110B. In some implementations, for example, the power supply 129 includes an ultra-low power system (e.g., operating in the micro amp range).

In some optional embodiments, for example, the signal conditioning unit 123 can include a circuit including one or more filters and/or one or more amplifiers to augment the raw electrical signals detected by the ultrasound sensor assemblies 111, 112 of the sensor unit 110B to increase a signal-to-noise ratio (SNR) of the electrical signals, thereby producing data containing the signal-processed electrical signals. In some optional embodiments, the signal conditioning unit 123 can include drive circuitry to produce operating electrical signals that generate electrical potentials and/or currents at the optional analyte sensor electrode contingent(s) and/or temperature sensor contingent of the sensor unit 110B for operating an electrochemical sensing technique and/or electrophysiological or kinetic sensing technique to be performed at electrode(s) in implementations of the optional secondary sensor(s) 119 of the sensor unit 110B.

In some embodiments, for example, the wireless communications unit 127 includes a wireless transmitter, receiver, and/or transceiver device including an antenna, which is capable of communicating with an external device to communicate raw, partially-processed, or fully-processed data from the signal conditioning unit 123 (and/or the data processing unit 121, discussed below). For example, the wireless communications unit 127 can be configured to manage the communication protocol for transmission or reception via the antenna. Examples of antenna can include, but are not limited to, a whip antenna, a loop antenna, or a conformal antenna. An example transceiver unit can include a BLE chipset to communicate with a BLE-enabled device, e.g., a smartphone, tablet, or other external computing device, such as of the receiver device 130. Additionally or alternatively, in some embodiments, for example, the wireless communications unit 127 is configured as a scaffolding around the electronics unit 120B, e.g., such as coupled to or integrated with the casing 101, that is structured to provide wireless communication means for the in vivo fluid flow sensor device 100B.

In some embodiments, the electronics unit 120B includes a data processing unit 121 to at least partially process the conditioned electrical signals to (i) produce data, e.g., in an analog or a digital form, and/or (ii) control functionality of the electronics unit 120B and/or the sensor unit 110B. For example, the data processing unit 121 can be configured to manage data acquisition on data channels associated with the one or more acoustic transducers 113 and the one or more acoustic transducers 114 of the sensor unit 110B.

In some embodiments of the data processing unit 121, for example, the data processing unit 121 can include a processor 121A to process data and a memory 121B in communication with the processor 121A to store and/or buffer data. In various embodiments, for example, the processor 121A can include one or multiple processors, and the memory 121B can include one or multiple memory units. For example, the processor 121A can include a central processing unit (CPU), a microcontroller unit (MCU), a graphics processing unit (GPU), or other type of processor. For example, the memory 121B can include and store processor-executable code, which when executed by the processor, configures the data processing unit 121 to perform various operations, e.g., such as receiving information, commands, and/or data, processing information and data, and transmitting or providing information/data to another device. To support various functions of the data processing unit 121, the memory 121B can store information and data, such as instructions, software, values, images, and other data processed or referenced by the processor 121A. For example, various types of random access memory (RAM) devices, read only memory (ROM) devices, flash memory devices, and other suitable storage media can be used to implement storage functions of the memory 121B. In some embodiments, the data processing unit 121 includes an input/output (I/O) unit 121C to interface the processor 121A and/or memory 121B to other modules, units or devices, e.g., associated with an external device, such as the receiver device 130, the data processing system 150, the remote computing device 160, and/or other external devices. In some embodiments, the processor 121A, the memory 121B, and/or the I/O unit 121C is in communication with the wireless communications unit 127, e.g., such as a transmitter (Tx) or a transmitter/receiver (Tx/Rx) unit. For example, in such embodiments, the I/O unit 121C can interface the processor 121A and memory 121B with the wireless communications unit 127, e.g., to utilize various types of wireless interfaces compatible with typical data communication standards, which can be used in communications of the data processing unit 121 with other devices. The data communication standards include, but are not limited to, Bluetooth, Bluetooth Low Energy (BLE), Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G/6G cellular communication methods, and parallel interfaces. In some implementations, the data processing unit 121 can interface with other devices using a wired connection via the I/O unit 121C, e.g., such as prior to implantation within the patient user. The data processing unit 120B can also interface with other external interfaces, sources of data storage, and/or visual or audio display devices, etc. to retrieve and transfer data and information that can be processed by the processor 121A, stored in the memory 121B, or exhibited on an output unit of the receiver device 130 (e.g., smartphone, tablet, etc.) or other external device to the in vivo fluid flow sensor device 100.

In implementations of the in vivo fluid flow sensor device 100B, the first ultrasound sensor assembly 111 (and the optional second ultrasound sensor assembly 112) is/are controlled by the data processing unit 121 to transmit and receive acoustic signals. For example, in some implementations, the in vivo fluid flow sensor device 100B is configured to measure the Doppler shift of acoustic probe signals across the anatomic structure. For instance, the traveling time of the acoustic signals is indicative of an estimated distance of travel, and the frequency shift of a received acoustic signal is proportional to the velocity of the fluid flowing along the acoustic path. The data processing unit 121 is configured to provide a set of electrical control signals to the one or more transducers 113 and/or the one or more transducers 114 to stimulate transmission of acoustic probe signals across the region of interest, such as the mitral valve of the heart, such that the opposing set of transducers among the one or more transducers 113 and/or the one or more transducers 114 receives the fluid flow shifted acoustic probe signals; and based on the time of flight of the acoustic probe signals and known fixed positions of the one or more transducers 113 and the one or more transducers 114, the data processing unit 121 process the electrical signals transduced from the one or more transducers 113 and/or the one or more transducers 114 associated with the received acoustic probe signals to determine the fluid flow, e.g., forward flow or possible backward flow of blood across the mitral valve of the heart.

Figure 2A:
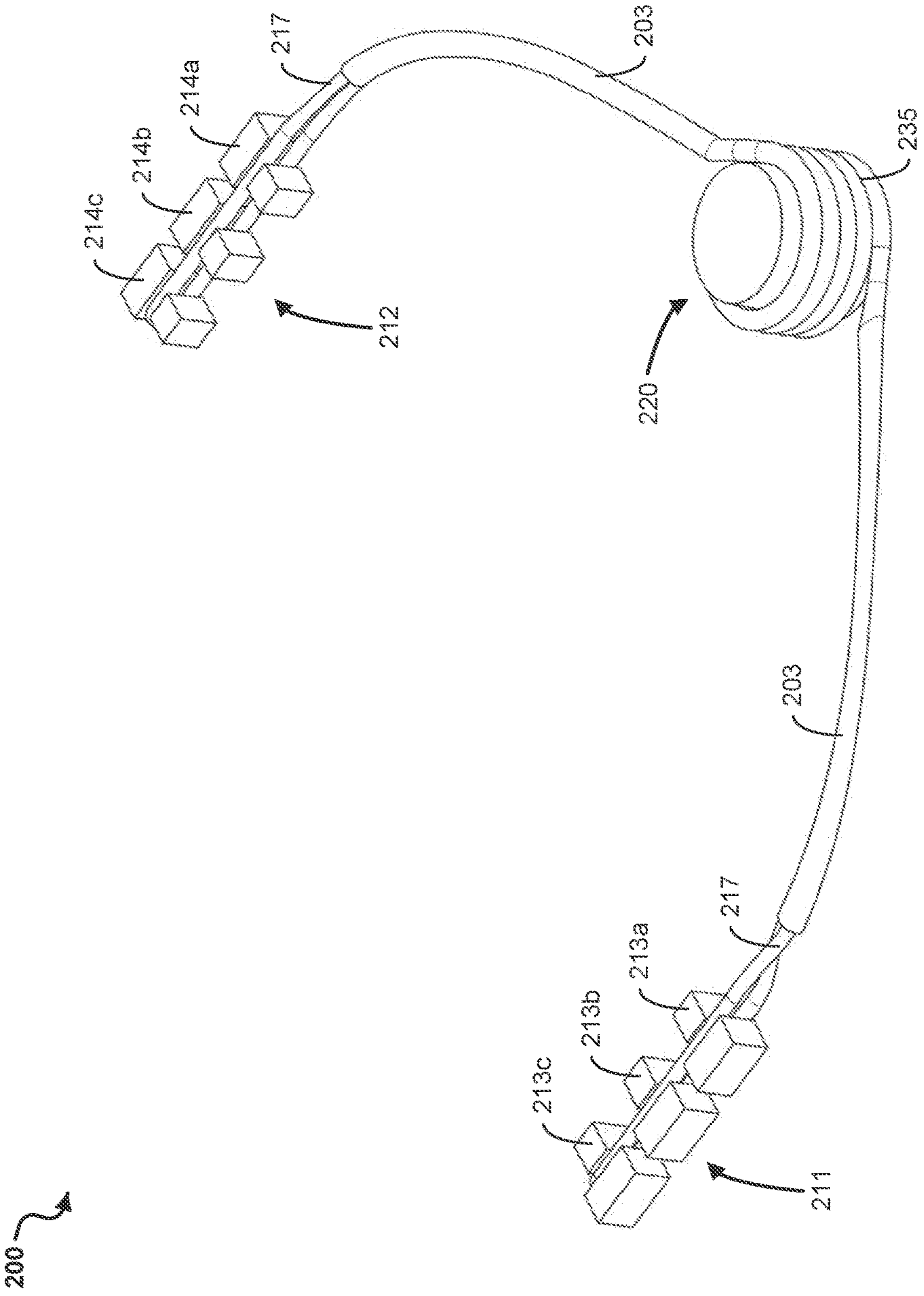
FIG. 2A shows a diagram depicting an example embodiment of the in vivo fluid flow sensor device of FIG. 1B, in accordance with the present technology.

FIG. 2A shows a diagram depicting an example embodiment of the in vivo fluid flow sensor device 100B of FIG. 1B, shown in FIG. 2A as in vivo fluid flow sensor device 200. The in vivo fluid flow sensor device 200 includes a sensor unit comprising an ultrasound sensor assembly 211 and an ultrasound sensor assembly 212 in electrical communication with an electronics unit 220 via electrical interconnections 217 (e.g., coupled to or partially housed within linkages, such as arms, of a linkage assembly 203). The ultrasound sensor assembly 211 includes a plurality of acoustic transducer elements 213, i.e., three acoustic transducer elements 213*a*, 213*b*, 213*c* in this example; and the ultrasound sensor assembly 212 includes a plurality of acoustic transducer elements 214, i.e., three acoustic transducer elements 213*a*, 213*b*, 213*c* in this example. It is understood that this embodiment is not limited to three acoustic transducer elements for each ultrasound sensor assembly and can include less or more than the configuration shown in the diagram of FIG. 2A, e.g., including but not limited to one or more acoustic transducer element for each of the ultrasound sensor assemblies 211 and 212. The ultrasound sensor assembly 211 and the ultrasound sensor assembly 212 include a frame, casing or housing structure (not shown) to secure the acoustic transducer elements 213 and the acoustic transducer elements 214, respectively, to the arms of the linkage assembly 203 and position them in a fixed location with respect to each other.

The electronic unit 220 of the in vivo fluid flow sensor device 200 is configured to be encased by a spring connection apparatus 235 that couples to each linkage of the linkage assembly 203. The spring connection apparatus 235 provides sufficient movement of the arms of the linkage assembly 203 to couple to the intended deployment location of the ultrasound sensor assembly 211 and the ultrasound sensor assembly 212, such as across a proximal and distal side of the left or right atrium of the heart, so that the force applied by the ultrasound sensor assembly 211 and the ultrasound sensor assembly 212 upon the anatomic structure (e.g., the heart) is sufficient to secure the in vivo fluid flow sensor device 200 while not interfering with the normal function of the anatomic structure of the intended application of the in vivo fluid flow sensor device 200. For example, the spring connection apparatus 235 includes a spring, which in addition to providing compression force upon the set of linkages of the linkage assembly 203 to transfer sufficient force to facilitate and/or maintain securement of the in vivo fluid flow sensor device 200 to the target portion of the heart (e.g., left or right atrium), the spring also allows provides adequate flexibility for the device 200 to be both stable in its placement while withstanding continuous movements (load cycling) of the anatomic structure to which its attached (e.g., heart beats) without suffering damage for hundreds of millions to billions of cycles-thereby giving significant longevity to the in vivo fluid flow sensor device 200 for decades of use (e.g., 50 to 60 million heart beats a year). Moreover, the set of linkages of the linkage assembly 203 are able to adjust in all three planes (x-y, x-z, y-z) to allow for initial proper alignment of the ultrasound sensor assemblies 211, 212.

In some embodiments, for example, the in vivo fluid flow sensor device 200 can secure to the anatomic structure by a prong, screw, barb, suture, adhesive (e.g., bioinert glue), or network of grasping mechanisms (not shown) disposed via the frame or casing of the ultrasound sensor assembly 211 and the ultrasound sensor assembly 212. In some embodiments of the in vivo fluid flow sensor device 200 (not shown in FIG. 2A), the frame, casing or housing structure can include one or more openings on each linkage of the linkage assembly 203 that can allow for secondary attachment means of the device 200 to the target anatomic structure, such as an opening with an anchor site to apply a suture connecting the linkage of the linkage assembly 203 to the anatomic structure (e.g., wall of the atrium of the heart). In some embodiments, the linkage assembly 203 can include materials that provide sufficient flexibility and rigidity to allow the in vivo fluid flow sensor device 200 to deploy on the anatomic structure without such detrimental interference. For example, in some embodiments, the linkage assembly 203 can include nitinol, platinum, MP35N, or other material or combination thereof. In some embodiments, the linkage assembly 203 provides a closure to lock-on to the heart, e.g., disallowing further movement of the linkages.

Figure 2B:
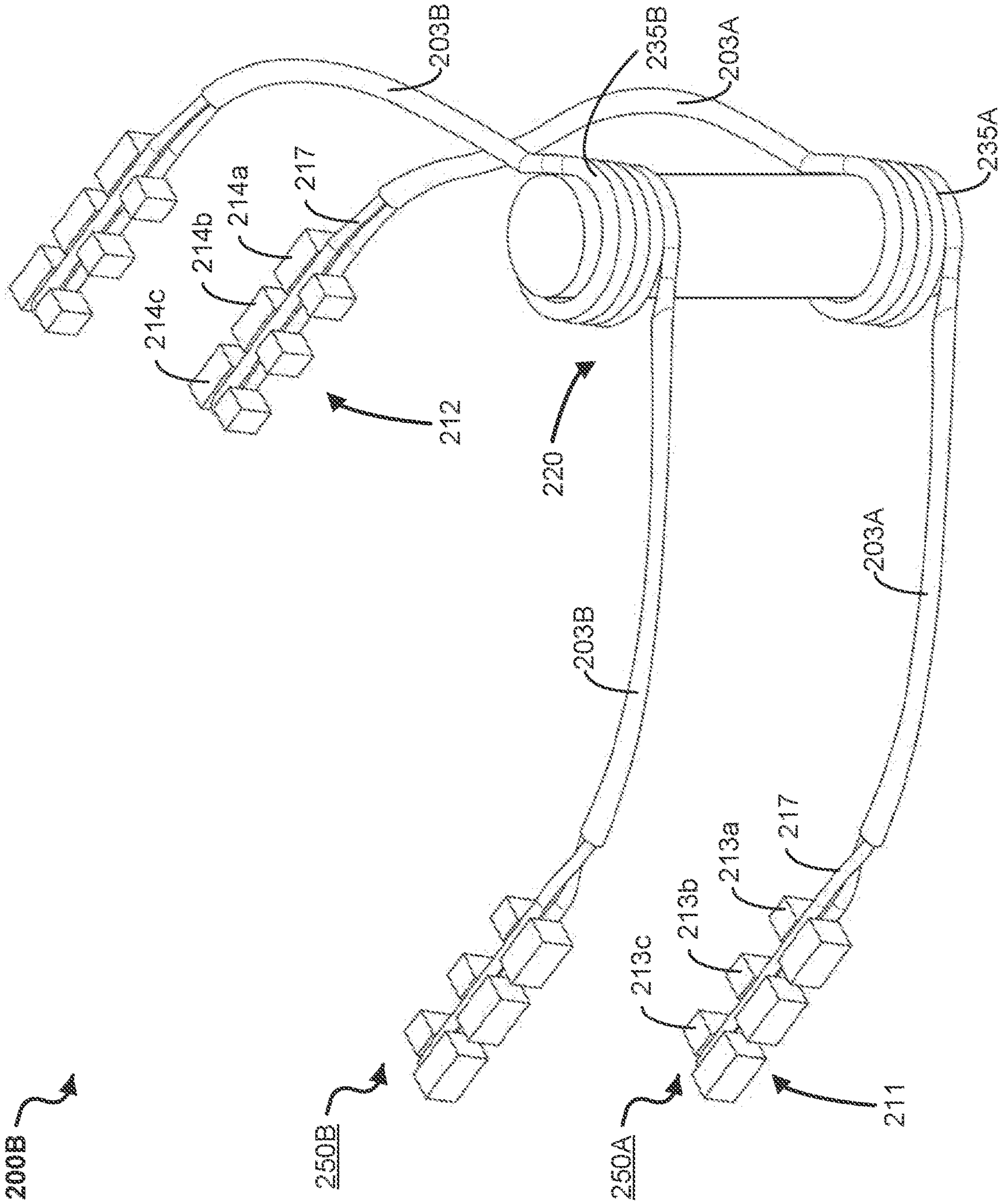
FIG. 2B shows a diagram depicting another example embodiment of the in vivo fluid flow sensor device of FIG. 1B including a second set of ultrasound sensor contingents, in accordance with the present technology.

FIG. 2B shows a diagram depicting another example embodiment of the in vivo fluid flow sensor device 100B of FIG. 1B, shown in FIG. 2B as in vivo fluid flow sensor device 200B. The in vivo fluid flow sensor device 200B includes a sensor unit comprising two or more sets of ultrasound sensor contingents 250 (shown in FIG. 2B as set 250A and 250B) in electrical communication with an electronics unit 220 via electrical interconnections 217 (e.g., coupled to or partially housed within sets of linkage assemblies 203A and 203B, respectively). Each set of the ultrasound sensor contingents 251 and 252 include the ultrasound sensor assembly 211 and the ultrasound sensor assembly 212 that comprise the plurality of acoustic transducer elements 213 and the plurality of acoustic transducer elements 214, respectively, such that multiple planes of acoustic signal propagation are measured at the region of interest of the anatomic structure (e.g., mitral valve of the heart). In this example, the electronics unit 220 is partially encased by two or more sets of spring connection apparatuses, shown by a spring connection apparatus 235B corresponding to the set of ultrasound sensor contingent 250B and by a spring connection apparatus 235A corresponding to the set of ultrasound sensor contingent 250A.

Figure 2C:
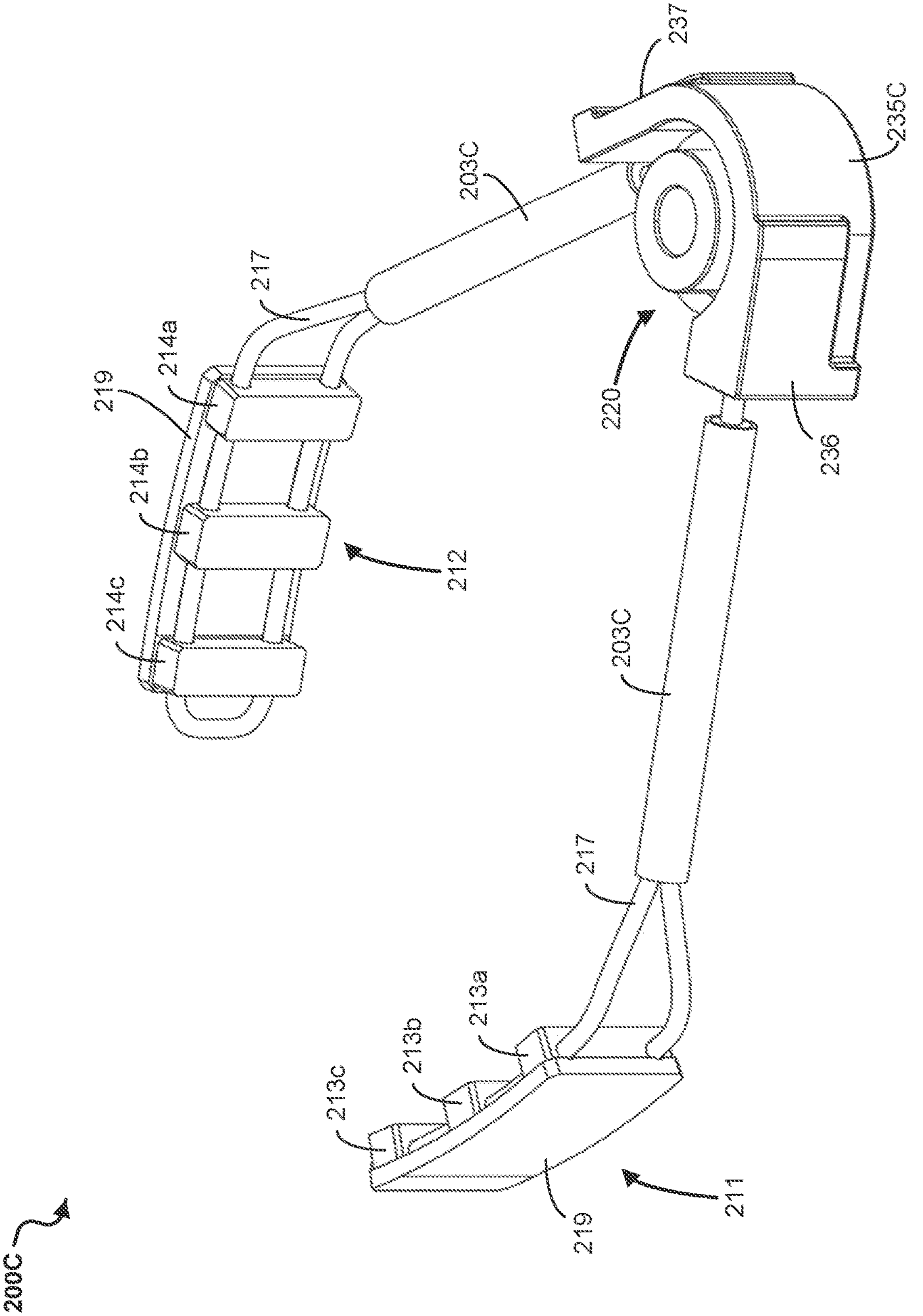
FIG. 2C shows a diagram depicting another example embodiment of the in vivo fluid flow sensor device of FIG. 1B, in accordance with the present technology.

FIG. 2C shows a diagram depicting another example embodiment of the in vivo fluid flow sensor device 100B of FIG. 1B, shown in FIG. 2C as in vivo fluid flow sensor device 200C. The in vivo fluid flow sensor device 200C can be configured similar to the in vivo fluid flow sensor device 200 (shown previously in FIG. 2A), e.g., where the sensor unit comprises the ultrasound sensor assembly 211 and the ultrasound sensor assembly 212 in electrical communication with an electronics unit 220 via the electrical interconnections 217 (e.g., coupled to or partially housed within linkages of the linkage assembly 203). Yet, in FIG. 2C, the electronic unit 220 of the in vivo fluid flow sensor device 200C is configured to be encased by a flex connection apparatus 235C that includes a first link 236 that is able to pivotably move with respect to a second link 237, and/or vice versa, to provide adequate flexibility for the device 200C to be both stable in its placement about the anatomic structure while withstanding continuous movements (load cycling) of the anatomic structure to which its attached (e.g., heart beats) without suffering damage for hundreds of millions to billions of cycles. In some embodiments, the flex connection apparatus 235 includes a spring. In some embodiments, the first link 236 is able to move within a cavity of the second link 237, and/or vice versa.

Also, the flex connection apparatus 235C couples the sensor unit 220 to each linkage of linkage assembly 203, shown in FIG. 2C as linkages 203C. Yet, in FIG. 2C, the linkage assembly 203C include a linear arm portion proximal to the flex connection apparatus 235C and a curved arm portion distal from the flex connection apparatus and proximate to the ultrasound sensor assembly 211 and the ultrasound sensor assembly 212. In this manner, for example, the structure of the in vivo fluid flow sensor device 200C is capable of attaching to a curved geometry for an anatomic structure, such as the left or right atrium of the heart, and provide sufficient compression force for attachment with adequate flexion to mitigate load cycling. In some embodiments, for example, one or both of the linkages 203C can be used to attach (optional) additional power supply (e.g., one or more batteries), which can be in electrical connection with the electronic unit and ultrasound sensor assemblies 211 and/or 212.

Furthermore, the ultrasound sensor assembly 211 and the ultrasound sensor assembly 212 include a frame, casing or housing structure 219 to secure the acoustic transducer elements 213 and the acoustic transducer elements 214, respectively, to the linkages of the linkage assembly 203C and position them in a fixed location with respect to each other. While not shown in FIG. 2C, the frame, casing or housing structure 219 can include one or more openings to allow for secondary attachment means of the device 200 to the target anatomic structure, such as an opening with an anchor site to apply a suture and secure the to the ultrasound sensor assembly 211 and the ultrasound sensor assembly 212 at the ends of the arms of the linkage assembly 203C to the anatomic structure (e.g., wall of the atrium of the heart). In some embodiments, like the example shown in FIG. 2C, the distal ends of the arms or linkages of the linkage assembly 203C of the in vivo fluid flow sensor device 200C are angled or curved inward, e.g., which can assist in facilitating attachment and conformation to the anatomic structure upon placement as well as aid in delivery of the device 200C, e.g., via a catheter.

While not shown in FIG. 2C, the sensor unit of the in vivo fluid flow sensor device 200C may include the two or more sets of ultrasound sensor contingents 250 (such as the configuration of ultrasound sensor contingents 250A and 250B as shown in FIG. 2B) in electrical communication with an electronics unit 220C via electrical interconnections 217 (e.g., coupled to or partially housed within respective arms of the linkage assembly 203C, respectively).

Figure 2D:
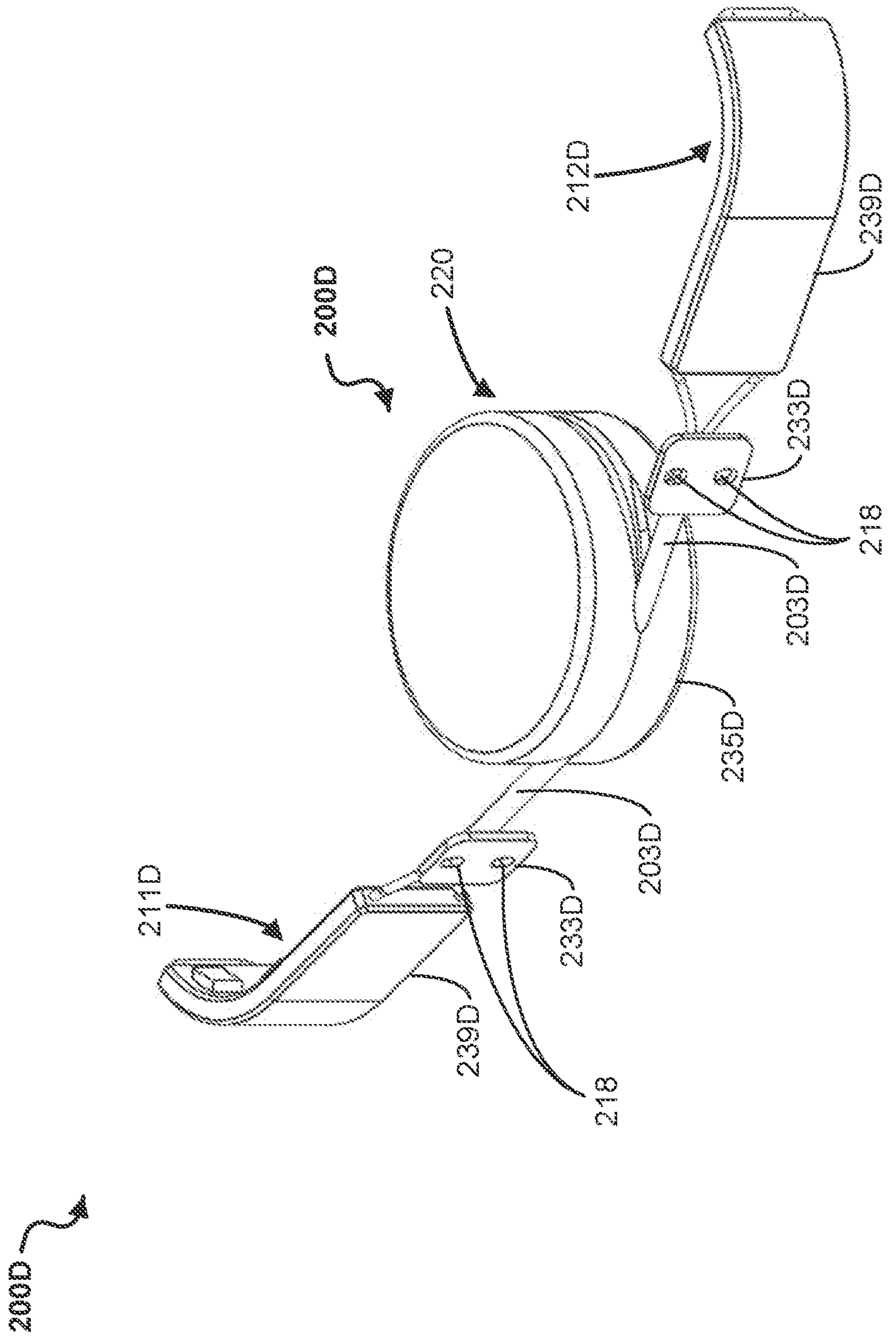
FIG. 2D shows a diagram depicting another example embodiment of the in vivo fluid flow sensor device of FIG. 1B, in accordance with the present technology.

FIG. 2D shows a diagram depicting another example embodiment of the in vivo fluid flow sensor device 100B of FIG. 1B, shown in FIG. 2D as in vivo fluid flow sensor device 200D. The in vivo fluid flow sensor device 200D can be configured similar to the in vivo fluid flow sensor device 200 (shown previously in FIG. 2A) and/or the in vivo fluid flow sensor device 200C (shown previously in FIG. 2C), e.g., where the sensor unit comprises example embodiments of an ultrasound sensor assembly (i.e., ultrasound sensor assembly 211D and ultrasound sensor assembly 212D) in electrical communication with the electronics unit 220 via the electrical interconnections (not shown in FIG. 2D). The electronics unit 220 is housed in connection apparatus 235. The acoustic transducer elements of the ultrasound sensor assembly 211D and 212D, respectively, are each coupled to the linkages of the linkage assembly 203D and position them in a fixed location with respect to each other. In some embodiments, for example, the connection apparatus 235D includes a hermetic package body which can carry and support a power supply, a data processing unit, and a wireless communication unit (e.g., with the antenna for transmission), e.g., enabling the power transfer to enact a charging system for a power management of functional performance. For example, mechanical force for closure by the linkages can be provided by a spring coil, deflection spring, or other method of compression to connect the ultrasound sensor assemblies 211D and 212D to intended their placement about the anatomic structure. Yet, in FIG. 2D, the linkage assembly 203D of the in vivo fluid flow sensor device 200D is configured include an anchor support 233D on each linkage of the linkage assembly 203D. The anchor supports 233D are articles that can be made from metallic or polymer material and be located on the linkage between the connection apparatus 235D and the distal portions of the linkages 239D that support the ultrasound sensor assemblies 211D and 212D. In example implementations of the device 200D, for example, the anchor supports 233D enable the linkages to be sutured or connected onto the anatomic structure (e.g., tissue or organ or vessel) by a material, e.g., such a suture silk, polymer thread, metallic suture needle, that can pass through openings 218 and bind the anchor supports 233D to the wall of the anatomic structure.

Figure 3:
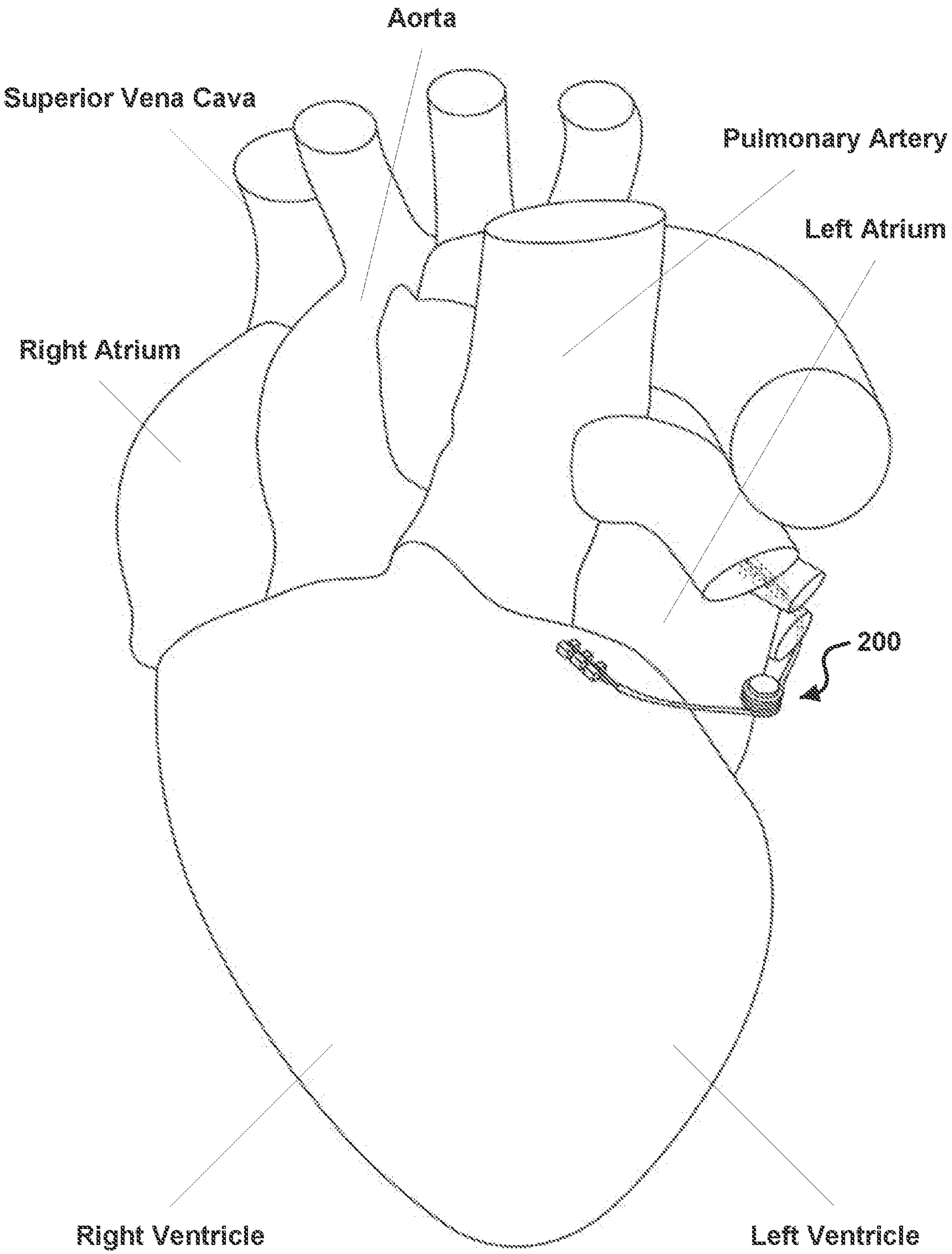
FIG. 3 shows a diagram illustrating an example embodiment of the in vivo fluid flow sensor device of FIG. 2A attached to a heart of a patient user, in accordance with the present technology.

FIG. 3 shows a diagram illustrating an example embodiment of the in vivo fluid flow sensor device 200 attached to a heart of a patient user in an example implementation of the device 200. While FIG. 3 illustrates the example in vivo fluid flow sensor device 200, it is understood other embodiments of the in vivo fluid flow sensor device 100 can be attached to the heart of the patient user to assess blood flow at the target region of the heart. In this example, the in vivo fluid flow sensor device 200 is configured to assess blood flow across the mitral valve, e.g., for assessing mitral regurgitation (MR), by placing the first ultrasound sensor assembly 211 on a proximal side of the external surface of the left atrium (LA) of the heart and the second ultrasound sensor assembly 212 on a distal side of the external surface of the LA. For example, the in vivo fluid flow sensor device 200 can be secured to the LA by clamping the first and second ultrasound sensor assemblies 211, 212 onto the LA that creates a plane normal to the mitral valve for propagating the acoustic signals. As illustrated in FIG. 3, the arms of the in vivo fluid flow sensor device 100 (e.g., linkages of the linkage assembly 203 of device 200) are capable of extending about an organ, such as the LA of the heart, with a particular spring constant that can support various orientations for optimizing functional alignment with the target anatomic structure. Further, the optimal functional alignment can be preserved by the spring constant or degree of flex of the connection apparatus, which can position and secure the device to the target anatomic structure individually or in compilation with (optional) one or more secondary attachment mechanisms, e.g., such as sutures (secured at suture ports), adhesives, or anchor structures (secured at anchoring ports), which can optimize the placement against the intended area of the organ/tissue for consistent measurements (e.g., initial monitoring to establish calibration, then comparison by constant monitoring and comparison from the baseline). Also, in some implementations, for example, multiple in vivo fluid flow sensor devices 100 can be deployed at different locations of the same anatomic structure, e.g., such as the LA of the heart (as illustrated in FIG. 3) and a major blood vessel of the heart such as the vena cava or pulmonary artery or vein (not shown in FIG. 3).

Figure 4A:
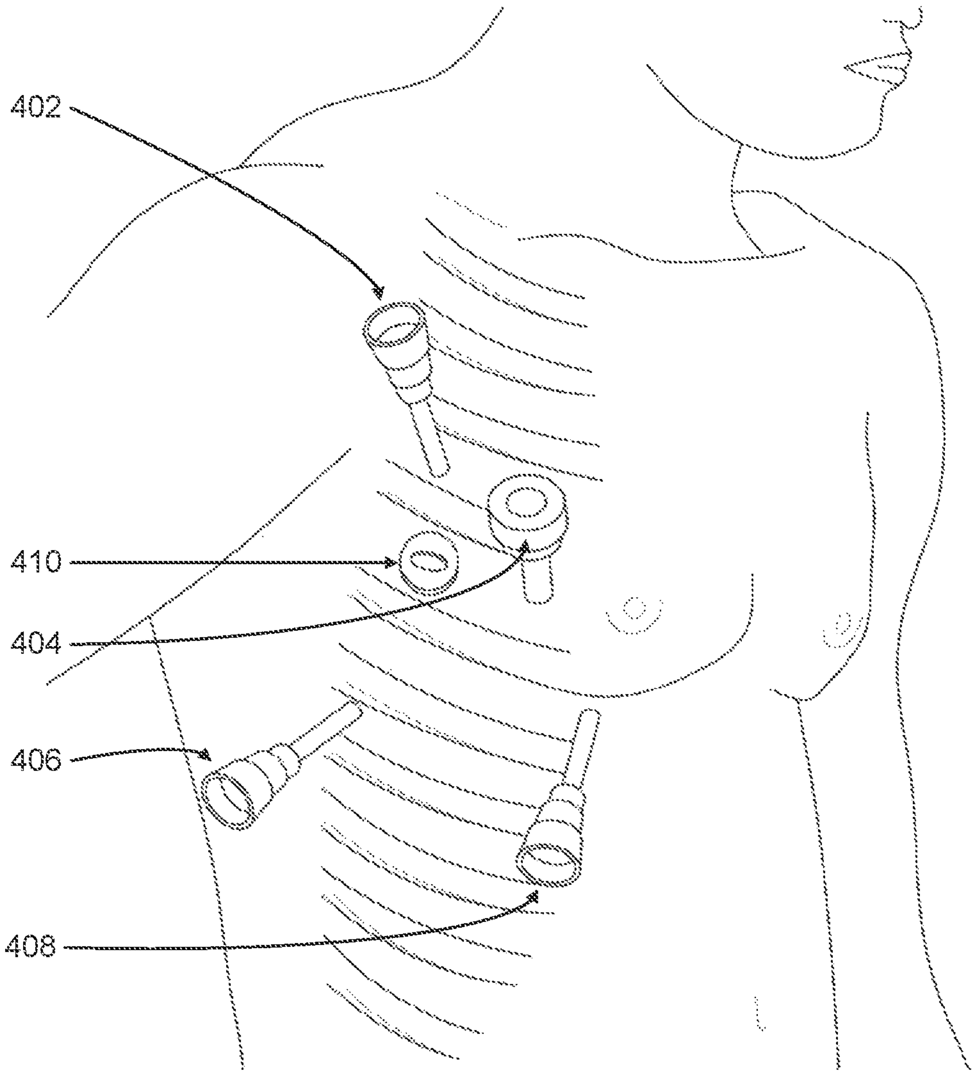
FIG. 4A shows a diagram depicting insertion sites for implanting an in vivo fluid flow sensor device in accordance with the present technology.

FIG. 4A shows a diagram depicting insertion sites for implanting various embodiments of the in vivo fluid flow sensor device 100, such as the in vivo fluid flow sensor device 200 shown in FIG. 3. In some implementations, for example, the in vivo fluid flow sensor device 200 (or other embodiments of the in vivo fluid flow sensor device 100) can be implanted and positioned onto the heart, as shown in FIG. 3, via an apical pericardial puncture and delivery of the device in the pericardial sac. The example in vivo fluid flow sensor device 200 can be attached to a mechanism for loading, carrying, and delivering into a thoracic cavity or placing on a surface of the heart (e.g., across the left atrium or right atrium) in the pericardium for monitoring fluid flow rate (e.g., forward and regurgitant flow) and other heart functions. For example, the apical pericardial implantation procedure can include using attaching the example in vivo fluid flow sensor device 200 (or other embodiments of the in vivo fluid flow sensor device 100) in a first shape conformation to a catheter that is inserted into the patient via one of the insertion sites 402, 404, 406, 408, or 410, or other insertion site not shown in FIG. 4A, which subsequently during the implantation procedure the example in vivo fluid flow sensor device 100 can change to a second shape confirmation to secure the opposing ultrasound sensor assemblies across the target region of the heart, e.g., across the left atrium in a normal plane of the mitral valve. In some implementations, for example, the catheter can be used to communicate with the example in vivo fluid flow sensor device 100 or to recharge the power supply (e.g., power supply 129) in embodiments of the device 100, if needed. In some implementations, embodiments of the in vivo fluid flow sensor device 100 can be implanted and positioned onto the heart outside of the pericardial sac.

In some implementations, for example, the in vivo fluid flow sensor device 100 can be inserted in a first phase (first conformation), e.g., by a physician user such as a thoracic surgeon, into a patient user of the device through the patient user's chest cavity by a main sternotomy or thoracotomy procedure. After insertion, the in vivo fluid flow sensor device 100 can undergo a second phase (second conformation) for placement about the heart, e.g., at the transition region between the atrium to ventricle on the left side, or at the right side in same position. The in vivo fluid flow sensor device 100 may, on its own, secure to the site of the anatomic structure placed by the surgeon, e.g., based on compression and flexion properties of the connection apparatus and/or arms (of the linkage assembly 103B), and/or may be anchored in place with suture or metal anchor, e.g., performed by the physician user.

Figure 4B:
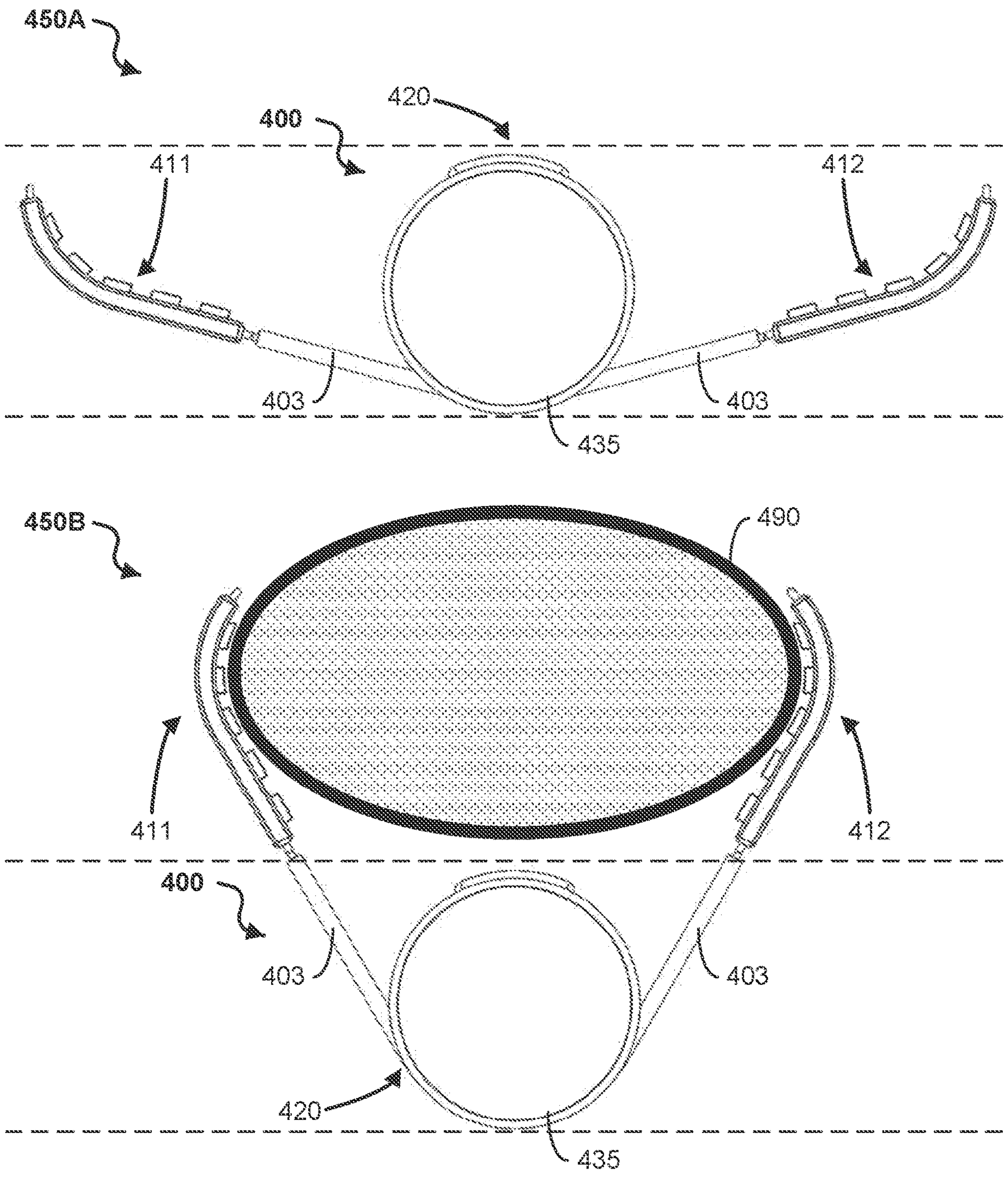
FIG. 4B shows diagrams illustrating example shape conformations of example embodiments of the in vivo fluid flow sensor device, in accordance with the present technology, for an implantation process near a target anatomic structure and a deployment process to secure to the target anatomic structure.

FIG. 4B shows diagrams illustrating example shape conformations of example embodiments of the in vivo fluid flow sensor device, in accordance with the present technology, for an implantation process near a target anatomic structure and a deployment process to secure to the target anatomic structure. Diagram 400A shows another example embodiment of the in vivo fluid flow sensor device 100B of FIG. 1B, shown in FIG. 4B as in vivo fluid flow sensor device 400, having arms of linkage assembly 403 spread outward from connection apparatus 435 to be in a first shape conformation, e.g., for an insertion or implantation process, such as implemented by a catheter. For example, in some implementations, the in vivo fluid flow sensor device 400 can be inserted into the patient's body (e.g., through a port through the ribs like the insertion site(s) shown in FIG. 4A) to approach the region where the target anatomic structure is located, e.g., such as the heart. Prior to the insertion process, the patient can be prepared by undergoing an imaging session (e.g., CT scan of the target area), which can be used in assisting the insertion.

Diagram 400B shows the in vivo fluid flow sensor device 400 in a second shape conformation, having arms of linkage assembly 403 spanning inward toward a centerline through the connection apparatus 435, e.g., for a deployment process to attach to anatomic structure 490. The in vivo fluid flow sensor device 400 can be configured similar to the in vivo fluid flow sensor device 200 (shown previously in FIG. 2A), e.g., where the sensor unit comprises the ultrasound sensor assembly 411 and the ultrasound sensor assembly 412 in electrical communication with an electronics unit 420 via the electrical interconnections (not shown). For example, during or after attachment of the in vivo fluid flow sensor device 400 to the anatomic structure 490, the ultrasound sensor assemblies 411 and 412 on the distal portions of the linkages 403 are able to be oriented about the intended measurement site (e.g., by the insertion instrument prior to its withdrawal), such that a line of site of the acoustic transducers of the ultrasound sensor assemblies 411 and 412 can be established (e.g., via transmission and reception of acoustic signals) for contact placement and/or calibration measurements. Also, for example, prior to withdrawal of the insertion instrument, the in vivo fluid flow sensor device 400 can be tested for wireless data communication with a remote device (e.g., remote computing device 130A and/or remote base station 130*b*). In some implementations, for example, sutures or other securement techniques (e.g., adhesive or other) can be used to further secure the in vivo fluid flow sensor device 400.

In some example embodiments of the ultrasound sensor assembly or assemblies for various embodiments of the in vivo fluid flow sensor device 100B of FIG. 1B, the transducer arrays are designed to spatially configure a single transmitter with at least two receivers interlaying and exchanging the receivers and transmitter, such that a singular- or multi-field of ultrasonic energy is displaced about the heart chamber (e.g., atrium or ventricle), e.g., for detecting Q-wave flow pattern(s) or disruption(s) in the flow pattern(s). By detecting the Q-wave flow pattern(s) or disruption(s) in the flow pattern(s), this data that can be interrogated and mapped to regurgitation of the blood flowing through and backflowing back through the chamber valve, which indicates wall/chamber disfunction (e.g., and can be related to electro-signal disruption for heart pulsation, and/or coagulation of static blood). Also a mechanical analysis of the chamber diametrical change can be calibrated and detected for change in use by the exemplary ultrasonic sensor assemblies 511 and/or 112, and therefore a tool for predicting heart structural-changes, e.g., such as due to water absorption by heart cells that can lead to the saturation or super saturation indicating disfunction of cell analyte removal, such as water, electrolytes, and/or cellular waste, which can result to CHF in a patient.

Figure 5A:
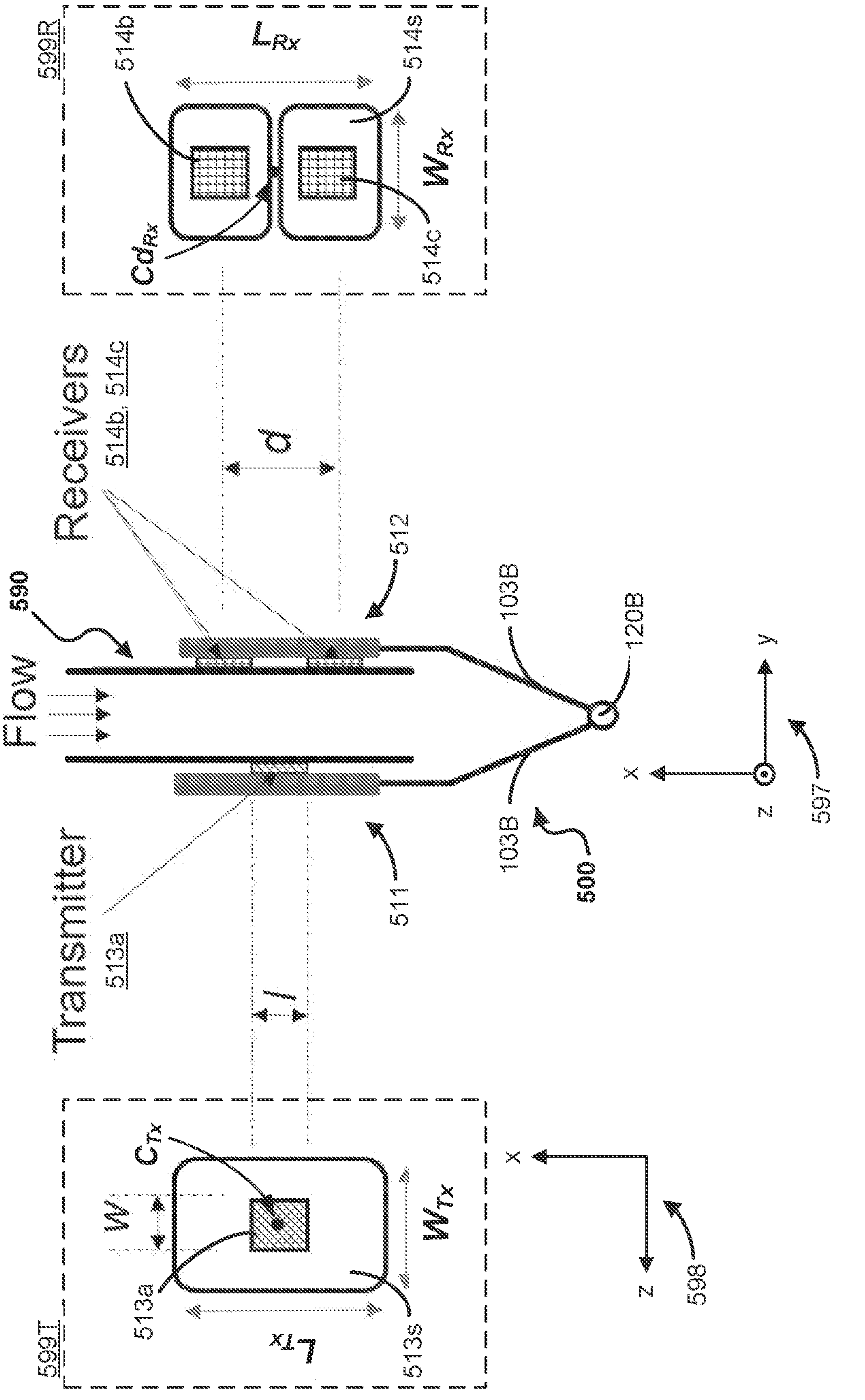
FIG. 5A shows a diagram depicting an example embodiment of a single-sided acoustic transducer configuration for an in vivo fluid flow sensor device in accordance with the present technology.

FIG. 5A shows a diagram illustrating an example implementation of the in vivo fluid flow sensor device 100B of FIG. 1B, shown in FIG. 5A as in vivo fluid flow sensor device 500 attached to an anatomic structure 590 (e.g., an atrium or ventricle of the heart or blood vessel flowing blood into or out of the heart), depicting an example embodiment of an acoustic transducer configuration in accordance with the present technology. The example in vivo fluid flow sensor device 500 includes an embodiment of the electronics unit 120B coupled to an embodiment of the linkage assembly 103B, having two opposing arms, where at their distal ends is a first ultrasound sensor assembly 511 disposed on a first arm and a second ultrasound sensor assembly 512 disposed on a second arm. The first ultrasound sensor assembly 511 includes at least one ultrasound transmitter (Tx) transducer 513*a*, and the second ultrasound sensor assembly 512 includes at least two ultrasound receiver (Rx) transducers 514*b* and 514*c*. While the drawing in FIG. 5A graphically depicts a single Tx transducer 513*a* on one arm of the example linkage assembly 103B and two Rx transducers 514*b* and 514*c* on the opposing arm of the example linkage assembly 103B, in some example embodiments, an additional Tx transducer element or additional Tx transducer elements can be included on the first ultrasound sensor assembly 511; and, in some example embodiments, an additional Rx transducer element or additional Rx transducer elements can be included on the second ultrasound sensor assembly 512. Also, for example, in some embodiments, the first ultrasound sensor assembly 511 can include two or more Rx transducer elements (e.g., at least the two Rx transducers 514*b* and 514*c*); and, for example, in some embodiments, the second ultrasound sensor assembly 512 can include one or more Tx transducer elements (e.g., at least the one Tx transducer 513*a*).

In the example shown in FIG. 5A, the in vivo fluid flow sensor device 500 provides a single-side acoustic detection system, where one or more Tx transducer(s) 513*a* are configured on one side (i.e., arm of the linkage assembly) of the device 500 to transmit acoustic signals (e.g., pulses, waveforms, etc.), and where at least two Rx transducers 514*b*, 514*c* are configured on either (i) the opposing side (i.e., other arm of the linkage assembly as the Tx transducer (s) 513*a*) of the device 500 to receive acoustic signals that correspond to the transmitted acoustic signals after propagating through the fluid in the anatomic structure 590, subject to reflections, refractions, or other propagation changes due to the fluid flow, or (ii) the same side (i.e., the same arm of the linkage assembly as the Tx transducer(s) 513*a*) of the device 500 to receive acoustic signals that correspond to the transmitted acoustic signals after propagating through the fluid in the anatomic structure 590, subject to reflections, refractions, or other propagation changes due to the fluid flow, and reflected back by a reflector structure (not shown in FIG. 5A; shown later) on the opposing side.

In some example embodiments, as shown in FIG. 5A, the acoustic transducers on the first and second ultrasound sensor assemblies 511 and 512 are configured such that the Tx transducer 513*a* is positioned on/about another portion (e.g., opposing portion) of the anatomic structure 590 from the Rx transducers 514*b*, 514*c*, where the center ($C_{Tx}$) of the Tx transducer 513*a* is aligned with the center between the distance (d) separating the centers of the Rx transducers 514*b*, 514*c*, i.e., ($Cd_{Rx}$). The spatial alignment of $C_{Tx}$ of the Tx transducer 513*a* and the $Cd_{Rx}$ between the Rx transducers 514*b*, 514*c* is configured to minimize interference of the acoustic energy during operation of the ultrasound sensor assembly or assemblies. Inset box 599T shows that the center of the Tx transducer 513*a*, $C_{Tx}$, is the midpoint of the length (I), which defines the length of a side of the Tx transducer 513*a* in that dimension, e.g., along the x-axis as shown by example coordinate map 598 in FIG. 5A. In a perpendicular dimension, e.g., along the z-axis, the center of the Tx transducer 513*a*, $C_{Tx}$, is also the midpoint of the width (w). Inset box 599R shows that the center between the distance (d) separating the centers of the Rx transducers 514*b*, 514*c*, i.e., ($Cd_{Rx}$), is based on the relative lengths of the sides of the Rx transducers 514*b*, 514*c* in that dimension, e.g., along the x-axis as shown by example coordinate map 598. Notably, the fluid flow direction is in the direction of the x-axis of the coordinate map 598 corresponding to the ultrasound sensor assemblies shown in insets 599T and 599R, as well as the coordinate map 597 corresponding to the diagram of the device 500 secured to the anatomic structure 590.

As illustrated in inset box 599T, in some example embodiments, the Tx transmitter 513*a* can be coupled to a backing or substrate 513*s* that can attach to the inner surface of the arm of the linkage assembly 103B. For example, the substrate 513*s* can provide a heat sync for management of thermal generation by the acoustic transducer(s). Similarly, inset box 599R illustrates an example embodiment of the Rx transmitters 514*b*, 514*c* coupled to a backing or substrate 514*s*, which can attach to an inner surface of the arm of the linkage assembly 103B. For example, in some embodiments, one or some of the Rx transmitters 514*b*, 514*c* can be disposed on a single substrate 514*s* or individual substrates 514*s*, in various combinations. Similarly, for example, the substrate 514*s* can provide a heat sync for management of thermal generation by the acoustic transducer(s).

In some embodiments, for example, the Tx transducer 513*a* is configured to have a 4 $mm^2$ transducer area (e.g., 2 mm×2 mm) or have a 4π $mm^2$ transducer area (e.g., 2 mm diameter) for transmission of the acoustic signals. It is understood that the width, length, or diameter (or any size dimension) of the Tx transducer 513*a* may be greater or less than 2 mm; for example, the size dimension (e.g., width, length, diameter, etc.) of the Tx transducer 513*a* can be between 1 mm to 4 mm. In some embodiments, for example, each of the Rx transducers 514*b*, 514*c* is configured to each have a 4 $mm^2$ transducer area (e.g., 2 mm×2 mm) or have a 4π $mm^2$ transducer area (e.g., 2 mm diameter) for reception of the acoustic signals. It is understood that the width, length, or diameter (or any size dimension) of the Rx transducers 514*b*, 514*c* may be greater or less than 2 mm; for example, the size dimension (e.g., width, length, diameter, etc.) of the Rx transducer 514*b*, 514*c* can be between 1 mm to 4 mm.

In some embodiments, for example, the Tx transducer 513*a* and the Rx transducers 514*b*, 514*c* are arranged to be positioned in plane (0 degrees) for line of site and wave detection, such that the Rx transducers 514*b*, 514*c* is detecting and responding to the acoustic signal from the Tx transducer 513*a* that have propagated across the anatomic structure 590 and are effected by fluid flow (e.g., blood flow in the heart or blood vessel leading to or from the heart). Yet, in some embodiments, for example, the Tx transducer 513*a* and the Rx transducers 514*b*, 514*c* are arranged to be positioned (e.g., rotated) up to 90 degrees, with respect to each other, out of plane for line of site and wave detection. Similarly, in some embodiments, for example, the Tx transducer 513*a* and/or the Rx transducers 514*b*, 514*c* can be tilted up to 20 degrees, with respect to each other, out of plane for line of site and wave detection.

In some implementations, for example, the substrate 513*s* for the Tx transducer 513*a* can be configured to have width ($W_{Tx}$) of 5 mm and a length ($L_{Tx}$) of 10 mm. Also, for example, in some implementations, the substrate 514*s* for the Rx transducers 514*b*, 514*c* can be configured to have width ($W_{Rx}$) of 5 mm and a length ($L_{Rx}$) of 10 mm.

Figure 5B:
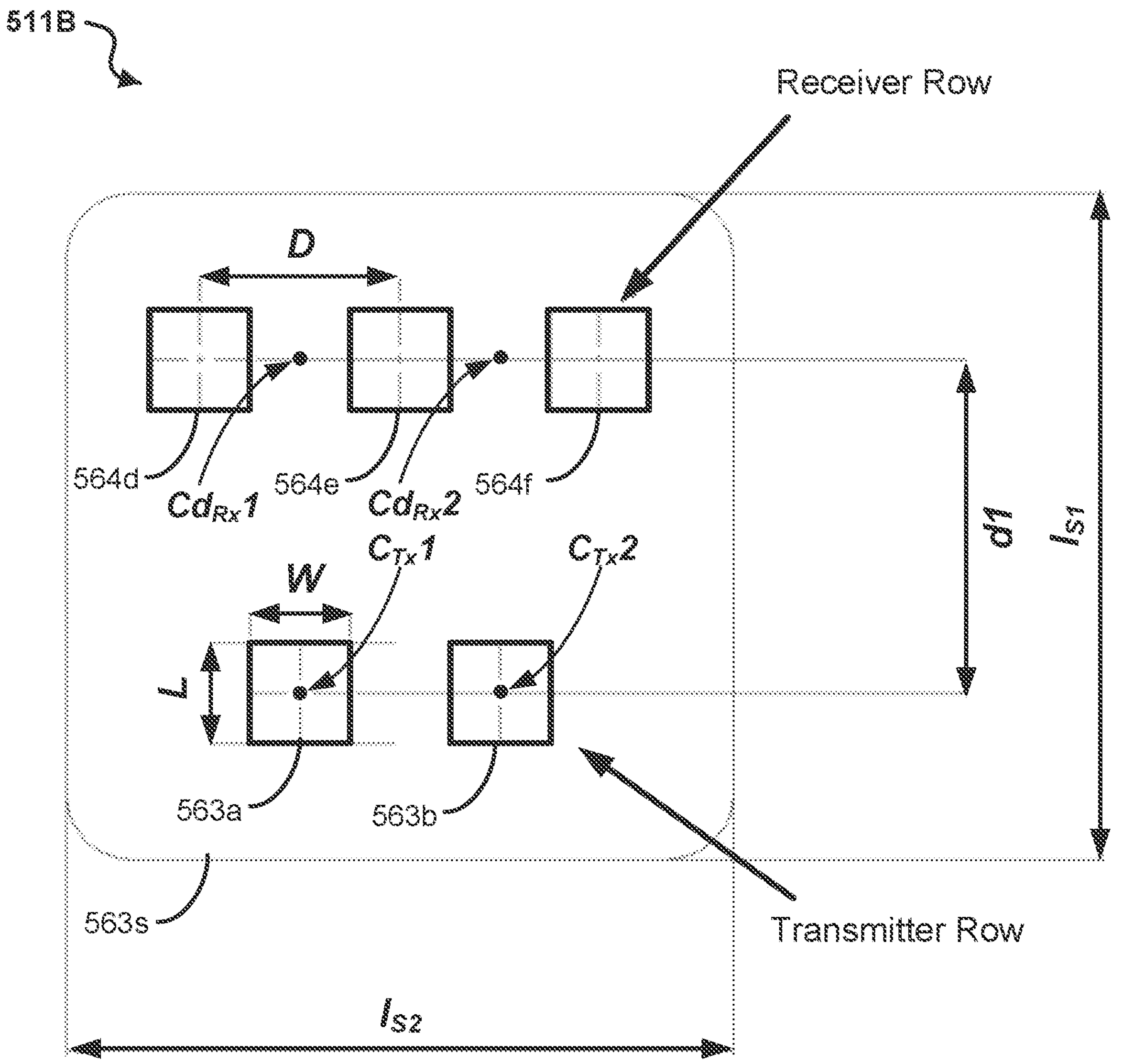
FIG. 5B shows a diagram depicting another example arrangement of a single-sided acoustic transducer configuration on an array for an in vivo fluid flow sensor device in accordance with the present technology.

FIG. 5B shows a diagram depicting an example arrangement of acoustic transducers on an ultrasound sensor assembly 511B for an example embodiment of the in vivo fluid flow sensor device 100B, such as for one or both of the first ultrasound sensor assembly 511 and the second ultrasound sensor assembly 512 of the in vivo fluid flow sensor device 500 shown in FIG. 5A. The ultrasound sensor assembly 511B includes a plurality of acoustic transducer elements 563, i.e., two acoustic transducer transmitter elements 563*a* and 563*b* in this example, and a plurality of acoustic transducer elements 564, i.e., three acoustic transducer receiver elements 564*d*, 564*e*, and 564*f* in this example. It is understood that this embodiment is not limited to two acoustic transducer transmitter elements and three acoustic transducer receiver elements for the ultrasound sensor assembly 511B, which can include less or more than the configuration shown in the diagram of FIG. 5B. In this example, the placement of the transmitter elements 563*a*, 563*b* are in a row along a single direction, and the placement of the receiver elements 564*d*, 564*e*, 564*f* are along a different row above or below the transmitter row, which is positioned at a distance (d1) with respect to the center of the transmit elements and receiver elements. The configuration of the transmitter elements 563_a_, 563_b_ and the receiver elements 564_d_, 564_e_, 564_f_ is based on the line-of-site transmission and reception (LOSTR) for the operation of the acoustic transducers in the array. In the example embodiment shown in FIG. 5B, for a single transmitter element corresponding to at least two receiver transducers (e.g., transmitter element 563_a_ corresponding to receiver elements 564_d_, 564_e_), the center ($C_{Tx1}$) of the Tx transducer 563_a_ is aligned with the center between the distance (d) separating the centers of the Rx transducers 564_d_, 564_e_, i.e., ($Cd_{Rx1}$), such that the spatial alignment of $C_{Tx1}$ of the Tx transducer 563_a_ and the $Cd_{Rx1}$ between the Rx transducers 564_d_, 564_e_ is configured to minimize interference of the acoustic energy during operation of that transmitter-receivers group of the ultrasound sensor assembly 511B. Similarly, for example, the center ($C_{Tx2}$) of the Tx transducer 563_b_ is aligned with the center between the distance (d) separating the centers of the Rx transducers 564_e_, 564_f_, i.e., ($Cd_{Rx2}$), such that the spatial alignment of $C_{Tx2}$ of the Tx transducer 563_b_ and the $Cd_{Rx2}$ between the Rx transducers 564_e_, 564_f_ is configured to minimize interference of the acoustic energy during operation of that transmitter-receivers group of the ultrasound sensor assembly 511B.

Notably, for example, some example embodiments of the ultrasound sensor assembly 511B can configure the transmitter row and the receiver row to be changed with a combination of transmitter elements and receiver elements integrated together in the same row. For example, in some implementations, the Tx transducer 563_a_ can be configured to transmit one or more acoustic signals to which acoustic signals propagated through the anatomic structure 590 are receivable by the Rx transducers 564_d_ and 564_e_, and concurrently or subsequently the transducer 564_e_ can be configured to transmit one or more acoustic signals to which acoustic signals propagated through the anatomic structure 590 are receivable by the transducers 563_a_ and 563_b_.

In some embodiments, for example, the transmitter elements 563_a_, 563_b_ can be configured to have a 2.25 $mm^2$ transducer area (e.g., 1.5 mm×1.5 mm) or have a 2.25π $mm^2$ transducer area (e.g., 1.5 mm diameter) for transmission of the acoustic signals; and the receiver elements 564_d_, 564_e_, 564_f_ can be configured to have a 2.25 $mm^2$ transducer area (e.g., 1.5 mm×1.5 mm) or have a 2.25π $mm^2$ transducer area (e.g., 1.5 mm diameter) for reception of the acoustic signals (e.g., transmitted from an opposing side array on the opposing arm of the linkage assembly of the device 500). It is understood that the width, length, or diameter (or any size dimension) of the transmitter and/or receiver transducer elements 563_a_, 563_b_ and/or 564_d_, 564_e_, 564_f_ may be greater or less than 1.5 mm. In some embodiments of the ultrasound sensor assembly 511B, the distance (d1) between the transmitter row and the receiver row, i.e., the centerline-to-centerline distance, can be substantially 5 mm, e.g., to achieve an optimal LOSTR (e.g., as a minimal distance for minimization of interference). For this example configuration of the ultrasound sensor assembly 511B, the distance separation (d1) has been optimized to ensure no cross reflection, which would be similar as a ghost signal or a signal disturbance that can create a false reading. The carrier for the transmitter and receiver can act as a coupler to the electronic communication to the processer and the power source. In some embodiments, for example, the one or more of the transmitter elements 563_a_ and 563_b_ can be rotated up to 90-degrees out of line-of-site in the same plane with respect to the corresponding at least two of the receiver elements 564_d_, 564_e_, and 564_f_, and vice versa.

The ultrasound sensor assembly 511B optionally includes a backing or substrate 563_s_, which can be used to attach the ultrasound sensor assembly 511B to an arm of a linkage assembly of the device 500. For example, the substrate 563_s_ can provide a heat sync for management of thermal generation by the acoustic transducer(s) (e.g., acoustic transducers 563_a_, 563_b_, 564_d_, 564_e_, 564_f_). In some embodiments, for example, the substrate 563_s_ can be configured to have a first side length ($I_{S1}$) of 10 mm (perpendicular to the transmitter and receiver rows) and a second side length ($I_{S2}$) of 10 mm (parallel to the transmitter and receiver rows).

In some implementations, for example, the ultrasound sensor assembly 511B can be employed in an example single-side acoustic detection system for an in vivo fluid flow sensor device 100, where one or more Tx transducer(s) are configured on one side (i.e., arm of the linkage assembly) to transmit acoustic signals (e.g., pulses, waveforms, etc.) across the anatomic structure such that at least two Rx transducers corresponding to Tx transducer are configured on the opposing side (i.e., other arm of the linkage assembly) to receive acoustic signals that correspond to the transmitted acoustic signals after propagating through the fluid in the anatomic structure, subject to reflections, refractions, or other propagation changes due to the fluid flow. Yet, some implementations, for example, the ultrasound sensor assembly 511B can be employed in an example double-side acoustic detection system for an in vivo fluid flow sensor device 100, where a first set of one or more Tx transducer(s) are configured on one side (i.e., arm of the linkage assembly) across the anatomic structure from a first set of the at least two corresponding receiver elements that operate (e.g., transmit and receive) concurrently with a second set of one or more Tx transducer(s) on an opposing arm across the anatomic structure from a second set of the at least two corresponding receiver elements. An example of a double-side acoustic detection system is illustrated later in FIG. 5D.

Figure 5C:
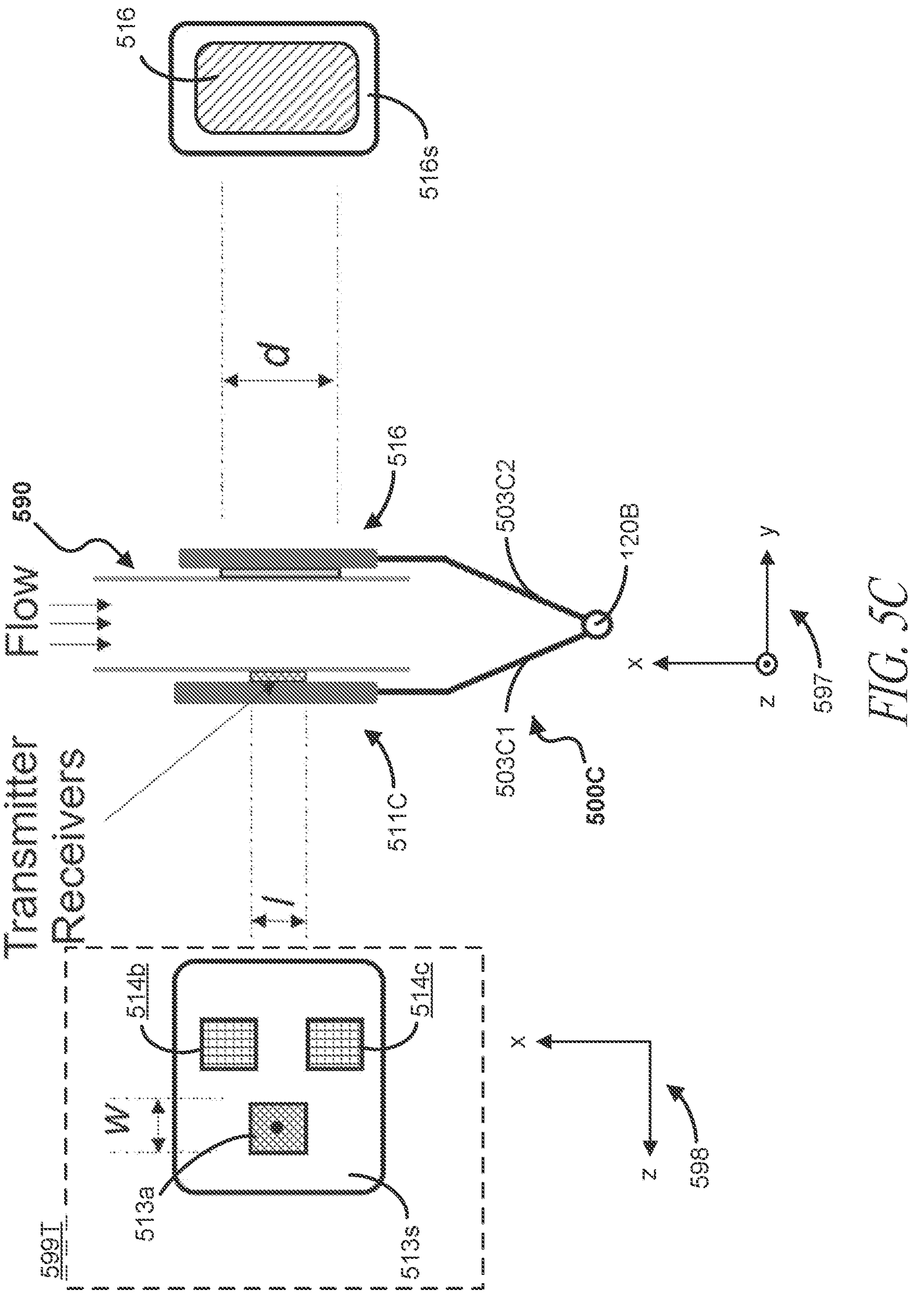
FIG. 5C shows a diagram depicting another example embodiment of a single-sided acoustic transducer configuration with a reflector for an in vivo fluid flow sensor device in accordance with the present technology.

FIG. 5C shows a diagram illustrating an example implementation of the in vivo fluid flow sensor device 100B of FIG. 1B, shown in FIG. 5C as in vivo fluid flow sensor device 500C attached to the anatomic structure 590 (e.g., an atrium or ventricle of the heart or blood vessel flowing blood into or out of the heart), depicting an example embodiment of an acoustic transducer configuration in accordance with the present technology. The example in vivo fluid flow sensor device 500C includes an embodiment of the electronics unit 120B coupled to an embodiment of the linkage assembly 103B, having two opposing arms, where at a distal end of one of the arms 503C1 is an ultrasound sensor assembly 511C, and at a distal end of the opposing arm 503C2 is a reflector 516. In some embodiments, for example, the reflector 516 can be configured as a specular reflector, having a substantively flat surface, a substantively smooth surface, and a boundary/area sized larger than the acoustic signal(s) wavelength(s). Whereas, in some embodiments, for example, the reflector 516 can be configured as a non-specular reflector, having a non-flat surface, and/or a rough or irregular surface texture, and/or a boundary/area sized smaller than the acoustic signal(s) wavelength(s). And, in some embodiments, the reflector 516 can be configured to have a specular reflector portion and a non-specular reflector portion. In various embodiments, for example, the reflector 516 can be configured in shape and size to the contour of the anatomic site (e.g., organ or vessel), in compilation with the focal length reflection for optimal energy response. Example materials of the reflector 516 can include, but is not limited to, mylar (e.g., on a substrate); a precious-metal such as silver, platinum, gold, palladium (e.g., vacuum-deposited precious metal); or a standard metal such as silver, titanium, nitinol or a stainless steel (e.g., polished for the wavelength), or a combination thereof.

The ultrasound sensor assembly 511C includes at least one ultrasound transmitter (Tx) transducer 513*a*, and at least two ultrasound receiver (Rx) transducers 514*b* and 514*c*. In this configuration, the in vivo fluid flow sensor device 500 provides a single-side acoustic detection system, where one or more Tx transducer(s) 513*a* are configured in an array with at least two Rx transducers 514*b*, 514*c* on one side (i.e., arm of the linkage assembly) of the device 500C to transmit acoustic signals (e.g., pulses, waveforms, etc.) that propagate across the anatomic structure 590, are affected by fluid flow through the anatomic structure 590, reflect from the reflector 516 configured on the opposing side (i.e., other arm of the linkage assembly) of the device 500C, and are received as acoustic signals that correspond to the transmitted acoustic signals.

In some example embodiments, these acoustic transducers on the ultrasound sensor assembly 511C can be configured with exemplary sizes, spacings, materials, and structures as described for the example acoustic transducers for the first and second ultrasound sensor assemblies 511 and 512, respectively, in connection with FIGS. 5A and 5B.

Example implementations of the in vivo fluid flow sensor device 500 were performed in an experimental benchtop apparatus designed to simulate blood flow through a chamber or tube akin to the anatomic structure 590, which tested properties of the received acoustic signals. Table 1 describes the function of frequency and sensitivity of an example single-side acoustic detection systems, i.e., at least one transmitter configured on an opposing arm of the linkage assembly to at least two receivers, e.g., exemplified by the example embodiments of the in vivo fluid flow sensor device 500 incorporating the ultrasound sensor assemblies 511, 512 shown in FIG. 5A, 511B shown in FIG. 5B, and/or 511C shown in FIG. 5C.

TABLE 1

| X | 3 MHz | | 6 MHz | | 9 MHz | |
|---|---|---|---|---|---|---|
| (mm) | ΔΦ | Δt | ΔΦ | Δt | Δ Φ | Δt |
| 1 | 0.18 | 164.1 | 0.35 | 164.1 | 0.53 | 164.1 |
| 2 | 0.35 | 328.1 | 0.71 | 328.1 | 1.06 | 328.1 |
| 3 | 0.53 | 492.2 | 1.06 | 492.2 | 1.59 | 492.2 |
| 4 | 0.71 | 656.3 | 1.42 | 656.3 | 2.13 | 656.2 |
| 6 | 1.06 | 984.4 | 2.13 | 984.4 | 3.19 | 984.2 |
| 8 | 1.42 | 1312.5 | 2.84 | 1312.5 | 4.25 | 1312.5 |

Table 1 depicts the relationship between Flow Sensitivity (Δϕ/Δt) with the example frequency (e.g., 3 MHz, 6 MHz, and 9 MHz) and the distance (mm) between the transmit and receive acoustic transducers for single-side transducer configuration. The units of sensitivity, Δϕ, are (deg/[l/min]); and the units of duration or period of function, Δt, are (ps/[l/min]).

Figure 5D:
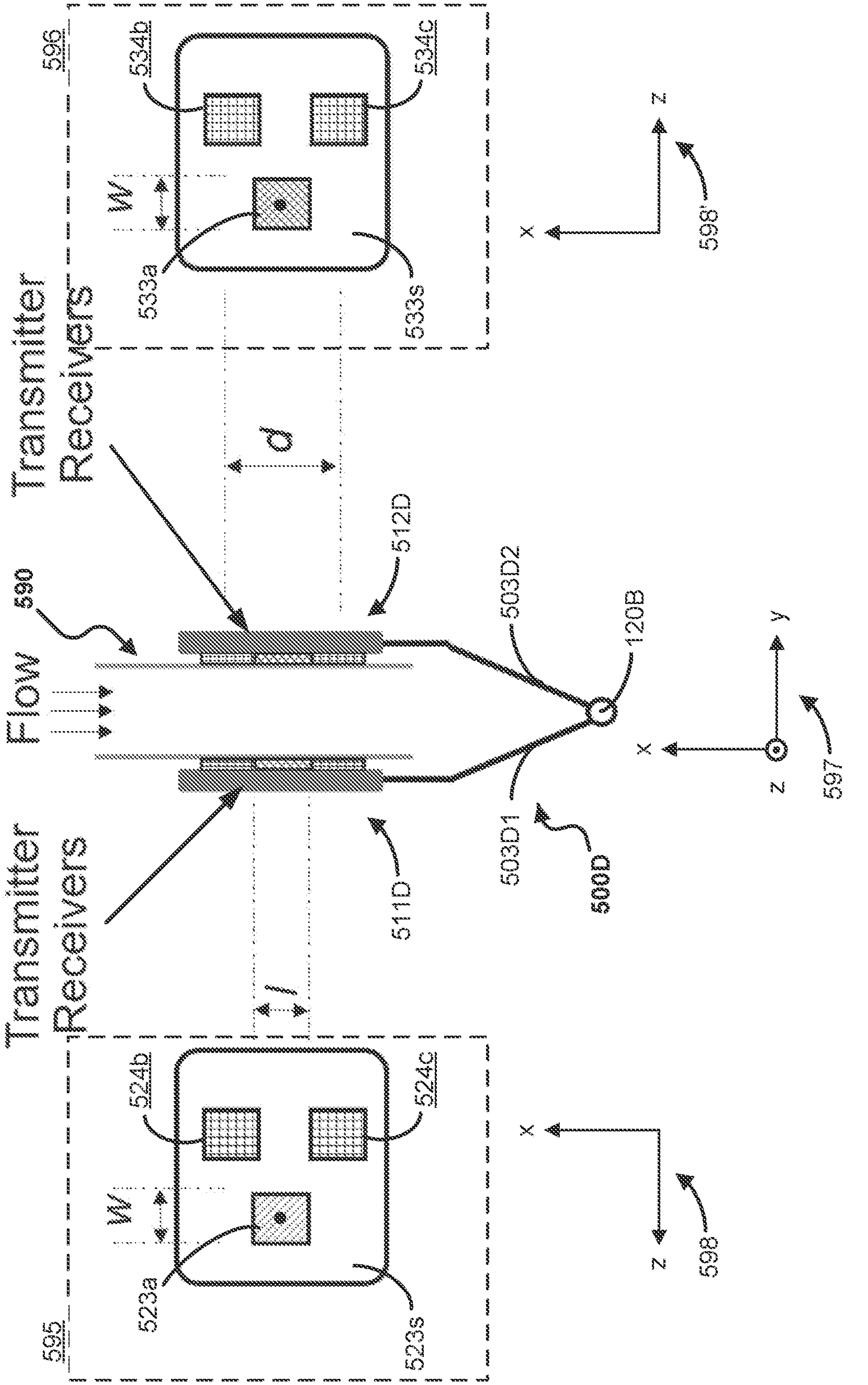
FIG. 5D shows a diagram depicting an example embodiment of a double-sided acoustic transducer configuration for an in vivo fluid flow sensor device in accordance with the present technology.

FIG. 5D shows a diagram illustrating an example implementation of the in vivo fluid flow sensor device 100B of FIG. 1B, shown in FIG. 5D as in vivo fluid flow sensor device 500D attached to the anatomic structure 590 (e.g., an atrium or ventricle of the heart or blood vessel flowing blood into or out of the heart), depicting an example embodiment of an acoustic transducer configuration in accordance with the present technology. The example in vivo fluid flow sensor device 500D includes an embodiment of the electronics unit 120B coupled to an embodiment of the linkage assembly 103B, having two opposing arms, where at their distal ends is a first ultrasound sensor assembly 511D disposed on a first arm and a second ultrasound sensor assembly 512D disposed on a second arm. The first ultrasound sensor assembly 511D, shown in inset 595, includes at least one ultrasound transmitter (Tx) transducer 523*a*; and the second ultrasound sensor assembly 512D, shown in inset 596, includes at least two ultrasound receiver (Rx) transducers 534*b* and 534*c* that correspond to the Tx transducer 523*a*. In the example embodiment shown in FIG. 5D, the second ultrasound sensor assembly 512D also includes at least one ultrasound transmitter (Tx) transducer 533*a*, and the first ultrasound sensor assembly 511D also includes at least two ultrasound receiver (Rx) transducers 524*b* and 524*c* that correspond to the Tx transducer 533*a*.

In the example shown in FIG. 5D, the in vivo fluid flow sensor device 500D provides a double-side acoustic detection system for an in vivo fluid flow sensor device 100, where a first set of one or more Tx transducer(s) (e.g., Tx transducer 523*a*) are configured on one side (i.e., arm of the linkage assembly) across the anatomic structure 590 from a first set of the at least two corresponding receiver elements (e.g., Rx transducers 534*b*, 534*c*) that operate (e.g., transmit and receive) concurrently with a second set of one or more Tx transducer(s) (e.g., Tx transducer 533*a*) on an opposing arm across the anatomic structure 590 from a second set of the at least two corresponding receiver elements (e.g., Rx transducers 524*b*, 524*c*).

In some example embodiments, these acoustic transducers on the first ultrasound sensor assembly 511D and/or the second ultrasound sensor assembly 512D can be configured with exemplary sizes, spacings, materials, and structures as described for the example acoustic transducers for the first and second ultrasound sensor assemblies 511 and 512, respectively, in connection with FIGS. 5A and 5B.

Example implementations of the in vivo fluid flow sensor device 500D were performed in an experimental benchtop apparatus designed to simulate blood flow through a chamber or tube akin to the anatomic structure 590, which tested properties of the received acoustic signals. Table 2 describes the function of frequency and sensitivity of an example double-side acoustic detection systems, e.g., exemplified by the example embodiment of the in vivo fluid flow sensor device 500D incorporating the ultrasound sensor assemblies 511D, 512D shown in FIG. 5D.

TABLE 2

| X | 3 MHz | | 6 MHz | | 9 MHz | |
|---|---|---|---|---|---|---|
| (mm) | ΔΦ | Δt | ΔΦ | Δt | Δ Φ | Δt |
| 1 | 0.09 | 82.0 | 0.18 | 82.0 | 027 | 82.0 |
| 2 | 0.18 | 164.1 | 0.35 | 164.1 | 0.53 | 164.1 |
| 3 | 0.27 | 246.1 | 0.53 | 246.1 | 0.08 | 264.1 |
| 4 | 0.35 | 328.1 | 0.71 | 328.1 | 1.06 | 328.1 |
| 6 | 0.53 | 492.2 | 1.06 | 492.2 | 1.59 | 492.2 |
| 8 | 0.71 | 656.3 | 1.42 | 656.3 | 2.13 | 656.3 |

Table 2 depicts the relationship between Flow Sensitivity (Δϕ/Δt) with the example frequency (e.g., 3 MHz, 6 MHz, and 9 MHz) and the distance (mm) between the transmit and receive acoustic transducers for double-side transducer configuration, i.e., a first set of at least one transducer element on an opposing arm across the anatomic structure from a first set of the at least two corresponding receiver elements that operate (e.g., transmit and receive) concurrently with a second set of at least one transducer element on an opposing arm across the anatomic structure from a second set of the at least two corresponding receiver elements. The units of sensitivity, $\Delta\phi$, are (deg/[l/min]); and the units of duration or period of function, $\Delta t$, are (ps/[l/min]).

The example data of Table 2 demonstrates a dampening effect using two opposing transmitters (e.g., Tx transducer 523*a* of first ultrasound sensor assembly 511D and Tx transducer 533*a* of second ultrasound sensor assembly 512D) configured to concurrently transmit acoustic signals in directions opposing each other, which is approximately half of the flow sensitivity as compared to the example data of Table 1, which is based on a ultrasound sensor assembly single-sided transmitter transducer arrangement that transmit toward a reflector with the at least two receiver transducers on the same side as the transmitter transducer, or with the at least two receiver transducers on the opposite side of the anatomic structure as the transmitter transducer.

In some example implementations of the various embodiments of the in vivo fluid flow sensor device 100B, the device can be operated to transmit and receive acoustic signals (e.g., ultrasound signals) in Doppler mode. In contrast with typical ultrasound techniques to interrogate a stationary object, Doppler ultrasound can be used to characterize fluid flow properties. For example, when a target of interest (such as blood cells in blood flow through an anatomic structure) is moving with respect to an ultrasound signal, it encounters more oscillations per unit time than a stationary equivalent, such that the frequency of the reflected wave is increased; and when the target of interest is moving away from the ultrasound signal, the frequency of the reflected signal is reduced. The Doppler effect can be used to measure the velocity of blood flow through the anatomic structure.

The example embodiments of the in vivo fluid flow sensor device 100B can be positioned at an angle (θ) with respect to the blood flow direction within the anatomic structure 590, such that the frequency shift to be measured by the Doppler mode is $(f_R - f_T) = 2\,v\,f_T \cos(\vartheta)/c$, where $f_T$ is the frequency of the transmitted acoustic signal, $f_R$ is the frequency of the acoustic signal received, and c is the velocity of the acoustic signal of a given wavelength transmitted in the medium, and v is the velocity of the acoustic signal moving toward the acoustic transducer receiving the signal.

For example, the in vivo fluid flow sensor device 100B is able to use the Doppler technique in conjunction with mass flow calculations of the blood through the anatomic structure such that the body mass flow in a confidence interval is equal to the density (known blood) and the diametric change (used to calculate area), which enables the determination of velocity. And, from velocity and diameter, the device 100B is able to determine Q of fluid flow. Furthermore, the in vivo fluid flow sensor device 100B is able to measure planar dimensions of the target anatomic structure based on the determinable changes in fluid flow with respect to a baseline measurement, e.g., since increased fluid amount (volume) typically causes the walls of the anatomic structure (e.g., major blood vessel) to expand, i.e., an increase in the diameter of the walls.

In some example implementations of the various embodiments of the in vivo fluid flow sensor device 100B, the device can be operated to transmit and receive acoustic signals (e.g., ultrasound signals) to create ultrasound images of the target anatomic structure, e.g., using A-mode, B-mode, and/or C-mode ultrasound data acquisition techniques. In some examples, embodiments of the in vivo fluid flow sensor device 100B may be used in A-Mode ultrasound acquisition to obtain a one-dimensional presentation from the transmitted and received acoustic signals waves in the direction that the ultrasound transducer assembly is oriented, e.g., where one axis represents a depth and a perpendicular axis represents an amplitude. In some examples, embodiments of the in vivo fluid flow sensor device 100B may be used in B-Mode, also referred to as 2D mode, to obtain a two-dimensional presentation from the transmitted and received acoustic signals waves, e.g., based on the angle that the ultrasound transducer assembly is positioned with respect to the anatomic structure. In some examples, embodiments of the in vivo fluid flow sensor device 100B may be used in C-Mode to obtain both a range of depth from A-Mode and 2D information from B-Mode.

Figure 6A:
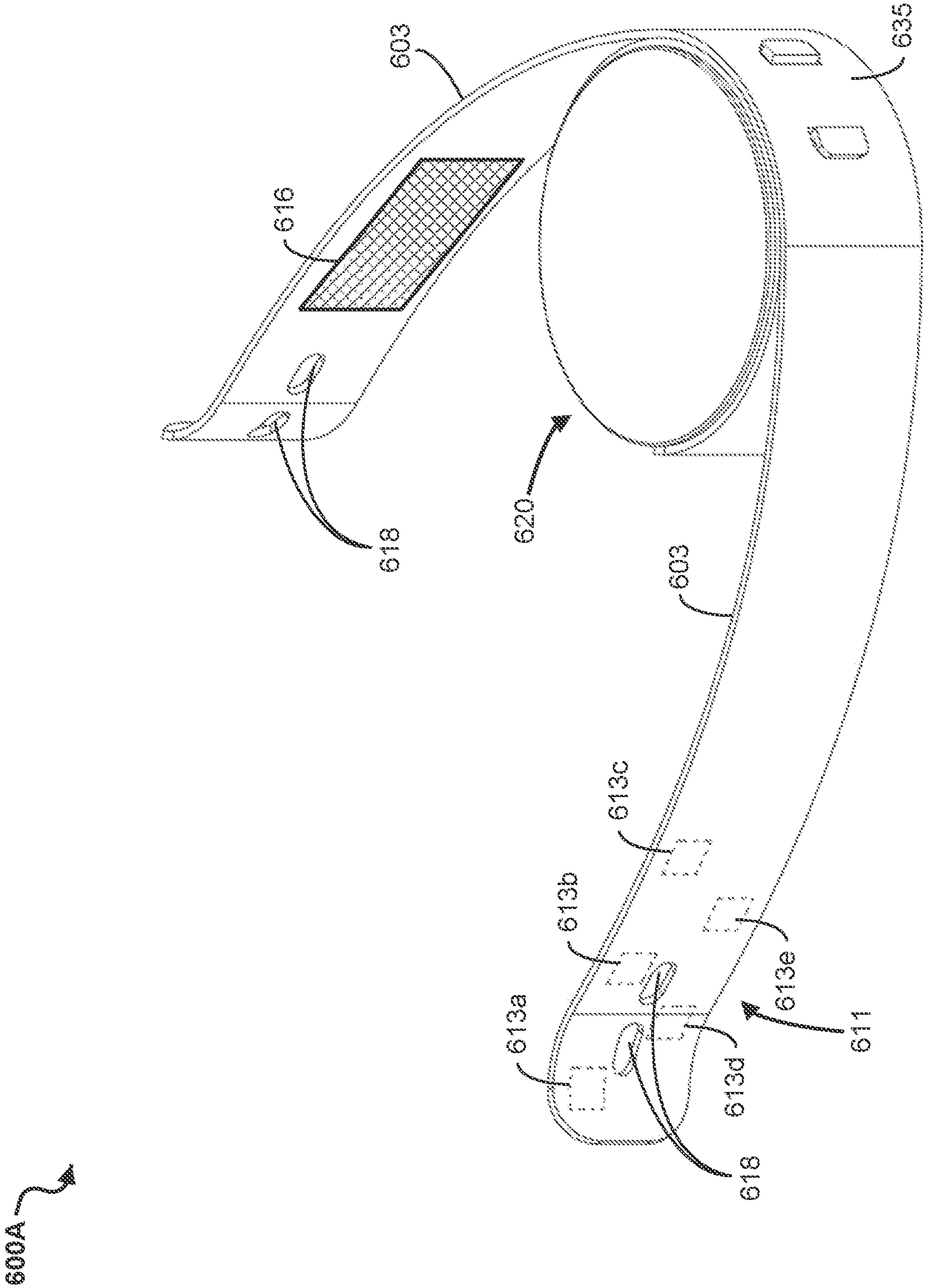
FIGS. 6A, 6B and 6C show diagrams depicting other example embodiments of the in vivo fluid flow sensor device of FIG. 1B, in accordance with the present technology.

FIG. 6A shows a diagram depicting an example embodiment of the in vivo fluid flow sensor device 100B of FIG. 1B, shown in FIG. 6A as in vivo fluid flow sensor device 600A. The in vivo fluid flow sensor device 600A includes a sensor unit comprising at least one ultrasound sensor assembly 611 in electrical communication with an electronics unit 620 via electrical interconnections (not shown), in which the electrical interconnections are configured on a surface or within a material body of a clip band 603. The electronics unit 620 is housed in a connection apparatus 635 that connects the arms of the clip band 603. The ultrasound sensor assembly 611 includes a plurality of acoustic transducer elements 613, e.g., five acoustic transducer elements 613*a*, 613*b*, 613*c*, 613*d*, 613*e* in this example, positioned on the inner-facing side of the arm of the clip band 603. It is understood that this embodiment is not limited to five acoustic transducer elements for each ultrasound sensor assembly and can include less or more than the configuration shown in the diagram of FIG. 6A, e.g., including but not limited to one or more acoustic transducer element for the ultrasound sensor assembly 611. The other arm of the clip band 603 may include an embodiment of the reflector 516 (shown in FIG. 6A as reflector 616) configured to reflect acoustic signals transmitted by the ultrasound sensor assembly 611 that propagate across the anatomic structure, are affected by fluid flow through the anatomic structure, reflect from the reflector 616, and are received as returned acoustic signals by the ultrasound sensor assembly 611 (that correspond to the transmitted acoustic signals). In some embodiments, the reflector 616 may be attached to a backing or substrate 616*s*, which may attach to the inner surface of the arm of the clip band 603.

The clip band 603 is configured to secure the acoustic transducer elements 613 and the reflector 616 to position them in a fixed location with respect to each other. In some embodiments, for example the clip band 603 can be composed of a composite material having a durometer parameter of the polymer component (e.g., 20A to 95A), and stiffener material (e.g., made of a shape-set material, such Nitinol), which allows the clip band 603 to be pre-shaped and/or pre-trained (allowing the clip band 603 to be set within a first shape/configuration for delivery/implantation, after which it can take a second shape/configuration for deployment/operation). Some non-limiting examples of the composite material for the clip band 603 can include a Nitinol, gold, platinum, platinum/iridium, etc. encased in a polymer, such as silicone, polyethylene, polyimide, polyamide, or blended polyimide-polyamide, or other polymer material.

In some embodiments of the in vivo fluid flow sensor device 600A, the clip band 603 can include one or more openings 618 on at least one or both of the arms of the clip band 603 that allows for secondary attachment means of the device 600A to the target anatomic structure. For example, the openings 618 shown in the example of FIG. 6A include a portion of the clip band 603 between the two voids that are the openings 618, which provides an anchor site to apply a suture (e.g., stitch thread, wire, etc.) that affixes the arm of the clip band 603 to the anatomic structure (e.g., wall of the atrium of the heart).

Figure 6B:
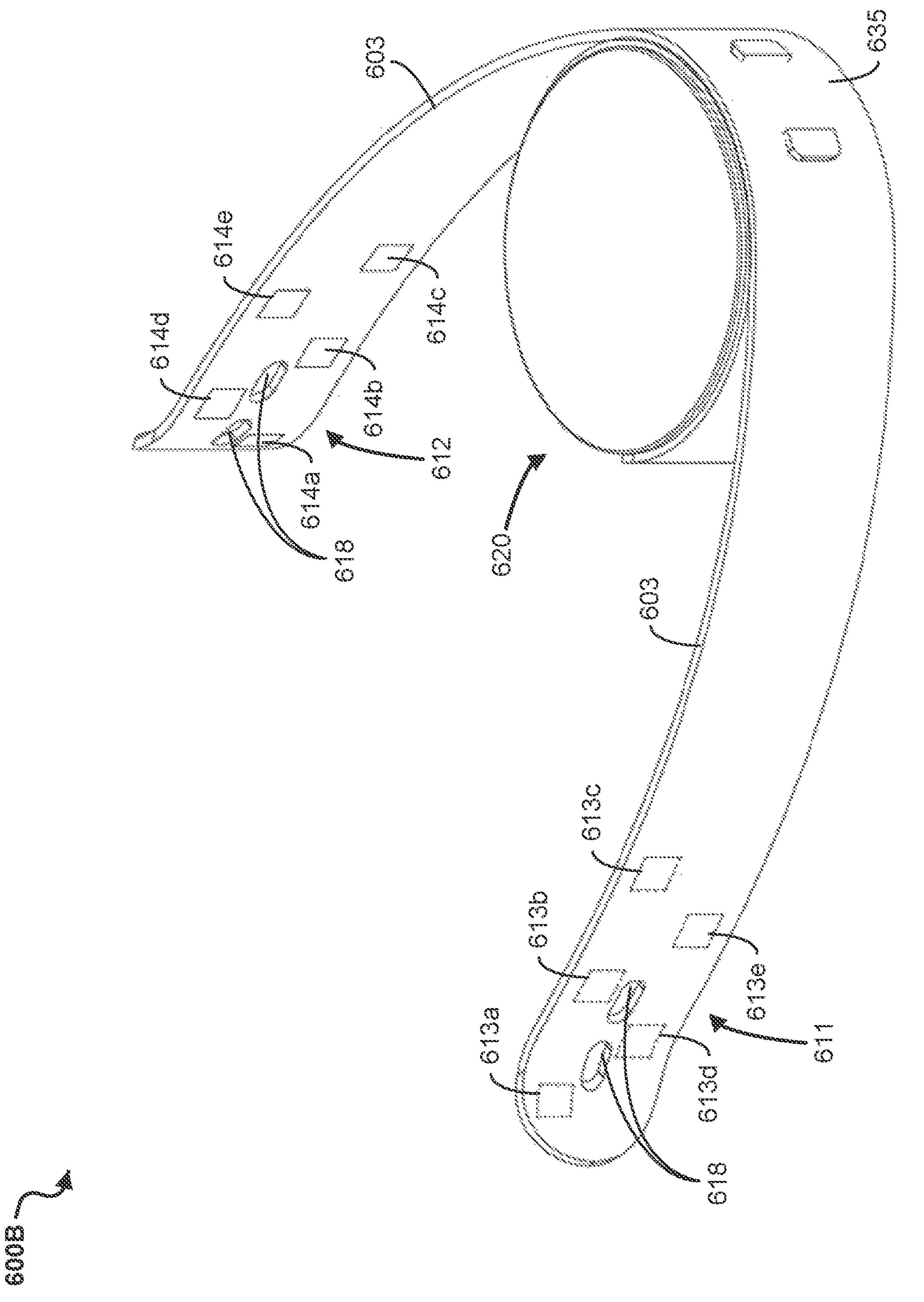

FIG. 6B shows a diagram depicting an example embodiment of the in vivo fluid flow sensor device 600A of FIG. 6A, shown in FIG. 6B as in vivo fluid flow sensor device 600B. The in vivo fluid flow sensor device 600B includes a sensor unit comprising the ultrasound sensor assembly 611 and a second ultrasound sensor assembly 612, both in electrical communication with the electronics unit 620 via electrical interconnections (not shown), in which the electrical interconnections are configured on a surface or within a material body of the clip band 603. The electronics unit 620 is housed in a connection apparatus 635 that connects the arms of the clip band 603. The ultrasound sensor assembly 612 includes a plurality of acoustic transducer elements 614 positioned on the arm of the clip band 603 opposite to the arm on which the ultrasound sensor assembly 611 is disposed. In the example shown in FIG. 6B, the plurality of acoustic transducer elements includes five acoustic transducer elements 614*a*, 614*b*, 614*c*, 614*d*, 614*e*, which are positioned on the inner-facing side of the arm of the clip band 603 in a particular configuration with respect to each other and with respect to the acoustic transducer elements 613 of the ultrasound sensor assembly 611 on the opposing arm of the clip band 603. It is understood that this embodiment is not limited to five acoustic transducer elements for each ultrasound sensor assembly and can include less or more than the configuration shown in the diagram of FIG. 6B, e.g., including but not limited to one or more acoustic transducer element for the ultrasound sensor assembly 611. The clip band 603 is configured to secure the acoustic transducer elements 613 and the acoustic transducer elements 614 and position them in a fixed location with respect to each other. In some embodiments, the clip band 603 of the in vivo fluid flow sensor device 600B can include one or more openings 618 on at least one or both of the arms of the clip band 603 that allows for secondary attachment means of the device 600B to the target anatomic structure. For example, the openings 618 shown in the example of FIG. 6B include a portion of the clip band 603 between the two voids that are the openings 618, which provides an anchor site to apply a suture (e.g., stitch thread, wire, etc.) that affixes the arm of the clip band 603 to the anatomic structure (e.g., wall of the atrium of the heart).

Figure 6C:
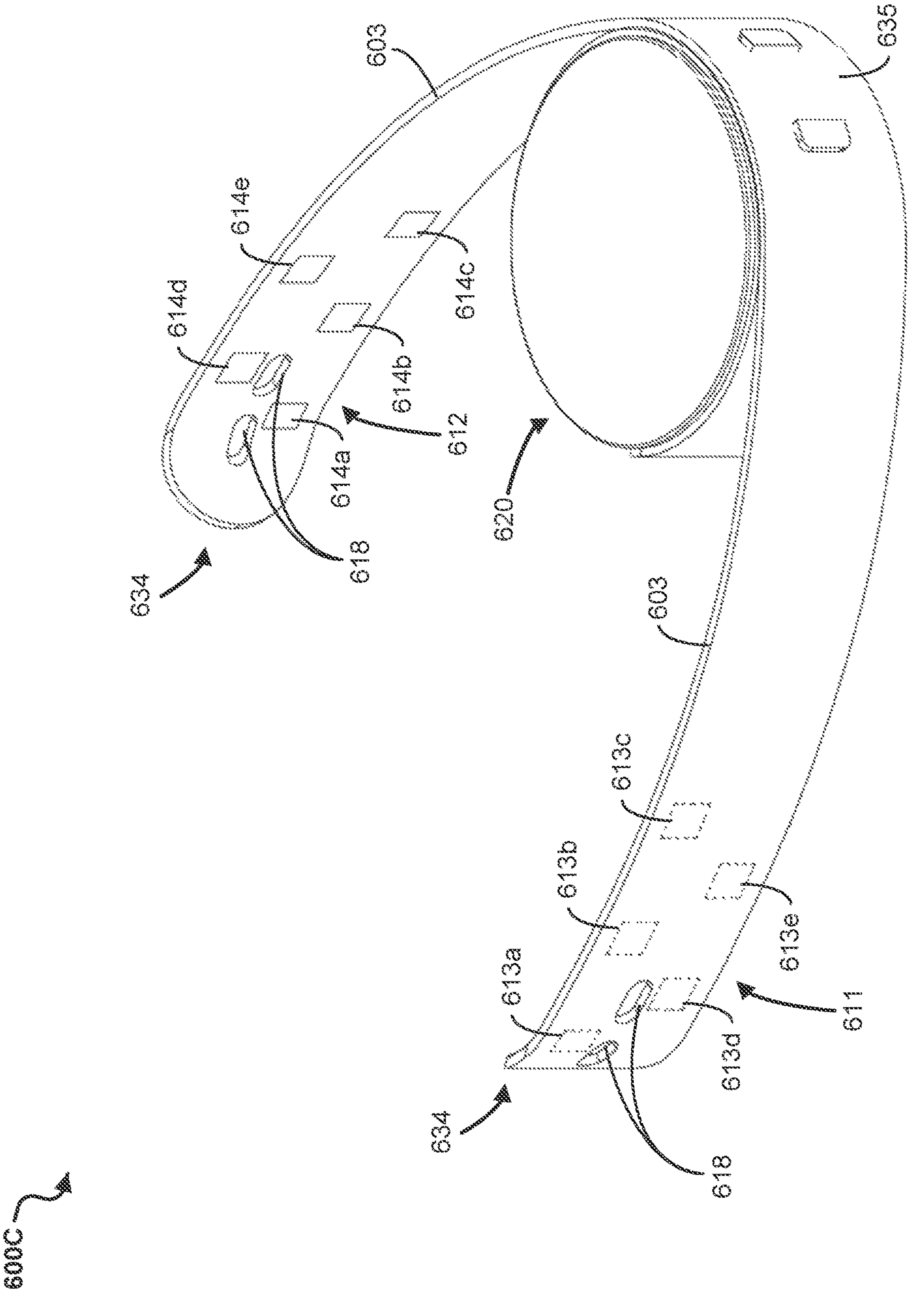

FIG. 6C shows a diagram depicting an example embodiment of the in vivo fluid flow sensor device 600A of FIG. 6A and/or in vivo fluid flow sensor device 600B of FIG. 6B, shown in FIG. 6C as in vivo fluid flow sensor device 600C. The in vivo fluid flow sensor device 600C includes a sensor unit comprising the ultrasound sensor assembly 611 and/or the second ultrasound sensor assembly 612, both in electrical communication with the electronics unit 620 via electrical interconnections (not shown), in which the electrical interconnections are configured on a surface or within a material body of the clip band 603. The electronics unit 620 is housed in a connection apparatus 635 that connects the arms of the clip band 603. The in vivo fluid flow sensor device 600C includes an inner curved region 634 of the distal ends of each arm of the clip band 603, e.g., which can assist in facilitating attachment and conformation to the anatomic structure upon placement as well as aid in delivery of the device 600C, e.g., via a catheter The one or more openings 618 can be disposed on the inner curved region 634 and/or on the arm proximate the inner curved region 634 on at least one or both of the arms of the clip band 603, e.g., allowing for secondary attachment means of the device 600B to the target anatomic structure. In some embodiments, the connection apparatus 635 may be attached to the clip band 603 on the outside of the arms of the clip band 603 (not shown), which may be preferred for in vivo applications where the device 600C is deployed on a blood vessel (e.g., such as the vena cava or pulmonary artery or vein).

The example embodiments of FIGS. 6A-6C of the in vivo fluid flow sensor device 600A, 600B, and 600C, respectively, include a soft arm configuration of the clip band 603 for pliability and conformability to the intended site of placement. The arms of the clip band 603 can facilitate and maintain electronic transmissions through the interconnections (not shown) to the electronics unit 620 housed in the connection apparatus 635. The clip band 603 is able to enhance the contact of the device 600A, 600B, 600C with the anatomic structure for ultrasonic measurements to be detected. The arms of the clip band 603 can include a flexible, non-conductive, bioinert substrate material, upon or embedded within which is a flexible circuit and carrier for the ultrasound sensor assembly 611 and/or the second ultrasound sensor assembly 612. In this manner, the clip band 603 can undergo and withstand mechanical force during placement in an action to connect to the device to the intended position and during operation for long period of time (e.g., hundreds of millions of cycles, such as heart beats). In some embodiments, the arms of the linkage assembly 603 can use of a braid metallic or polymer sheets, which are subsequently interlaid with trace-lines for electrical connection.

Figure 6D:
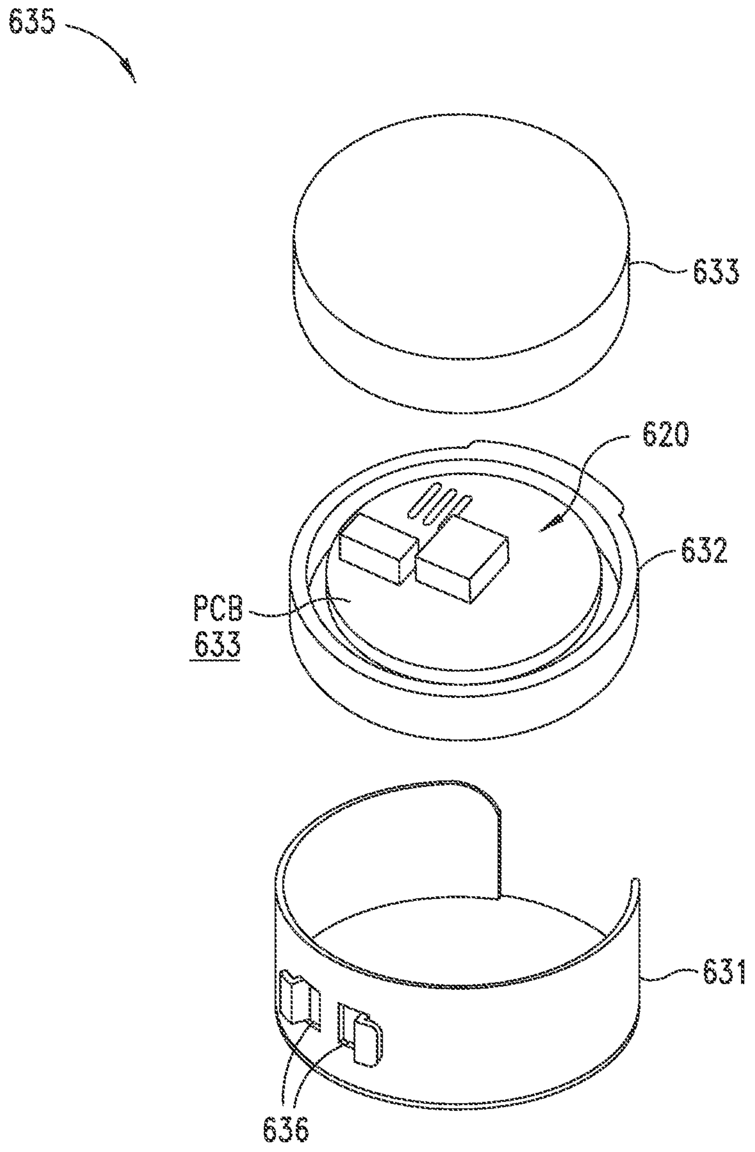
FIG. 6D shows an exploded diagram depicting an example embodiment of an electronics unit and housing of the in vivo fluid flow sensor devices of FIGS. 6A, 6B and 6C.

FIG. 6D shows an exploded diagram depicting an example embodiment of the electronics unit 620 that is housed in the connection apparatus 635 of the in vivo fluid flow sensor device 600A, 600B, and 600C of FIGS. 6A-6C. In some embodiments, for example, the connection apparatus 635 includes a base housing 631 and a removably attachable cap 633 that can be secured to (e.g., hermetically seal) the base housing 631 to protect the interior components (e.g., the electronics unit 620) from the exterior environment (e.g., biofluids and/or bioconstituents). In some (optional) embodiments, for example, the connection apparatus includes an intermediate housing 632 to contain the electronics unit 620; for example, the intermediate housing 632 can be manufactured separately and in a multitude of physical conformations (e.g., shapes and sizes) to allow modularity with various embodiments of the connection apparatus 635 in any embodiment of the in vivo fluid flow sensor device 100, 100B.

In some embodiments, the base housing 631, intermediate housing 632, and/or the cap 633 can be connected via a hermetic seal material (e.g., a non-permeable material, such as a metallic or metallic film (thin-film) and/or a woven cloth or polymer, such as parylene, a urethane, or a Teflon material) and coated to ensure a non-permeable interface between any of the base housing 631, intermediate housing 632, and/or the cap 633 to prevent fluids from breaching the connection apparatus 635 into the electronics unit 620, such as water or blood.

The electronics unit 620 includes a printed circuit board (PCB) 622 that facilitates a data processing unit, a wireless communications unit, and a power unit. For example, in some embodiments, the PCB 622 includes an embodiment of the data processing unit 121 to at least partially process the conditioned electrical signals to (i) produce data, e.g., in an analog or a digital form, and/or (ii) control functionality of the electronics unit 620 and/or the ultrasound sensor assembly 611 and/or 612. For example, the data processing unit 121 can be configured to manage data acquisition on data channels associated with the one or more acoustic transducers of the ultrasound sensor assembly 611 and/or 612. Also, for example, in some embodiments, the PCB 622 includes a power cell, e.g., which can be a super cap or small hermitic battery that is able to be recharged by inductance and/or function individually or in conjunction as a hybrid super capacitor battery, such that recharge and run times are balanced to be efficient for the required monitoring power and communication drain.

In some embodiments, the wireless communications unit of the electronics unit 620 includes an antenna, which can comprise Platinum, or 90/10 Platinum Iridium, Gold, Platinum pure wire, e.g., in a cross-sectional size from 0.000001 $in^2$ to 0.008 $in^2$, configured in a wire or tubular configuration. As an example, a shaped-set Nitinol wire with gold plating or a co-extruded gold external layer can be used. The exemplary wire(s) can be single or combined in a winded or braided configuration for optimal density to receive and transmit singles support the transfer of information in a single or multi directional pattern. In some embodiments, the antenna can be configured in any of the aforementioned patterns on a flat, flexible circuit geometry, such as a PCBA (printed circuit board assembly). In some embodiments, for example, the antenna can be configured as a snake antenna or a coil antenna fit into the electronic package; and/or in some embodiments, for example, the antenna can be configured as a power transfer antenna reference operable for battery charging.

In some embodiments, the wireless communications unit of the electronics unit 620 includes an integrated Bluetooth, galvanic or radio in an antenna communication system. In some implementations, the electronic signals transduced by the ultrasound sensor assembly 611 and/or 612 can be transmitted to a remote device outside of the patient's body as a communication data package, e.g., transmitted through the chest cavity to a receiving scanner, receiver transmitter, a receiving card (e.g., similar to an EKG port contact) or a base station equivalent.

Figure 7A:
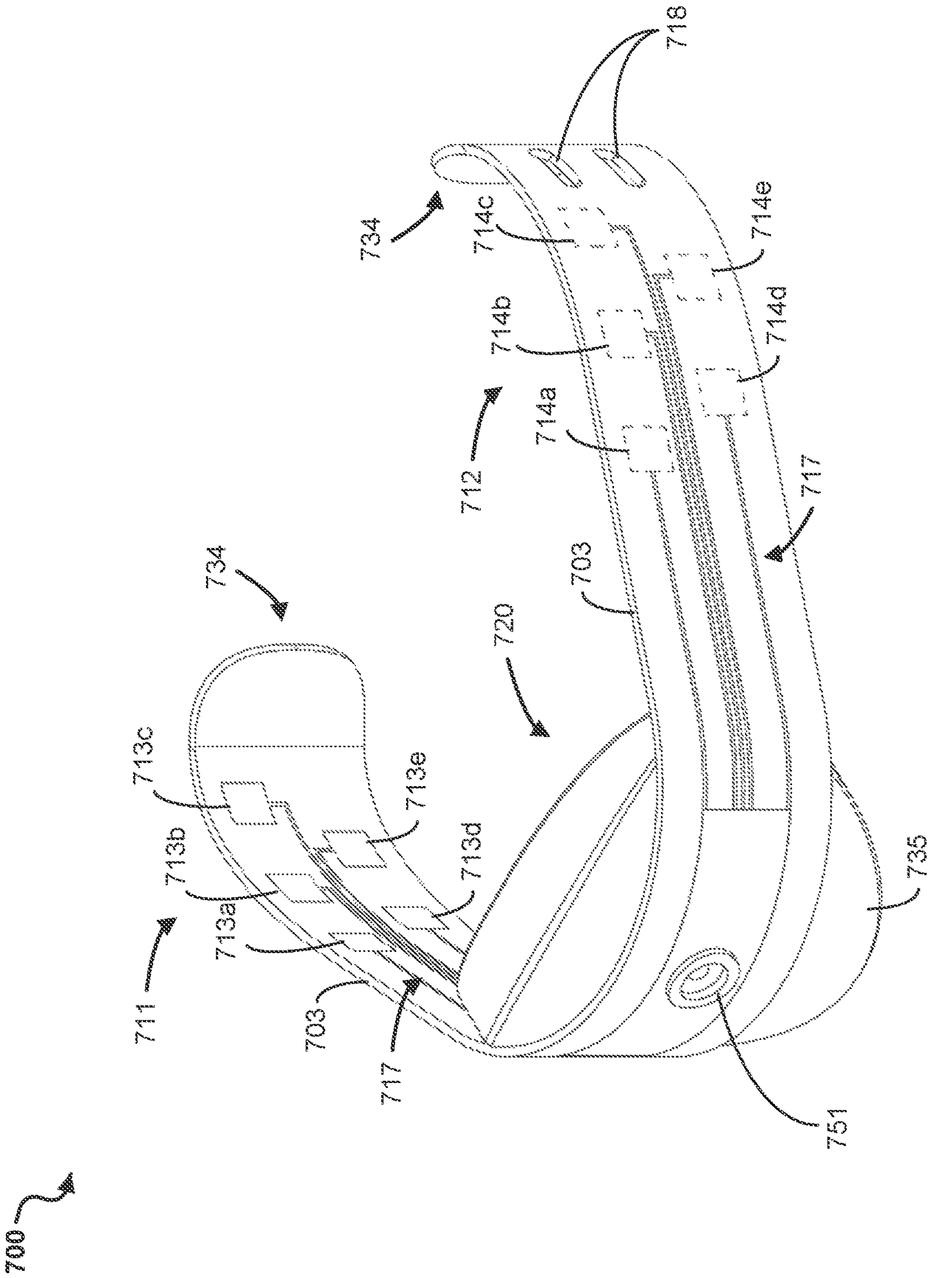
FIG. 7A shows a diagram depicting an example embodiment of the in vivo fluid flow sensor device of FIG. 1B, in accordance with the present technology.

FIG. 7A shows a diagram depicting an example embodiment of the in vivo fluid flow sensor device 100B of FIG. 1B, shown in FIG. 7A as in vivo fluid flow sensor device 700. The in vivo fluid flow sensor device 700 includes a sensor unit comprising a first ultrasound sensor assembly 711 and a second ultrasound sensor assembly 612, both in electrical communication with the electronics unit 720 via electrical interconnections 717, in which the electrical interconnections 717 are configured on a surface or within a material body of an example embodiment of the clip band 603 (shown in FIG. 7A as clip band 703). The electronics unit 720 is housed in a connection apparatus 735 that connects the arms of the clip band 703.

The connection apparatus 735 can include features of the example embodiments of the connection apparatus 235, 235C, and/or 635, such as a spring, interconnection links, housing structures (e.g., base, cap, etc.), and other features described in relation to other connection apparatus embodiments disclosed herein. Referring to FIG. 7A, the connection apparatus 735 includes a power and/or data port 751 operable to interface (e.g., be in electrical communication and/or data communication) with the electronics unit 720 housed in the connection apparatus 735. For example, the electronics unit 720 of the in vivo fluid flow sensor device 700 can include a rechargeable power supply or in intermediary power supply that can be tethered to a separate power supply and/or data processing unit that is remote to the device 700, via the power and/or data port 751. In some example embodiments, the remote power supply and/or data processing unit may be an in vivo device located within the patient's body, but in a region that is easier to access to change a battery or wirelessly communicate with. For example, the remote in vivo device may be in wired communication and supply electrical power to the electronics unit 720 of the in vivo fluid flow sensor device 700 via a cable, wire, cord, etc. (e.g., that is coated by an insulative, bio-inert material) through the power and/or data port 751. As an illustrative example, the in vivo fluid flow sensor device 700 may be deployed in a confined space, such as inside or about the pericardium positioned at an atrium or ventricle, or positioned about the superior or inferior vena cava or a pulmonary artery, which is tethered to a larger in vivo power source device that is located in a cavity far away from the device 700 deployment site, e.g., such as one or a few or tens of centimeters away, such as a pleural cavity or cavity in the abdominal space, where there is more flexibility, size, and/or positioning to facilitate larger power supply and/or electronic components, and to allow for replacement of such components. In some examples, the remote power source may be located out of the body, with the power and/or data cable passing from power and/or data port 751 of the device 700 to the remote power source outside of the patient's body.

In some example implementations, an in vivo fluid flow sensor platform that includes the device 700 can include the optional one or more secondary sensor(s) 119 disposed within the remote in vivo device in wired communication with the sensor unit 720 via the cable, wire, cord, etc. that is connected through the power and/or data port 751. For instance, in some implementations, an example secondary sensor 119 can include an IMU to determine the patient user's motion (e.g., whether resting (e.g., laying down, sitting, etc.) or moving (e.g., walking, running, etc.). Furthermore, example secondary sensors(s) 119 as part of the in vivo fluid flow sensor platform can include, in some embodiments, an acoustic sensor to monitor breathing (respiratory parameters) by the patient user (e.g., respiratory rate of inhalation and exhalation, turbulent airflow, etc.) being monitored by the in vivo fluid flow sensor device 700. And yet further, example secondary sensors(s) 119 as part of the in vivo fluid flow sensor platform can include, in some embodiments, an EKG monitor (e.g., external wearable cardiac monitor or an in vivo insertable cardiac monitor) to measure electrocardiograms of the patient user being monitored by the in vivo fluid flow sensor device 700. In this manner, for example, the in vivo fluid flow sensor device 700 can measure blood flow through the target cardiac anatomy simultaneous with (temporally in sync with) sensing information of the patient user's motile state, breathing state, and/or heart rate.

In some example implementations, the remote in vivo device of the in vivo fluid flow sensor platform (that is in wired communication with the in vivo fluid flow sensor device 700) can include a secondary transmission device (e.g., wireless communication unit) for the sake of power control and optimal continuous data management, e.g., which can be communicated to the remote device 130 (e.g., base station 130B and/or mobile communication device 130A). For example, data transmissions by the example secondary transmission device (deployed remote from the device 700) can wirelessly transmit the data collected by the device 700 every minute, every second, etc. due to the reduced constraints and challenges on power consumption by the remote secondary transmission device with respect to the device 700. In some embodiments, for example, the secondary transmission device of the remote in vivo device can a transmitter, a receiver, and/or a transceiver with an antenna using a low power wireless communication protocol, e.g., such as Bluetooth Low Energy (BLE), Near Field Communication (NFC), low frequency radio frequency (RF) signal in a range of 3 kHz to 1.3 MHz, or other.

Referring to the example embodiment of the in vivo fluid flow sensor device 700 shown in FIG. 7A, the first ultrasound sensor assembly 711 includes a plurality of acoustic transducer elements 713 positioned on an arm of the clip band 703 that is opposite to the arm on which the second ultrasound sensor assembly 712 is disposed. In the example shown in FIG. 7A, the plurality of acoustic transducer elements 713 of the first ultrasound assembly 711 includes five acoustic transducer elements 713*a*, 713*b*, 713*c*, 713*d*, 713*e*, which are positioned on the inner-facing side of the arm of the clip band 703 in a particular configuration with respect to each other and with respect to the acoustic transducer elements 714 of the second ultrasound sensor assembly 712 on the opposing arm of the clip band 703. It is understood that this embodiment is not limited to five acoustic transducer elements for the first ultrasound sensor assembly 711 and can include less or more than the configuration shown in the diagram of FIG. 7A, e.g., including but not limited to one or more acoustic transducer element for the first ultrasound sensor assembly 711. The second ultrasound sensor assembly 712 includes a plurality of acoustic transducer elements 714 positioned on the arm of the clip band 703 opposite to the arm on which the first ultrasound sensor assembly 711 is disposed. In the example shown in FIG. 7A, the plurality of acoustic transducer elements includes five acoustic transducer elements 714*a*, 714*b*, 714*c*, 714*d*, 714*e*, which are positioned on the inner-facing side of the arm of the clip band 703 in a particular configuration with respect to each other and with respect to the acoustic transducer elements 713 of the first ultrasound sensor assembly 711 on the opposing arm of the clip band 703. It is understood that this embodiment is not limited to five acoustic transducer elements for each ultrasound sensor assembly and can include less or more than the configuration shown in the diagram of FIG. 7A, e.g., including but not limited to one or more acoustic transducer element for the second ultrasound sensor assembly 712.

The clip band 703 is configured to secure the acoustic transducer elements 713 and the acoustic transducer elements 714 and position them in a fixed location with respect to each other. In some embodiments, the clip band 703 of the in vivo fluid flow sensor device 700 can include one or more openings 718 on at least one or both of the arms of the clip band 703 that allows for secondary attachment means of the device 700B to the target anatomic structure. For example, the openings 718 shown in the example of FIG. 7A include a portion of the clip band 703 between the two voids that are the openings 718, which provides an anchor site to apply a suture (e.g., stitch thread, wire, etc.) that affixes the arm of the clip band 703 to the anatomic structure (e.g., wall of the atrium of the heart).

In some embodiments of the in vivo fluid flow sensor device 700, like the example shown in FIG. 7A, the device 700 includes an inner curved region 734 of the distal ends of each arm of the clip band 703, e.g., which can assist in facilitating attachment and conformation to the anatomic structure upon placement as well as aid in delivery of the device 700, e.g., via a catheter The one or more openings 718 can be disposed on the inner curved region 734 and/or on the arm proximate the inner curved region 734 on at least one or both of the arms of the clip band 703, e.g., allowing for secondary attachment means of the device 700 to the target anatomic structure.

Figure 7B:
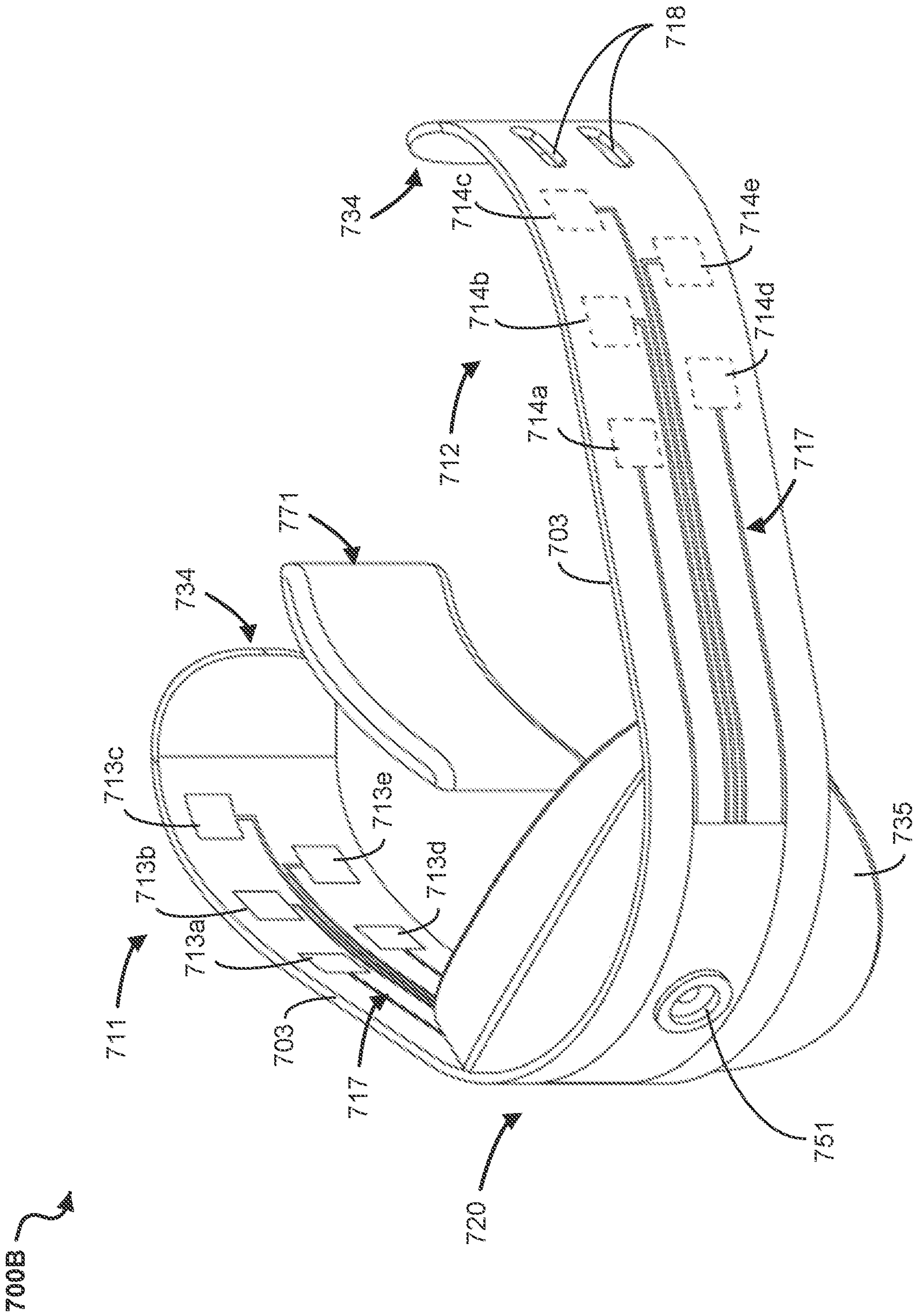
FIGS. 7B and 7C show diagrams depicting an example embodiment of the in vivo fluid flow sensor device of FIG. 1B, in accordance with the present technology.
Figure 7C:
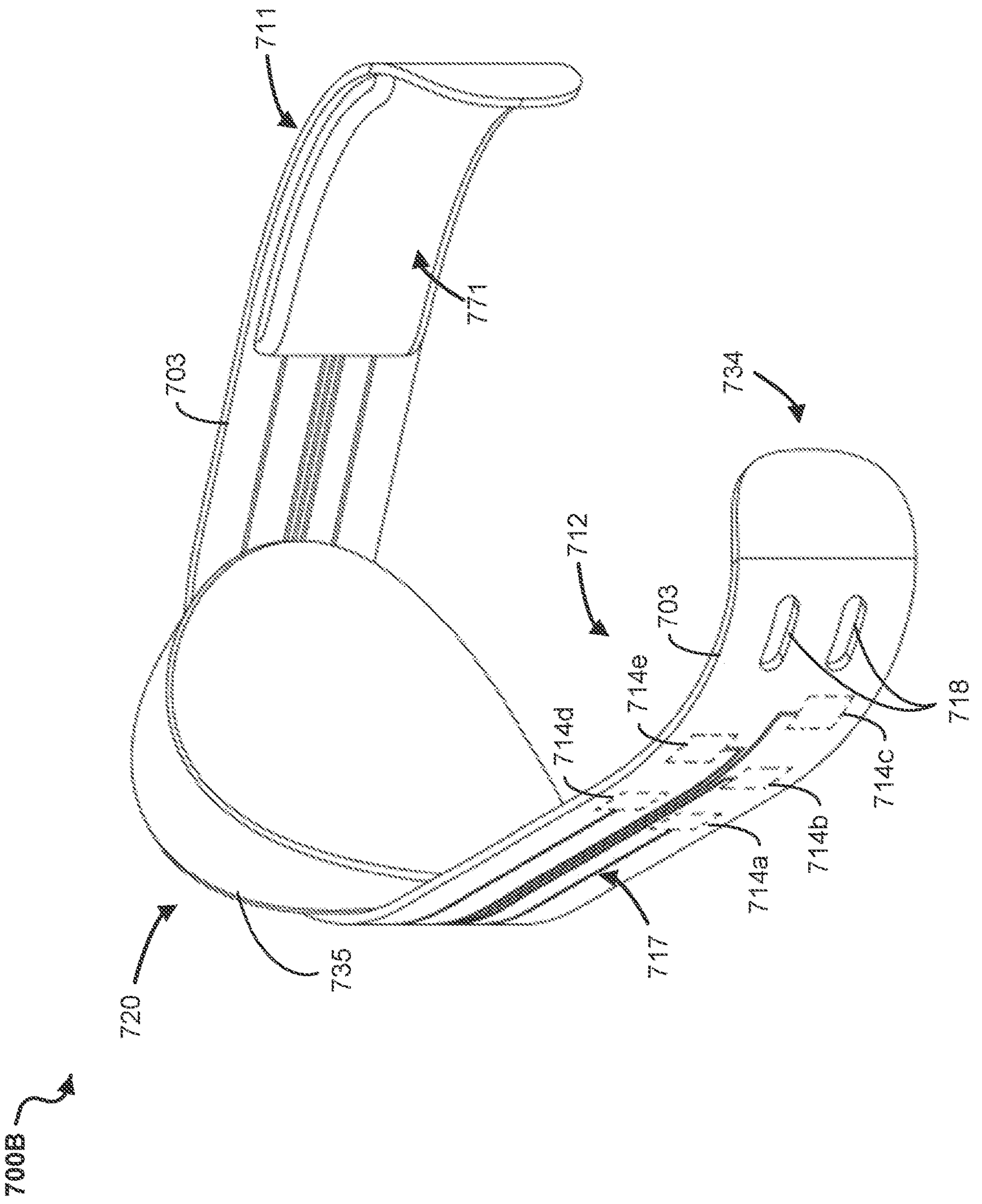

FIGS. 7B and 7C show diagrams depicting an example embodiment of the in vivo fluid flow sensor device 100B of FIG. 1B, shown in FIG. 7B and in FIG. 7C as in vivo fluid flow sensor device 700B. The in vivo fluid flow sensor device 700B can be configured similar to the in vivo fluid flow sensor device 700 (shown previously in FIG. 7A), e.g., where the sensor unit comprises the ultrasound sensor assembly 711 and/or the ultrasound sensor assembly 712 in electrical communication with an electronics unit 720 via the electrical interconnections 717 (e.g., coupled to or partially housed within arms of the clip band 703), and where the connection apparatus 735 includes the power and/or data port 751 in electrical communication with the electronics unit 720 and a remote device. Yet, as shown in shown in FIG. 7B and in FIG. 7C, the in vivo fluid flow sensor device 700B includes an acoustic transducer pad 771 to protect the acoustic transducers 713 and/or 714 and to improve acoustic signal at transmission and reception (e.g., improve acoustic impedance matching) between the transducers and the biological tissue of the anatomic structure to which the device 700 is attached. FIG. 7B shows the in vivo fluid flow sensor device 700B in an exploded view where the acoustic transducer pad 771 is detached from the ultrasound sensor assembly 711, and FIG. 7C shows the in vivo fluid flow sensor device 700B in a rotated view (with respect to FIG. 7B) but where the acoustic transducer pad 771 is coupled to the arm of the clip band 703 and/or (at least one of) the plurality of acoustic transducer elements 713 of the ultrasound sensor assembly 711 positioned on the arm of the clip band 703. While not shown in FIGS. 7B and 7C, a second acoustic transducer pad 771 may be coupled to the opposing arm of the clip band 703 and/or (at least one of) the plurality of acoustic transducer elements 714 of the ultrasound sensor assembly 712.

In various embodiments, the acoustic transducer pad 771 can comprise hydrogel, which may be packaged in a gelatin form, or a fluid form, with a casing comprising a polymer material having a hardness of up to 40 Å durometer (e.g., silicone, polyethylene, or other). In example implementations of the in vivo fluid flow sensor device 700 employing the acoustic transducer pad 771, the acoustic transducer pad 771 can further provide a contour and cushion against cardiac tissue, e.g., exterior tissue of the walls of the atrium or ventricle when the in vivo fluid flow sensor device 700 is deployed within the pericardium, as well as the epithelial tissue of the major blood vessel(s) such as the vena cava or pulmonary artery or vein. For example, the acoustic transducer pad 771 can account for contour variations with the anatomic structure the device 700 is directly interfaced with. Moreover, for example, the acoustic transducer pad 771 is operable to support signal isolation from noise and provide noise deflection for optimal sensing capability. The acoustic transducer pad 771 is able to reduce risk of damage from edge friability, e.g., by absorbing mechanical forces potentially incident upon the acoustic transducer elements during deployment and during operation (e.g., cycling motion of anatomic structure) that can lead to acute harm or long-term wear and tear, e.g., notably while not impacting the acoustic signal transfer between the anatomic structure and the acoustic transducer elements. Similarly, the acoustic transducer pad 771 is able to reduce the risk of tissue abrasion to the anatomic structure to preserve contact viability between the device and the biological tissue.

Figure 7D:
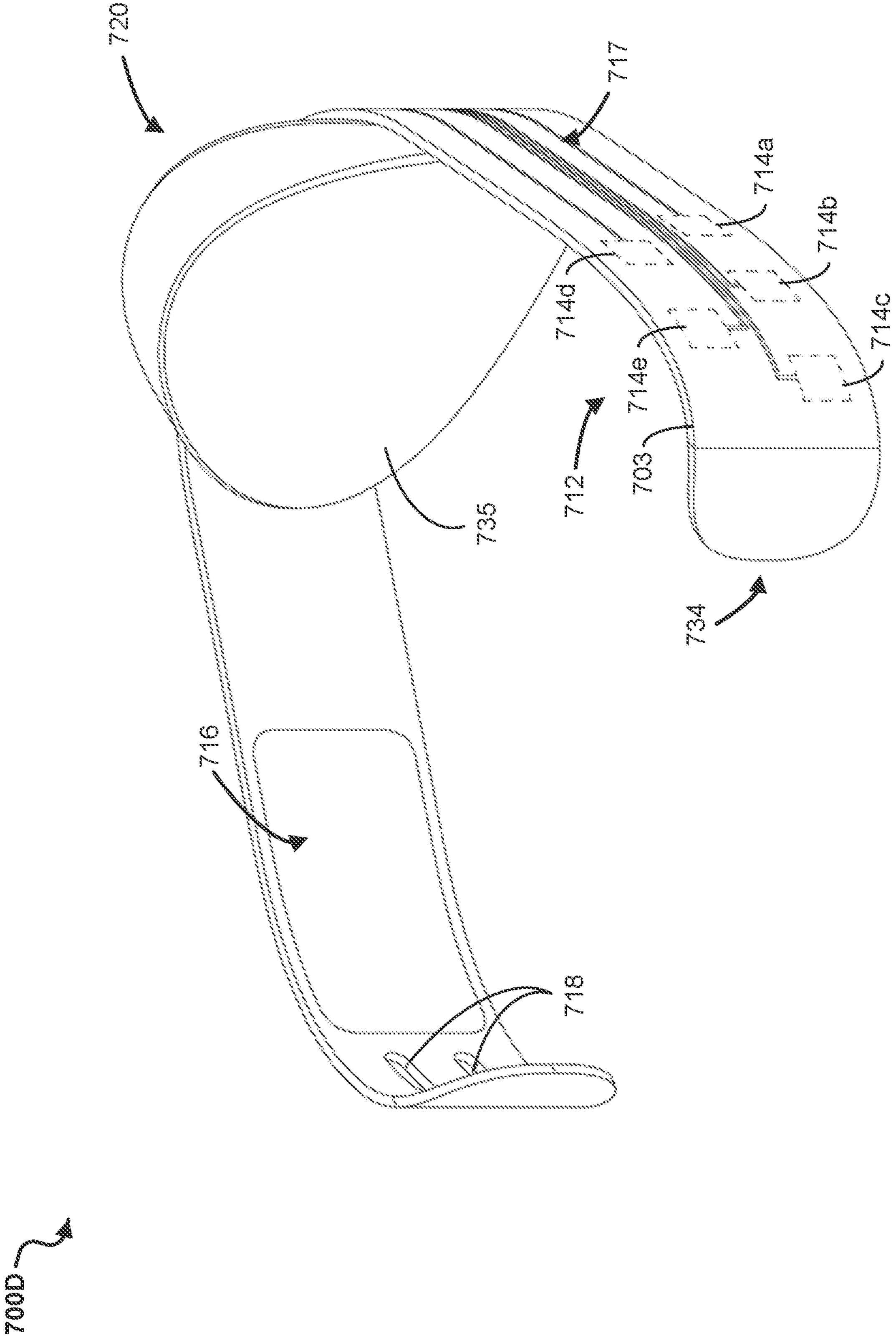
FIG. 7D shows a diagram depicting another example embodiment of the in vivo fluid flow sensor device of FIG. 1B, in accordance with the present technology.

FIG. 7D shows a diagram depicting an example embodiment of the in vivo fluid flow sensor device 100B of FIG. 1B, shown in FIG. 7D as in vivo fluid flow sensor device 700D. The in vivo fluid flow sensor device 700D can be configured similar to the in vivo fluid flow sensor device 700 (shown previously in FIG. 7A) and/or in vivo fluid flow sensor device 700B (shown previously in FIG. 7B and FIG. 7C, having at least one acoustic transducer pad 771), e.g., where the sensor unit comprises an ultrasound sensor assembly (shown in FIG. 7D as the ultrasound sensor assembly 712) in electrical communication with an electronics unit 720 via the electrical interconnections 717 (e.g., coupled to or partially housed within arms of the clip band 703), and where the connection apparatus 735 includes the power and/or data port 751 in electrical communication with the electronics unit 720 and a remote device. Yet, as shown in shown in FIG. 7D, the in vivo fluid flow sensor device 700D includes an embodiment of the reflector 516 (shown in FIG. 7D as reflector 716) configured to reflect acoustic signals transmitted by the ultrasound sensor assembly 712 that propagate across the anatomic structure, are affected by fluid flow through the anatomic structure, reflect from the reflector 716, and are received as returned acoustic signals by the ultrasound sensor assembly 712 (that correspond to the transmitted acoustic signals). In some embodiments, the reflector 716 may be attached to a backing or substrate (not shown), which may attach to the inner surface of the opposing arm of the clip band 703 to the arm that facilitates the ultrasound sensor assembly 712.

Figure 7E:
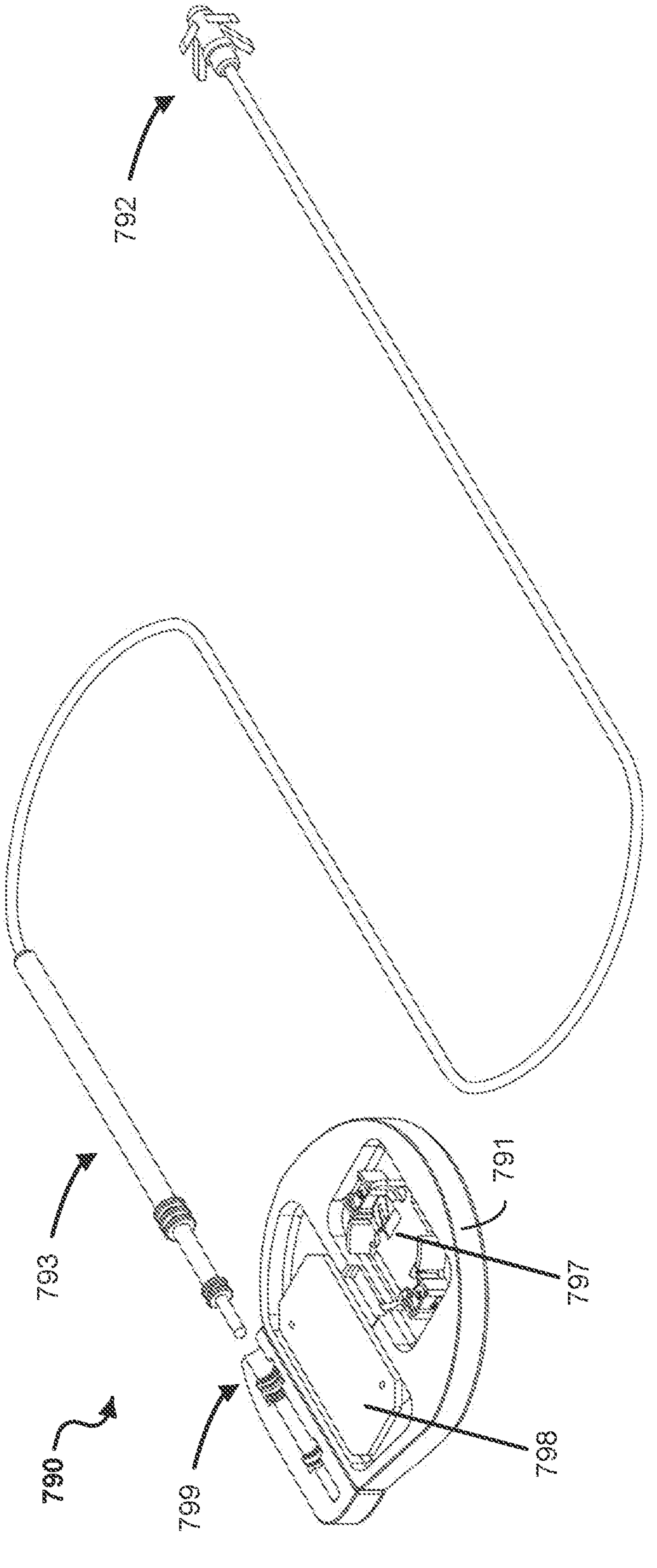
FIG. 7E shows a diagram of an example embodiment of a remote in vivo device that can tether to example embodiment of the in vivo fluid flow sensor device of FIG. 1B, such as the in vivo fluid flow sensor device of FIGS. 7A, 7B, 7C, and/or 7D.

FIG. 7E shows a diagram of an example embodiment of a remote in vivo device 790 operable to be in wired communication with an example embodiment of the in vivo fluid flow sensor device of FIG. 1B, such as the in vivo fluid flow sensor device 700, 700B, and/or 700D shown in FIGS. 7A, 7B-7C, and/or 7D, respectively. The remote in vivo device 790 includes a casing or housing 791, within which a power supply 798 and data processing and/or wireless communication unit 797 is housed.

Examples of the power supply 798 can include a battery, a fuel cell, or other electrical power source. In some embodiments, for example, the power supply 798 can be configured to be a replaceable battery and/or a rechargeable battery. For instance, in example implementations where the remote in vivo device 790 is located within the patient's body in an area or region that is relatively easy and safe for a clinician to access, e.g., such as the pleural cavity or a space in the abdominal area, the power supply 798 can be recharged. As such, the electrical energy stored in the power supply 798 can be used to supply the power supply in the electronics unit 720, which may have a relatively lower charge storage capacity than the power supply 798. The transfer of the electrical energy can be provided from the remote in vivo device 790 to the example in vivo fluid flow sensor device 700, 700B, 700D via a cable, wire, or cord 793 that interfaces with the power and/or data port 751 of the example in vivo fluid flow sensor device 700, 700B, 700D via an interfacing terminus 792. In the example illustration of FIG. 7E, the interfacing terminus 792 of the cable, wire, or cord 793 is shown to have at least one protruding structure, which can be used to create a locking system with the power and/or data port 751 to ensure securement (e.g., to avoid unwanted detachment of the cable, wire, or cord 793 in the patient's body from the example in vivo fluid flow sensor device 700, 700B, 700D).

Examples of the data processing and/or wireless communication unit 797 can include a transmitter, a receiver, and/or a transceiver with an antenna using a low power wireless communication protocol, e.g., such as Bluetooth Low Energy (BLE), Near Field Communication (NFC), low frequency radio frequency (RF) signal, in data communication with one or more processors coupled to a memory. In this manner, the data processing unit of the electronics unit 720 may manage data processing functions using less on-board power and offload more processing-intensive data processing tasks to the one or more processors and memory of the data processing and/or wireless communication unit 797. Moreover, the data processing and/or wireless communication unit 797 may serve to at least partially control certain device functions of the example in vivo fluid flow sensor device 700, 700B, 700D.

Figure 8A:
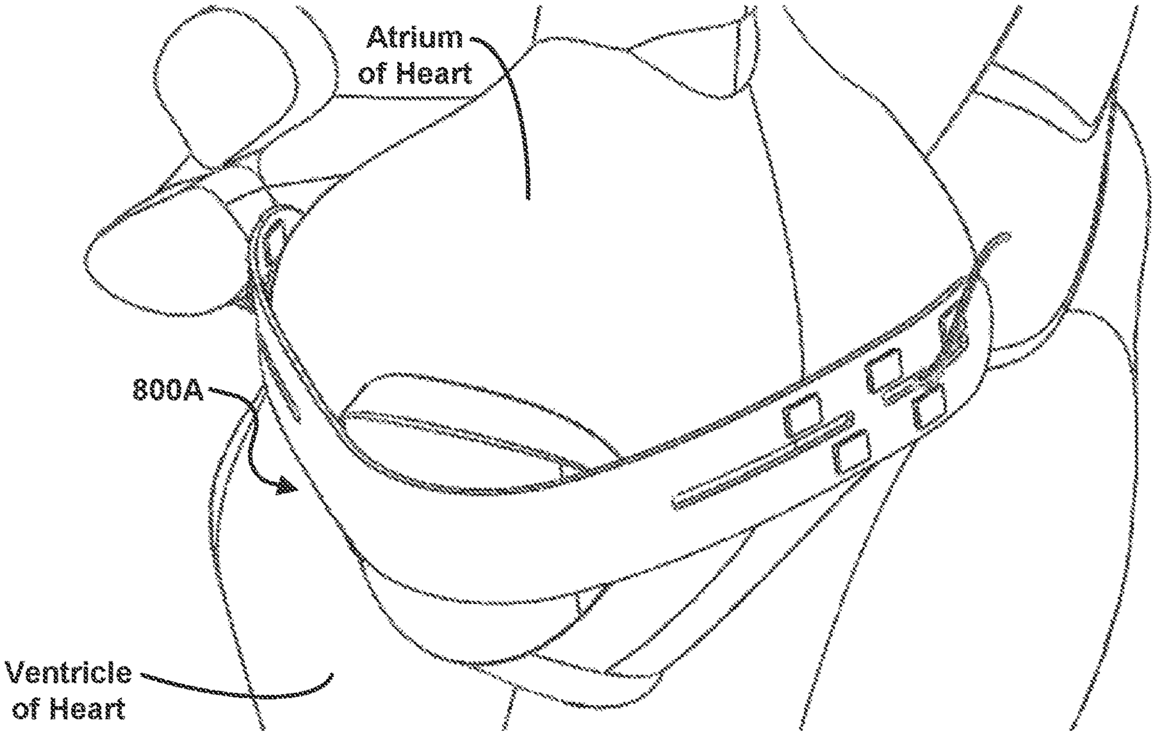
FIGS. 8A and 8B show diagrams illustrating an example embodiment of the in vivo fluid flow sensor device of FIG. 1B attached to a heart of a patient user in an example implementation of the device.
Figure 8B:
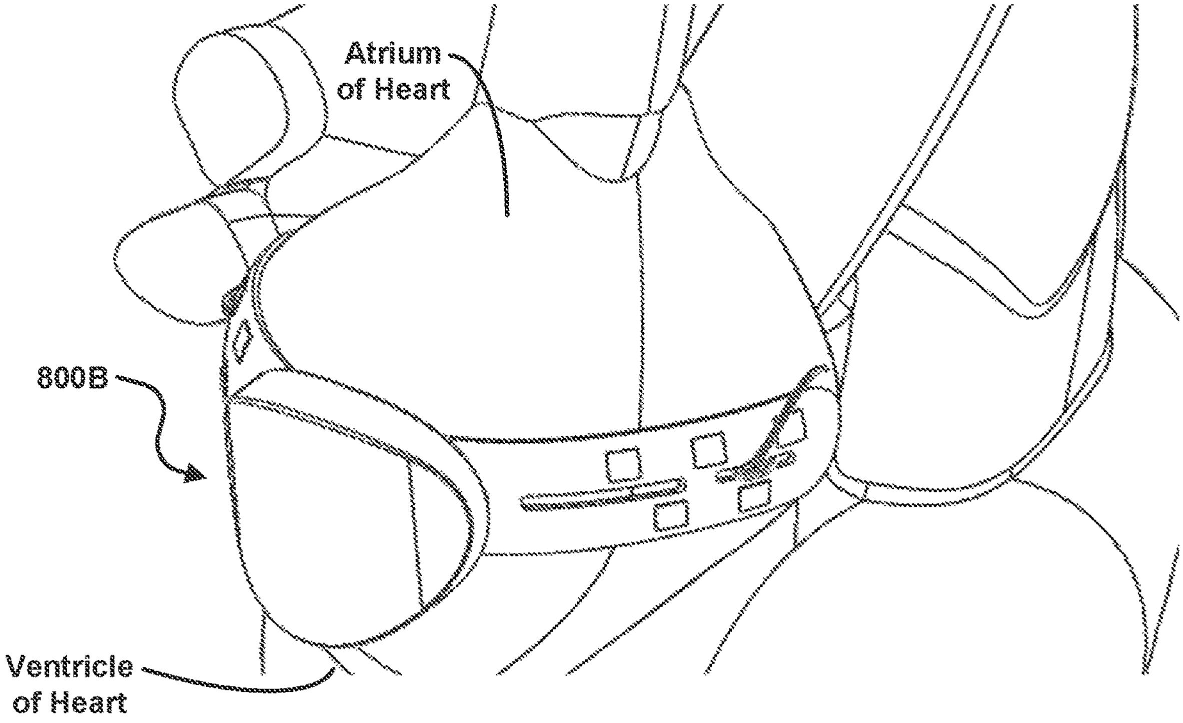

FIGS. 8A and 8B show diagrams illustrating an example embodiment of the in vivo fluid flow sensor device 100B of FIG. 1B, shown in FIGS. 8A and 8B as in vivo fluid flow sensor device 800A and 800B, respectively, where the in vivo fluid flow sensor device 800A, 800B is attached to a heart of a patient user in an example implementation of the device. In this example, the in vivo fluid flow sensor device 800A, 800B is configured to assess blood flow across the mitral valve, e.g., for assessing MR, by placing the ultrasound sensor assemblies on opposing sides of the external surface of the atrium of the heart about the mitral valve. As illustrated in FIGS. 8A and 8B, the arms of the in vivo fluid flow sensor device 800A and 800B (e.g., arms of an example embodiment of the linkage assembly 103 of device 100B as the clip band 603 and/or 703) are capable of extending about an organ, such as the atrium of the heart, with sufficient pliability that can support various orientations for optimizing functional alignment with the target anatomic structure.

Further, the optimal functional alignment can be preserved by the arms of the linkage assembly (e.g., degree of flex), which can position and secure the in vivo fluid flow sensor device 800A, 800B to the target anatomic structure individually or in compilation with (optional) one or more secondary attachment mechanisms, e.g., such as sutures (secured at suture ports), adhesives, or anchor structures (secured at anchoring ports), which can optimize the placement against the intended area of the organ/tissue for consistent measurements (e.g., initial monitoring to establish calibration, then comparison by constant monitoring and comparison from the baseline). Also, in some implementations, for example, multiple in vivo fluid flow sensor devices 800A, 800B can be deployed at different locations of the same anatomic structure.

The example embodiment of the in vivo fluid flow sensor device 800A includes the connection apparatus disposed on the inside of the clip band linkage assembly (e.g., proximate to the anatomic structure the device 800A is attached). Yet, the example embodiment of the in vivo fluid flow sensor device 800B includes the connection apparatus disposed on the outside of the clip band linkage assembly (e.g., distal from the anatomic structure the device 800B is attached). It is understood that the configuration of the connection apparatus can be on the inside or the outside of the linkage assembly for various embodiments of the in vivo fluid flow sensor device 100B, including any embodiment of the linkage assembly 103.

EXAMPLES

In some embodiments in accordance with the present technology (example A1), a sensor device for in vivo monitoring of fluid flow in an anatomic structure includes a first ultrasound assembly comprising a first set of one or more acoustic transducer elements; a second ultrasound assembly comprising a second set of one or more acoustic transducer elements; a first linkage coupled to the first ultrasound assembly; a second linkage coupled to the second ultrasound assembly; an electronics unit in electrical communication with the first ultrasound assembly and the second ultrasound assembly, the electronics unit configured to process the electrical signals associated with the returned acoustic signals as data and wirelessly transmit the data to an external processor; and a spring connection apparatus that couples to each of the first and second linkages and is operable to position the first ultrasound assembly at a first location on the anatomic structure and position the second ultrasound assembly at a second location on the anatomic structure to form a plane across the first and second locations of the anatomic structure to transmit and receive acoustic signals from the first set of one or more acoustic transducer elements and the second set of one or more acoustic transducer elements indicative of a fluid flow parameter of a biological fluid in the anatomic structure.

Example A2 includes the sensor device of any of examples A1-A4, wherein the anatomic structure is a heart.

Example A3 includes the sensor device of any of examples A1-A4, wherein the first location and the second location are positioned on a left atrium of the heart, and wherein the plane across which the acoustic signals are transmitted and received crosses at a mitral valve of the heart.

Example A4 includes the sensor device of any of examples A1-A3, wherein the first location and the second location are positioned on a right atrium of the heart, and wherein the plane across which the acoustic signals are transmitted and received crosses at a tricuspid valve of the heart.

In some embodiments in accordance with the present technology (example B1), a sensor device for in vivo monitoring of fluid flow in an anatomic structure includes a linkage assembly comprising a first arm configured to attach to a first portion of the anatomic structure and a second arm configured to attach to a second portion of the anatomic structure opposite to the first portion; a connection apparatus coupled to each of the first arm and the second arm; an ultrasound sensor assembly comprising a plurality of acoustic transducer elements coupled to the linkage assembly, the plurality of acoustic transducer elements including a first acoustic transducer element that is configured to transmit an acoustic signal to propagate through the anatomic structure and a second acoustic transducer element and a third acoustic transducer element that are configured to receive acoustic signals that have propagated through the anatomic structure and are indicative of a fluid flow parameter of a biological fluid in the anatomic structure; and an electronics unit housed in the connection apparatus and in electrical communication with the plurality of acoustic transducer elements of the ultrasound sensor assembly, the electronics unit configured to process electrical signals associated with the received acoustic signals as data and wirelessly transmit the data to an external processor.

Example B2 includes the sensor device of any of examples B1-B50, wherein the ultrasound sensor assembly includes a first ultrasound sensor assembly disposed on the first arm of the linkage assembly and a second ultrasound sensor assembly disposed on the second arm of the linkage assembly.

Example B3 includes the sensor device of example B2 or any of examples B1-B50, wherein the first ultrasound sensor assembly includes the first acoustic transducer element configured to transmit the acoustic signal that is positioned on a distal region of the first arm to interface with the first portion of the anatomic structure, wherein the second ultrasound sensor assembly includes the second and third acoustic transducer elements configured to receive the acoustic signals that are positioned on a distal region of the second arm to interface with the second portion of the anatomic structure, and wherein a first center point ($C_{Tx}$) of the first acoustic transducer element is aligned with a second center point ($Cd_{Rx}$) located between a distance (d) separating centers of the second acoustic transducer element and the third acoustic transducer element.

Example B4 includes the sensor device of example B2 or any of examples B1-B50, wherein the first ultrasound sensor assembly includes the first acoustic transducer element configured to transmit the acoustic signal that is positioned on a distal region of the first arm to interface with the first portion of the anatomic structure, wherein the second ultrasound sensor assembly includes the second and third acoustic transducer elements configured to receive the acoustic signals that are positioned on a distal region of the second arm to interface with the second portion of the anatomic structure, wherein the first ultrasound sensor assembly further includes a fourth acoustic transducer element and a fifth acoustic transducer element positioned on the distal region of the second arm to interface with the second portion of the anatomic structure and configured to receive a first set of acoustic signals associated with transmission of the acoustic signal by the first acoustic transducer element, wherein the second ultrasound sensor assembly includes a sixth acoustic transducer element positioned on the distal region of the first arm to interface with the first portion of the anatomic structure and configured to transmit a second acoustic signal associated with the acoustic signals received at the second and third acoustic transducer elements, and wherein a first center point ($C_{Tx1}$) of the first acoustic transducer element is aligned with a second center point ($Cd_{Rx1}$) located between a first distance (d1) separating centers of the fourth acoustic transducer element and the fifth acoustic transducer element, and wherein a third center point ($C_{Tx2}$) of the sixth acoustic transducer element is aligned with a fourth center point ($Cd_{Rx2}$) located between a second distance (d2) separating centers of the second acoustic transducer element and the third acoustic transducer element.

Example B5 includes the sensor device of any of examples B1-B50, wherein the plurality of acoustic transducer elements of the ultrasound sensor assembly is disposed on the first arm of the linkage assembly, and wherein the sensor device further comprises a reflector disposed on the second arm of the linkage assembly.

Example B6 includes the sensor device of any of examples B1-B50, wherein at least one of the first acoustic transducer element, the second transducer element, or the third acoustic transducer element is configured to have a size dimension between 1 mm to 4 mm.

Example B7 includes the sensor device of any of examples B1-B50, wherein the ultrasound sensor assembly further comprises a substrate connected to an interior-facing surface of at least one of the first arm or the second arm of the linkage assembly and that couples at least one of the plurality of acoustic transducer elements.

Example B8 includes the sensor device of example B7 or any of examples B1-B50, wherein the substrate is configured to provide a heat sync for management of thermal generation by the at least one acoustic transducer element.

Example B9 includes the sensor device of any of examples B1-B50, wherein at least one of the plurality of acoustic transducer elements includes a piezoelectric micro-machined ultrasonic transducer (PMUT).

Example B10 includes the sensor device of any of examples B1-B50, wherein the sensor device further comprises an acoustic transducer pad that couples to at least some of the acoustic transducer elements of the ultrasound sensor assembly and is configured to provide a contour and cushion against the anatomic structure.

Example B11 includes the sensor device of example B10 or any of examples B1-B50, wherein the acoustic transducer pad includes a hydrogel.

Example B12 includes the sensor device of any of examples B1-B50, wherein the linkage assembly is operable to secure the sensor device to the anatomic structure with pliability for the sensor device to be stable in its placement with respect to the anatomic structure while withstanding continuous movements of the anatomic structure to which its attached.

Example B13 includes the sensor device of example B12 or any of examples B1-B50, wherein the linkage assembly includes a clip band operable to provide a compression force by each of the first arm and the second arm of the clip band to facilitate securement of the sensor device to the first portion and the second portion of the anatomic structure and to absorb forces applied onto the first arm and the second arm of the clip band by the anatomic structure due to the continuous movements of the anatomic structure.

Example B14 includes the sensor device of example B13 or any of examples B1-B50, wherein the clip band comprises a composite material having a polymer component that is flexible and a shape-stiffener component that is pre-shaped and is capable of undergoing a shape change.

Example B15 includes the sensor device of example B14 or any of examples B1-B50, wherein the shape-stiffener component of the composite material comprises one or more of Nitinol, gold, platinum, or iridium, which is encased in the polymer component of the composite material that comprises one or more of silicone, polyethylene, polyimide, polyamide, or a blend thereof.

Example B16 includes the sensor device of any of examples B1-B50, wherein the connection apparatus is operable to secure the linkage assembly to the anatomic structure with mechanical resilience for the sensor device to be stable in its placement with respect to the anatomic structure while withstanding continuous movements of the anatomic structure to which its attached.

Example B17 includes the sensor device of example B16 or any of examples B1-B50, wherein the connection apparatus includes a spring operable to provide a compression force upon each of the first arm and the second arm of the linkage assembly to facilitate securement of the sensor device to the first portion and the second portion of the anatomic structure and to absorb forces applied onto the first arm and the second arm of the linkage assembly by the anatomic structure due to the continuous movements of the anatomic structure.

Example B18 includes the sensor device of any of examples B1-B50, wherein the electronics unit comprises a power supply and a wireless communications unit including a wireless transmitter or wireless transceiver.

Example B19 includes the sensor device of example B18 or any of examples B1-B50, wherein the power supply includes at least one of a battery or a fuel cell.

Example B20 includes the sensor device of example B18 or any of examples B1-B50, wherein the electronics unit comprises a signal conditioning unit in communication with the plurality of acoustic transducer elements of the ultrasound sensor assembly via one or more electrical interface components, the signal conditioning unit comprising an electrical circuit configured to process the electrical signals associated with the received acoustic signals by one or more of amplifying the electrical signals, filtering the electrical signals, or converting the electrical signals from analog to digital.

Example B21 includes the sensor device of example B20 or any of examples B1-B50, wherein the electronics unit comprises a data processing unit in communication with the signal conditioning unit, the data processing unit comprising a processor and a memory and configured to process the amplified, filtered, or converted electrical signals as the data representative of the fluid flow parameter of the biological fluid.

Example B22 includes the sensor device of example B18 or any of examples B1-B50, wherein the electronics unit comprises a data processing unit in communication with the wireless communications unit, the data processing unit comprising a processor and a memory and configured to process the electrical signals as the data representative of the fluid flow parameter of the biological fluid.

Example B23 includes the sensor device of example B18 or any of examples B1-B50, wherein the electronics unit comprises a printed circuit board (PCB) having a substrate and electrical interconnections disposed on the substrate, wherein the electrical interconnections are coupled to a plurality of electrical interconnection wires that span between the plurality of acoustic transducer elements of the ultrasound sensor assembly and the PCB of the electronics unit.

Example B24 includes the sensor device of example B23 or any of examples B1-B50, wherein the electronics unit comprises a casing that encompasses the electronics unit to protect the electronics unit from exposure to a body fluid when the sensor device is inserted and deployed in vivo.

Example B25 includes the sensor device of example B24 or any of examples B1-B50, wherein the casing includes one or both of flat sides or curved sides to provide a form factor of the sensor device, including at least one of rectangular, a cylindrical, a conical, an elliptical, a pyramidal, a trapezoidal, or a non-uniform shape.

Example B26 includes the sensor device of example B24 or any of examples B1-B50, wherein the casing includes is coupled to the linkage assembly on an inward-facing surface of the linkage assembly that faces toward the anatomic structure, or wherein the casing includes is coupled to the linkage assembly on an outward-facing surface of the linkage assembly that faces away from the anatomic structure.

Example B27 includes the sensor device of example B24 or any of examples B1-B50, wherein the PCB of the electronics unit is hermetically sealed within the casing by a non-permeable material that covers the PCB to provide an electrical shield from the body fluid.

Example B28 includes the sensor device of example B27 or any of examples B1-B50, wherein the non-permeable material includes at least one of a parylene, a urethane, or a Teflon material.

Example B29 includes the sensor device of any of examples B1-B50, further comprising a secondary sensor coupled to at least one of the linkage assembly or the connection apparatus and in communication with the electronics unit, the secondary sensor operable to measure one or more of a biological parameter, a physiological parameter, an electrophysiological parameter, or a physical parameter of the body within which the sensor device is deployed.

Example B30 includes the sensor device of example B29 or any of examples B1-B50, wherein the secondary sensor includes an analyte sensor configured to detect an analyte of the biological fluid in the anatomic structure or of a body fluid in a region proximate the anatomic structure where the sensor device is deployed.

Example B31 includes the sensor device of example B29 or any of examples B1-B50, wherein the secondary sensor includes a pH sensor configured to detect a pH level of the biological fluid in the anatomic structure or of a body fluid in a region proximate the anatomic structure where the sensor device is deployed.

Example B32 includes the sensor device of example B29 or any of examples B1-B50, wherein the secondary sensor includes a temperature sensor configured to detect temperature of the biological fluid in the anatomic structure or of a body fluid in a region proximate the anatomic structure where the sensor device is deployed.

Example B33 includes the sensor device of example B29 or any of examples B1-B50, wherein the secondary sensor includes an inertial measurement unit (IMU) configured to detect motion of the sensor device in multiple degrees of freedom.

Example B34 includes the sensor device of any of examples B1-B50, further comprising a secondary attachment component comprising one or more of a suture, a prong, a screw, a barb, an adhesive, or a grasping mechanism disposed on at least one portion of the linkage assembly and configured to secure the to the ultrasound sensor assembly via the linkage assembly to the anatomic structure.

Example B35 includes the sensor device of any of examples B1-B50, wherein the linkage assembly is capable of changing shape from a first shape conformation, where the first arm and the second arm of the linkage assembly spread outward from a centerline through at least one of the linkage assembly or the connection apparatus, to be insertable into a body of a patient, to a second shape conformation, where the first arm and the second arm of the linkage assembly span inward toward the centerline through at least one of the linkage assembly or the connection apparatus, to be attachable to the anatomic structure for operation of the sensor device.

Example B36 includes the sensor device of any of examples B1-B50, further comprising a second linkage assembly comprising a third arm configured to attach to a third portion of the anatomic structure and a fourth arm configured to attach to a fourth portion of the anatomic structure opposite to the third portion, wherein the connection apparatus is coupled to each of the third arm and the fourth arm, and wherein the ultrasound sensor assembly comprises an additional set of the plurality of acoustic transducer elements coupled to the second linkage assembly and configured to transmit a second acoustic signal to propagate through the anatomic structure across the third portion and the fourth portion and to receive a second set of acoustic signals that have propagated through the anatomic structure across the third portion and the fourth portion and are indicative of a second fluid flow parameter of the biological fluid in the anatomic structure.

Example B37 includes the sensor device of any of examples B1-B50, wherein the connection apparatus includes a port in electrical communication with the electronics unit housed in the connection apparatus and operable to electrically couple to a remote power supply housed in a remote device via at least one of a cable, wire, or cord, wherein the remote device is located in another location different than and at a distance from the anatomic structure.

Example B38 includes the sensor device of example B37 or any of examples B1-B50, wherein the port is in data communication with the electronics unit housed in the connection apparatus and operable to interface the electronics unit to a data processing unit disposed in the remote device via the at least one of the cable, wire, or cord to output the data from the electronics unit of the sensor device to the data processing unit of the remote device through the port via the at least one of the cable, wire, or cord.

Example B39 includes the sensor device of example B38 or any of examples B1-B50, wherein the sensor device is configured to wirelessly transmit the data by a secondary transmission device comprising a wireless transmitter or transceiver to the external processor.

Example B40 includes the sensor device of example B37 or any of examples B1-B50, wherein the other location where the remote device is located is at least 2 cm from the anatomic structure.

Example B41 includes the sensor device of example B37 or any of examples B1-B50, wherein the other location includes a pleural cavity, a cavity in the abdominal space, a subcutaneous space, or an outer-body location.

Example B42 includes the sensor device of any of examples B1-B50, wherein the external processor that is able to receive the data to be wirelessly transmitted by the electronics unit of the sensor device is located outside of the body of a patient user to which the sensor device is implantable and deployable at the anatomic structure.

Example B43 includes the sensor device of any of examples B1-B50, wherein the fluid flow parameter of the biological fluid in the anatomic structure includes at least one of a flow rate, or an amount of pressure difference between ends of a flow path in the anatomic structure.

Example B44 includes the sensor device of example B43 or any of examples B1-B50, wherein the device is operable to detect a size dimension of the anatomic structure or a predictive area or volume of the anatomic structure based on a baseline measurement of the flow rate and changes in the flow rate over time.

Example B45 includes the sensor device of any of examples B1-B50, wherein the anatomic structure is a heart, and the biological fluid is blood.

Example B46 includes the sensor device of example B45 or any of examples B1-B50, wherein the sensor device is deployable within at least one layer of the pericardium of the heart, or wherein the sensor device is deployable on an external layer of the pericardium of the heart.

Example B47 includes the sensor device of example B45 or any of examples B1-B50, wherein the first arm and the second arm of the linkage assembly are positioned on opposing portions of a left atrium of the heart, and wherein the received acoustic signals are indicative of blood flow at a mitral valve of the heart.

Example B48 includes the sensor device of example B45 or any of examples B1-B50, wherein the first arm and the second arm of the linkage assembly are positioned on opposing portions of a right atrium of the heart, and wherein the received acoustic signals are indicative of blood flow at a tricuspid valve of the heart.

Example B49 includes the sensor device of example B45 or any of examples B1-B50, wherein the first arm and the second arm of the linkage assembly are positioned on a superior vena cava or an inferior vena cava proximate the heart, and wherein the received acoustic signals are indicative of blood flow at the superior vena cava or the inferior vena cava.

Example B50 includes the sensor device of example B45 or any of examples B1-B49, wherein the first arm and the second arm of the linkage assembly are positioned on a pulmonary artery or pulmonary vein proximate the heart, and wherein the received acoustic signals are indicative of blood flow at the pulmonary artery or the pulmonary vein.

In some embodiments in accordance with the present technology (example B51), a sensor device for in vivo monitoring of blood flow in a heart or blood vessel leading into or out of the heart in a body of a patient, includes, a linkage assembly comprising a first arm configured to attach to a first portion of the heart or the blood vessel and a second arm configured to attach to a second portion of the heart or the blood vessel; a connection apparatus coupled to each of the first arm and the second arm; an ultrasound sensor assembly comprising a plurality of acoustic transducer elements coupled to the linkage assembly, the plurality of acoustic transducer elements including a first acoustic transducer element that is configured to transmit an acoustic signal to propagate through the heart or the blood vessel and a second acoustic transducer element and a third acoustic transducer element that are configured to receive acoustic signals that have propagated through the heart or the blood vessel and are indicative of a fluid flow parameter of the blood that flows in the heart or blood vessel; and an electronics unit housed in the connection apparatus and in electrical communication with the plurality of acoustic transducer elements of the ultrasound sensor assembly, the electronics unit configured to process electrical signals associated with the received acoustic signals as data and wirelessly transmit the data to an external processor, wherein the linkage assembly includes a clip band operable to provide a compression force by each of the first arm and the second arm of the clip band to facilitate securement of the sensor device to the first portion and the second portion of the heart or the blood vessel and to absorb forces applied onto the first arm and the second arm of the clip band by heartbeats or changes in size of the heart or the blood vessel.

Example B52 includes the sensor device of any of examples B51-B60, wherein the clip band comprises a composite material having a polymer component that is flexible and a shape-stiffener component that is pre-shaped and is capable of undergoing a shape change.

Example B53 includes the sensor device of example B52 or any of examples B51-B60, wherein the shape-stiffener component of the composite material comprises one or more of Nitinol, gold, platinum, or iridium, which is encased in the polymer component of the composite material that comprises one or more of silicone, polyethylene, polyimide, polyamide, or a blend thereof.

Example B54 includes the sensor device of any of examples B51-B60, wherein the ultrasound sensor assembly includes a first ultrasound sensor assembly disposed on the first arm of the clip band and a second ultrasound sensor assembly disposed on the second arm of the clip band, or wherein the plurality of acoustic transducer elements of the ultrasound sensor assembly is disposed on the first arm of the clip band, and wherein the sensor device further comprises a reflector disposed on the second arm of the clip band.

Example B55 includes the sensor device of any of examples B51-B60, wherein the sensor device further comprises an acoustic transducer pad comprising a hydrogel that couples to at least some of the acoustic transducer elements of the ultrasound sensor assembly and is configured to provide a contour and cushion against the heart or the blood vessel.

Example B56 includes the sensor device of any of examples B51-B60, wherein the sensor device is deployable within at least one layer of the pericardium of the heart, or wherein the sensor device is deployable on an external layer of the pericardium of the heart.

Example B57 includes the sensor device of any of examples B51-B60, wherein the first arm and the second arm of the clip band are positioned on opposing portions of a left atrium of the heart, and wherein the received acoustic signals are indicative of the blood flow at a mitral valve of the heart.

Example B58 includes the sensor device of any of examples B51-B60, wherein the first arm and the second arm of the clip band are positioned on opposing portions of a right atrium of the heart, and wherein the received acoustic signals are indicative of the blood flow at a tricuspid valve of the heart.

Example B59 includes the sensor device of any of examples B51-B60, the first arm and the second arm of the clip band are positioned on a superior vena cava or an inferior vena cava proximate the heart, and wherein the received acoustic signals are indicative of the blood flow at the superior vena cava or the inferior vena cava.

Example B60 includes the sensor device of any of examples B51-B59, wherein the first arm and the second arm of the clip band are positioned on a pulmonary artery or pulmonary vein proximate the heart, and wherein the received acoustic signals are indicative of the blood flow at the pulmonary artery or the pulmonary vein.

In some embodiments in accordance with the present technology (example B61), a system for in vivo monitoring of fluid flow in an anatomic structure includes an in vivo sensor device operable to be deployed in a body of a patient user and attached to the anatomic structure, and a data processing system in data communication with the in vivo sensor device. The in vivo sensor device includes a linkage assembly comprising a first arm configured to attach to a first portion of the anatomic structure and a second arm configured to attach to a second portion of the anatomic structure opposite to the first portion; a connection apparatus coupled to each of the first arm and the second arm; an ultrasound sensor assembly comprising a plurality of acoustic transducer elements coupled to the linkage assembly, the plurality of acoustic transducer elements including a first acoustic transducer element that is configured to transmit an acoustic signal to propagate through the anatomic structure and a second acoustic transducer element and a third acoustic transducer element that are configured to receive acoustic signals that have propagated through the anatomic structure and are indicative of a fluid flow parameter of a biological fluid in the anatomic structure; and an electronics unit housed in the connection apparatus and in electrical communication with the plurality of acoustic transducer elements of the ultrasound sensor assembly, the electronics unit configured to process electrical signals associated with the received acoustic signals as data and wirelessly transmit the data to an external processor. The data processing system includes a processor and a memory and is configured to receive the data from the in vivo sensor device and process the received data to determine the fluid flow parameter associated with the biological fluid in the anatomic structure.

Example B62 includes the sensor device of any of examples B61-B72, wherein the in vivo sensor device includes one or more features associated with the sensor device recited in any of examples B1-B50 and/or any of examples B51-B60.

Example B63 includes the sensor device of any of examples B61-B72, further comprising a remote in vivo intermediary device comprising a power supply, a wireless communication unit that includes at least one of a transmitter or a transceiver, and a data processing unit that includes a data processor and a data memory, wherein the remote in vivo intermediary device is in wireless or wired communication with the in vivo sensor device and is located in another location of the body different than and at a distance from the anatomic structure.

Example B64 includes the sensor device of example B63 or any of examples B61-B72, wherein the in vivo sensor device is in wired communication with the remote in vivo intermediary device via at least one of a cable, wire, or cord that couples to a port of the connection apparatus of the in vivo sensor device that is in electrical communication with the electronics unit of the in vivo sensor device, and wherein the remote in vivo intermediary device is operable to supply electrical energy stored in the power supply to the electronics unit of the in vivo sensor device.

Example B65 includes the sensor device of example B63 or any of examples B61-B72, wherein the remote in vivo intermediary device is operable to interface the electronics unit of the in vivo sensor device to the data processing unit disposed in the remote in vivo intermediary device to process the data and to determine the fluid flow parameter associated with the biological fluid in the anatomic structure.

Example B66 includes the sensor device of example B63 or any of examples B61-B72, wherein the remote in vivo intermediary device is operable to interface the electronics unit of the in vivo sensor device to the wireless communications unit disposed in the remote in vivo intermediary device to wirelessly transmit the data directly or indirectly to the data processing system.

Example B67 includes the sensor device of example B63 or any of examples B61-B72, wherein the other location where the remote device is located is at least 2 cm from the anatomic structure.

Example B68 includes the sensor device of example B63 or any of examples B61-B72, wherein the other location includes a pleural cavity, a cavity in an abdominal space, a subcutaneous space, or an outer-body location.

Example B69 includes the sensor device of any of examples B61-B72, wherein the data processing system includes a server computer comprising the processor and the memory and one or more databases in data communication with the server computer, wherein the data processing system is configured to remotely monitor data associated with the patient user obtained by the sensor device.

Example B70 includes the sensor device of any of examples B61-B72, further comprising a receiver device, comprising a data processor and a data memory, operable to (i) receive a wireless transmission carrying data indicative of the electrical signal acquired from the sensor device and (ii) transmit the data to the data processing system.

Example B71 includes the sensor device of example B64 or any of examples B61-B72, wherein the receiver device is configured to store the data in the memory of the receiver device, and/or wherein the receiver device is in communication with the data processing system via a network of computers in communication with each other and accessible through the Internet.

Example B72 includes the sensor device of any of examples B61-B71, further comprising a remote client computing device, comprising a data processor and a data memory, in data communication with the data processing system and configured to receive processed data that is selected, filtered, and/or formatted by the data processing system.

In some embodiments in accordance with the present technology (example B73), a sensor device for in vivo monitoring of a cardiac function includes a linkage assembly comprising a first arm configured to attach to a first external portion of a heart, and an optional second arm that may be configured to attach to a second external portion of the heart; a housing coupled to the linkage assembly; a sensor assembly coupled to the first arm and configured to detect a functional parameter of the heart; and an electronics unit disposed in the housing and in electrical communication with the sensor assembly, the electronics unit configured to process electrical signals associated with the detected functional parameter as data and wirelessly transmit the data to an external processor.

Example B74 includes the sensor device of any of examples B73-B76, wherein the sensor device is deployable within at least one layer of the pericardium of the heart, or wherein the sensor device is deployable on an external layer of the pericardium of the heart.

Example B75 includes the sensor device of any of examples B73-B76, wherein the sensor assembly comprises at least one of an accelerometer, a gyroscope, a magnetometer, an acoustic transducer, a temperature sensor, an analyte sensor, or a pH sensor.

Example B76 includes the sensor device of any of examples B73-B76, wherein the sensor device includes one or more features associated with the sensor device recited in any of examples B1-B50 and/or any of examples B51-B60.

CONCLUSION

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms “a”, “an” and “the” are intended to include the plural forms as well, unless the context clearly indicates otherwise. Additionally, the use of “or” is intended to include “and/or”, unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An implantable sensor device for in vivo monitoring of blood flow in a blood vessel, comprising:

a first arm configured to attach to a first exterior portion of the blood vessel and a second arm configured to attach to a second exterior portion of the blood vessel;

a connection apparatus coupled to each of the first arm and the second arm;

an ultrasound sensor assembly comprising a first ultrasound sensor assembly and a second ultrasound sensor assembly;

the first ultrasound sensor assembly comprising a first set of one or more acoustic transducer elements coupled to the first arm;

the second ultrasound sensor assembly comprising a second set of one or more acoustic transducer elements coupled to the second arm;

wherein one or both of the first set of one or more acoustic transducer elements and the second set of one or more acoustic transducer elements include at least one of a first acoustic transducer element that is configured to transmit an acoustic signal to propagate through the blood vessel or a second acoustic transducer element configured to receive acoustic signals that have propagated through the blood vessel and are indicative of a fluid flow parameter of blood in the blood vessel; and wherein at least one of the first set or the second set of the one or more acoustic transducer elements includes a piezoelectric micromachined ultrasonic transducer (PMUT).

2. The sensor device of claim 1, wherein the sensor device further comprises a reflector disposed on one or both of the first arm and the second arm.

3. The sensor device of claim 1, wherein at least one of the first acoustic transducer element, the second acoustic transducer element, or a third acoustic transducer element is configured to have a size dimension between 1 mm to 4 mm.

4. The sensor device of claim 1, wherein the ultrasound sensor assembly further comprises a substrate connected to an interior-facing surface of at least one of the first arm or the second arm and that couples at least one of the first set or the second set of one or more acoustic transducer elements.

5. The sensor device of claim 4, wherein the substrate is configured to provide a heat sync for management of thermal generation by the at least one of the first set or the second set of one or more acoustic transducer elements.

6. The sensor device of claim 1, wherein the sensor device further comprises an acoustic transducer pad that couples to at least some of the acoustic transducer elements of the ultrasound sensor assembly and is configured to provide a contour and cushion against the exterior portion of the blood vessel.

7. The sensor device of claim 6, wherein the acoustic transducer pad includes a hydrogel.

8. The sensor device of claim 1, wherein the first arm and the second arm are operable to secure the sensor device to the exterior portion of the blood vessel with pliability for the sensor device to be stable in its placement with respect to the blood vessel while withstanding continuous movements of the blood vessel to which its attached.

9. The sensor device of claim 8, wherein at least one of the first arm or the second arm comprises a shape-stiffener component that is pre-shaped and is capable of undergoing a shape change.

10. The sensor device of claim 9, wherein the shape-stiffener component comprises one or more of Nitinol, gold, platinum, or iridium.

11. The sensor device of claim 1, further comprising:

an electronics unit housed in the connection apparatus and in electrical communication with the first ultrasound sensor assembly and the second ultrasound sensor assembly, the electronics unit configured to process electrical signals associated with the received acoustic signals as data and wirelessly transmit the data to an external processor;

wherein the electronics unit comprises a processor; a memory in data communication with the processor; a wireless communications unit, including a wireless transmitter or wireless transceiver, in data communication with one or both of the processor and the memory; and a power supply in electrical connection with the processor, the memory, and the wireless communication unit.

12. The sensor device of claim 11, wherein the electronics unit further comprises one or more electrical interface components electrically coupled to the acoustic transducer elements; and a signal conditioning unit in communication with the acoustic transducer elements of the ultrasound sensor assembly via the one or more electrical interface components, the signal conditioning unit comprising an electrical circuit having at least one amplifier and configured to process the electrical signals associated with the received acoustic signals by one or more of amplifying the electrical signals, filtering the electrical signals, or converting the electrical signals from analog to digital.

13. The sensor device of claim 12, wherein the electronics unit comprises a data processing unit in communication with the signal conditioning unit, the data processing unit comprising the processor and the memory and configured to process the amplified, filtered, or converted electrical signals as the data representative of the flow of blood in the blood vessel.

14. The sensor device of claim 1, further comprising:

an electronics unit housed in the connection apparatus and in electrical communication with the first ultrasound sensor assembly and the second ultrasound sensor assembly, the electronics unit configured to process electrical signals associated with the received acoustic signals as data and wirelessly transmit the data to an external processor;

wherein the electronics unit comprises a casing that encompasses the electronics unit to protect the electronics unit from exposure to a body fluid when the sensor device is inserted and deployed in vivo.

15. The sensor device of claim 14, further comprising:

a secondary sensor coupled to at least one of the first arm, the second arm, or the connection apparatus and in communication with the electronics unit, the secondary sensor operable to measure one or more of a biological parameter, a physiological parameter, an electrophysiological parameter, or a physical parameter of a body of a patient within which the sensor device is deployed.

16. The sensor device of claim 1, further comprising:

a secondary attachment component disposed on one or both of the first arm and the second arm and configured to secure the sensor device to the blood vessel.

17. The sensor device of claim 1, wherein each of the first arm and the second arm is capable of changing shape from a first shape conformation, wherein the first arm and the second arm spread outward from a centerline through the connection apparatus, to be insertable into a body of a patient, to a second shape conformation, wherein the first arm and the second arm span inward toward the centerline through at least one of the first arm, the second arm, or the connection apparatus, to be attachable to the exterior of the blood vessel for operation of the sensor device.

18. The sensor device of claim 1, wherein the fluid flow parameter of the blood in the blood vessel includes at least one of a flow rate, or an amount of pressure difference between ends of a flow path in the blood vessel.

19. The sensor device of claim 1, wherein the first arm and the second arm are positioned on a superior vena cava or an inferior vena cava, and wherein the received acoustic signals are indicative of blood flow within the superior vena cava or the inferior vena cava.

20. The sensor device of claim 1, wherein the first arm and the second arm are positioned on a pulmonary artery or pulmonary vein, and wherein the received acoustic signals are indicative of blood flow within the pulmonary artery or the pulmonary vein.

* * * * *